(12) United States Patent
Kim et al.

(10) Patent No.: US 8,278,285 B2
(45) Date of Patent: Oct. 2, 2012

(54) GASTRIC CARCINOMA GENE ZNF312B, A PROTEIN TRANSLATED FROM THE GENE, AND A DIAGNOSTIC KIT AND A SCREENING METHOD FOR ANTICANCER AGENTS USING THE SAME

(75) Inventors: Nam-Soon Kim, Daejeon (KR); In-Sung Song, Incheon (KR); Nang-Su Oh, Gyeryong-si (KR); So-Young Jeong, Daejeon (KR); Ga-Hee Ha, Busan (KR); Yeo-Jin Jeon, Daejeon (KR); Jeong-Min Kim, Gumi-si (KR); Cheol-Hee Kim, Daejeon (KR); Hyun-Taek Kim, Daejeon (KR)

(73) Assignee: Korea Research Institute of Bioscience and Biotechnology, Daejon (KR)

( * ) Notice: Subject to any disclaimer, the term of this patent is extended or adjusted under 35 U.S.C. 154(b) by 72 days.

(21) Appl. No.: 12/594,843

(22) PCT Filed: Aug. 6, 2008

(86) PCT No.: PCT/KR2008/004566
§ 371 (c)(1),
(2), (4) Date: Oct. 6, 2009

(87) PCT Pub. No.: WO2009/020346
PCT Pub. Date: Feb. 12, 2009

(65) Prior Publication Data
US 2010/0162420 A1    Jun. 24, 2010

(30) Foreign Application Priority Data

| Aug. 6, 2007 | (KR) | 10-2007-0078585 |
| Aug. 21, 2007 | (KR) | 10-2007-0083814 |
| Jul. 25, 2008 | (KR) | 10-2008-0073044 |

(51) Int. Cl.
*A61K 31/70* (2006.01)
*C07H 21/04* (2006.01)
(52) U.S. Cl. ............ 514/44; 536/23.1; 536/24.5
(58) Field of Classification Search .............. 514/44; 536/23.1, 24.5
See application file for complete search history.

(56) References Cited

U.S. PATENT DOCUMENTS
2007/0161018 A1    7/2007   Inazawa et al. ............... 435/6

FOREIGN PATENT DOCUMENTS
KR    10-2006-0013868 A    2/2006

OTHER PUBLICATIONS

Bertrand Jr, et al., Biochem Biophys Res Commun. Aug. 30, 2002;296(4):1000-4. Comparison of antisense oligonucleotides and siRNAs in cell culture and in vivo.*
Song et al.Cancer Res. Apr. 1, 2009;69(7):3131-9. Epub Mar. 24, 2009. Human ZNF312b promotes the progression of gastric cancer by transcriptional activation of the K-ras gene.*
Tan et al., Proc Natl Acad Sci U S A. Oct. 14, 2003;100(21):11997-2002. Epub Sep. 26, 2003. Zinc-finger protein-targeted gene regulation: genomewide single-gene specificity.*
Greisman et al Science. Jan. 31, 1997;275(5300):657-61. A general strategy for selecting high-affinity zinc finger proteins for diverse DNA target sites.*
Jaaskela et al., 2004 Methods in Enzymology, vol. 387 pp. 210-230 Requirements for Delivery of Active Antisense Oligonucleotides into Cells with Lipid Carriers.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-495.*
Rudinger, J., "Characteristics of the amino acids as components of a peptide hormone sequence",in Peptide Hormones, University Park Press: Baltimore, MD, pp. 1-7, 1976.*
Voet, Biochemistry John Wiley and Sons, 1990, pp. 126-128.*
Guo et al Proc Natl Acad Sci U S A. Jun. 22, 2004;101(25):9205-10. Epub Jun. 14, 2004.Protein tolerance to random amino acid change.*
NCBI Accession No. AY726588.1 [gi:53851203] Nov. 1, 2004.
Aung et al., "Systematic search for gastric cancer-specific genes based on SAGE data:melanoma inhibitory activity and matrix metalloproteinase-10 are novel prognostic factors in patients with gastric cancer", Oncogene 2006 25:2546-2557.

* cited by examiner

*Primary Examiner* — Maria Leavitt
(74) *Attorney, Agent, or Firm* — Licata & Tyrell P.C.

(57) ABSTRACT

The present invention relates to a diagnostic marker containing ZNF312b gene and the fragment thereof, a diagnostic method for stomach cancer and a screening method for stomach cancer inducers or inhibitors using the same. ZNF312b gene expression is specifically increased in stomach cancer. And the over-expression or the under-expression of the gene affects activation or inhibition of cell proliferation and tumor formation of a stomach cancer cell line and cell proliferation signal transduction system as well to induce stomach cancer at last. Therefore, ZNF312b marker gene can be effectively used for diagnosis of stomach cancer, construction of a stomach cancer animal model, prevention and treatment of stomach cancer and development of a stomach cancer specific anticancer agent.

2 Claims, 33 Drawing Sheets

[Fig. 27]

Fig. 33
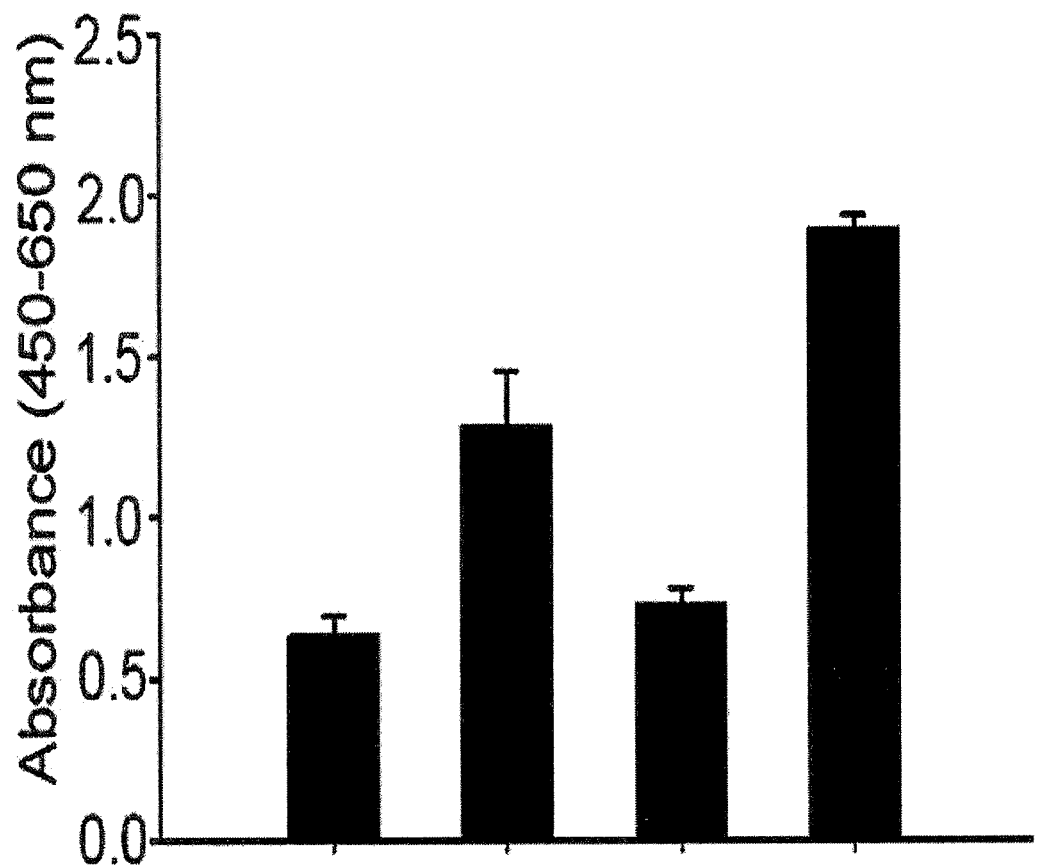
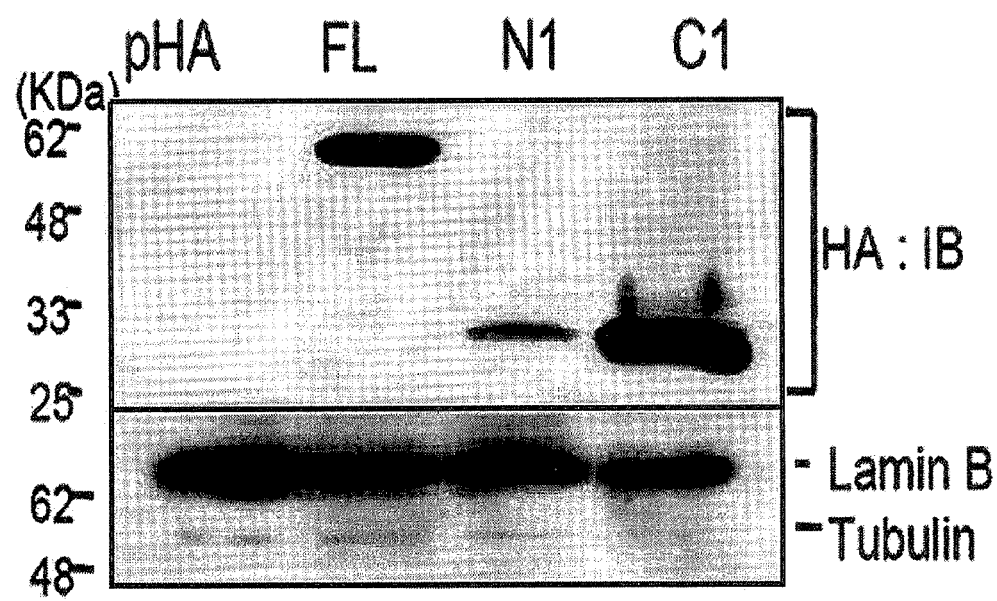

SEQUENCE LISTING

<160> NUMBER OF SEQ ID NOS: 20

<210> SEQ ID NO 1
<211> LENGTH: 2026
<212> TYPE: DNA
<213> ORGANISM: Homo sapiens

<400> SEQUENCE: 1

```
cagtagctgc cacaacgcga ctaccaaaat gttagcgact gctccagctc ggggcaacat      60
gatgagcacg tccaaaccct tggctttctc cattgaacga atcatggcgc gcaccccaga     120
gcccaaggcc ctgccagtcc cccacttcct gcagggagcc ttacccaagg gggaacccaa     180
gcactctctg catctcaact cgtcgatccc ctgcatgatc cccttcgtgc ctgtggccta     240
cgacacgagc cccaaggcag gagtgacggg ctccgagccg cggaaggcca gtctggaggc     300
cccggcggcg cccgcggcgg tgccctcggc tcccgcattc agctgcagcg acctgctcaa     360
ctgcgcactg agtctcaagg gcgacctggc ccgcgacgcg ctgccgctgc agcagtacaa     420
gctggtaagg ccgcgtgtgg tcaaccactc ttcattccac gccatgggcg ccttgtgcta     480
cctgaaccga ggtgacggcc catgccaccc ggcagccggc gtgaacatcc acccggtggc     540
ctcctacttc ctcagttccc ctttgcaccc gcagccaaaa acgtatttag ccgaaaggaa     600
taaactggtg gtcccggcgg tggagaaata cccttctgga gtagctttca aagacctgtc     660
ccaggctcag ctgcagcatt acatgaaaga aagcgcccag cttctgtcgg aaaaaatcgc     720
gttcaaaacc tcggatttca gccgaggctc tcctaatgcc aagcccaaag ttttcacttg     780
```

```
cgaagtgtgt ggaaaggtct ttaatgcgca ctataactta acccgtcaca tgccagtgca    840
cacaggagcc agacccttcg tttgcaaagt gtgcggaaaa ggtttcaggc aagcaagcac    900
cctgtgcagg cacaagatca ttcacacgca ggaaaaacct cacaaatgta accagtgtgg    960
caaagcattt aatagaagtt ccactttaaa cactcatacc cgaatacacg cgggctacaa   1020
accgtttgtg tgtgaattct gtggcaaagg gtttcatcaa aaagggaatt acaaaaacca   1080
caagttgacc cacagcgggg agaagcagtt caagtgcaat atctgcaaca aggcttttca   1140
ccaggtttac aacctcacct tccacatgca cacccacaac gacaagaagc ctttcacctg   1200
ccccacgtgc ggcaagggtt tctgcaggaa ctttgacctc aagaagcatg tccgcaagct   1260
gcacgacagc agcctgggc tggcccgcac gccagctggc gaaccaggca ctgaaccgcc    1320
gcccccgcta ccgcagcagc cgccgatgac gctgcctcct ctgcagccgc cgctgccaac   1380 cccgggccc ctgcagcccg ggctccacca gggccaccag tgatcgaggc taagggtcct    1440
cccagcctca gccgtgcccc cacgctgagg cagcggcaga ctagagctcc tggtccgagt   1500
tcgtctgcag accccagggc atgttgggcc ccacacttca gggccgacca gaagcctctg   1560
catcccctgg cctttcgcct cttgcatgca cctgctaaat ggttttgtgt attatattct   1620
atataggcac taacaattat gaaaaatttg gagggttttg cttgttttct gttttctttt   1680
ttcttttttt ttaatttgga aagacttttc atcttgggtg gagagatggt gtttattttg   1740
ttttgttttg tttaaacaaa tttctgctat atttattgag atctgtatta ttctacccgg   1800
gaatgctgca tcattttaat tttattattg tatatatttc cattgtgttg attctccggt   1860
ctcaagatgt ctgctggatg ttgatcattt cctctttccc tgaagtaaca aaaccctgtg   1920
tgtatgtcat atatacacgc atagatgtgt gcgcccatag gggtacattc cacattcgtg   1980
agcacacacc catacacatt agataagggt ggttcattat ggatga                 2026

<210> SEQ ID NO 2
<211> LENGTH: 454
<212> TYPE: PRT
<213> ORGANISM: Homo sapiens

<400> SEQUENCE: 2

Met Met Ser Thr Ser Lys Pro Leu Ala Phe Ser Ile Glu Arg Ile Met
1               5                   10                  15

Ala Arg Thr Pro Glu Pro Lys Ala Leu Pro Val Pro His Phe Leu Gln
                20                  25                  30

Gly Ala Leu Pro Lys Gly Glu Pro Lys His Ser Leu His Leu Asn Ser
            35                  40                  45

Ser Ile Pro Cys Met Ile Pro Phe Val Pro Val Ala Tyr Asp Thr Ser
        50                  55                  60

Pro Lys Ala Gly Val Thr Gly Ser Glu Pro Lys Ala Ser Leu Glu
65                  70                  75                  80

Ala Pro Ala Ala Pro Ala Val Pro Ser Ala Pro Ala Phe Ser Cys
                85                  90                  95

Ser Asp Leu Leu Asn Cys Ala Leu Ser Leu Lys Gly Asp Leu Ala Arg
            100                 105                 110

Asp Ala Leu Pro Leu Gln Gln Tyr Lys Leu Val Arg Pro Arg Val Val
        115                 120                 125

Asn His Ser Ser Phe His Ala Met Gly Ala Leu Cys Tyr Leu Asn Arg
    130                 135                 140

Gly Asp Gly Pro Cys His Pro Ala Ala Gly Val Asn Ile His Pro Val
145                 150                 155                 160
```

```
Ala Ser Tyr Phe Leu Ser Ser Pro Leu His Pro Gln Pro Lys Thr Tyr
                165                 170                 175
Leu Ala Glu Arg Asn Lys Leu Val Val Pro Ala Val Glu Lys Tyr Pro
            180                 185                 190
Ser Gly Val Ala Phe Lys Asp Leu Ser Gln Ala Gln Leu Gln His Tyr
        195                 200                 205
Met Lys Glu Ser Ala Gln Leu Leu Ser Glu Lys Ile Ala Phe Lys Thr
    210                 215                 220
Ser Asp Phe Ser Arg Gly Ser Pro Asn Ala Lys Pro Lys Val Phe Thr
225                 230                 235                 240
Cys Glu Val Cys Gly Lys Val Phe Asn Ala His Tyr Asn Leu Thr Arg
                245                 250                 255
His Met Pro Val His Thr Gly Ala Arg Pro Phe Val Cys Lys Val Cys
            260                 265                 270
Gly Lys Gly Phe Arg Gln Ala Ser Thr Leu Cys Arg His Lys Ile Ile
        275                 280                 285
His Thr Gln Glu Lys Pro His Lys Cys Asn Gln Cys Gly Lys Ala Phe
    290                 295                 300
Asn Arg Ser Ser Thr Leu Asn Thr His Thr Arg Ile His Ala Gly Tyr
305                 310                 315                 320
Lys Pro Phe Val Cys Glu Phe Cys Gly Lys Gly Phe His Gln Lys Gly
                325                 330                 335
Asn Tyr Lys Asn His Lys Leu Thr His Ser Gly Glu Lys Gln Phe Lys
            340                 345                 350
Cys Asn Ile Cys Asn Lys Ala Phe His Gln Val Tyr Asn Leu Thr Phe
        355                 360                 365
His Met His Thr His Asn Asp Lys Lys Pro Phe Thr Cys Pro Thr Cys
    370                 375                 380
Gly Lys Gly Phe Cys Arg Asn Phe Asp Leu Lys Lys His Val Arg Lys
385                 390                 395                 400
Leu His Asp Ser Ser Leu Gly Leu Ala Arg Thr Pro Ala Gly Glu Pro
                405                 410                 415
Gly Thr Glu Pro Pro Pro Leu Pro Gln Gln Pro Pro Met Thr Leu
            420                 425                 430
Pro Pro Leu Gln Pro Pro Leu Thr Pro Gly Pro Leu Gln Pro Gly
        435                 440                 445
Leu His Gln Gly His Gln
    450

<210> SEQ ID NO 3
<211> LENGTH: 18
<212> TYPE: DNA
<213> ORGANISM: Artificial
<220> FEATURE:
<223> OTHER INFORMATION: forward primer of ZNF312b

<400> SEQUENCE: 3
cgaagtgtgt ggaaaggt                                                   18

<210> SEQ ID NO 4
<211> LENGTH: 20
<212> TYPE: DNA
<213> ORGANISM: Artificial
<220> FEATURE:
<223> OTHER INFORMATION: reverse primer of ZNF312b

<400> SEQUENCE: 4
```

-continued

```
aatacacgcg ggctacaaac                                          20

<210> SEQ ID NO 5
<211> LENGTH: 19
<212> TYPE: DNA
<213> ORGANISM: Artificial
<220> FEATURE:
<223> OTHER INFORMATION: si-ZNF312b-1

<400> SEQUENCE: 5
gcactctctg catctcaac                                           19

<210> SEQ ID NO 6
<211> LENGTH: 19
<212> TYPE: DNA
<213> ORGANISM: Artificial
<220> FEATURE:
<223> OTHER INFORMATION: si-ZNF312b-1

<400> SEQUENCE: 6
gcactctctg catctcaac                                           19

<210> SEQ ID NO 7
<211> LENGTH: 19
<212> TYPE: DNA
<213> ORGANISM: Artificial
<220> FEATURE:
<223> OTHER INFORMATION: si-ZNF312b-2

<400> SEQUENCE: 7
gtgtgtggaa aggtcttta                                           19

<210> SEQ ID NO 8
<211> LENGTH: 19
<212> TYPE: DNA
<213> ORGANISM: Artificial
<220> FEATURE:
<223> OTHER INFORMATION: si-ZNF312b-3

<400> SEQUENCE: 8
gcagttcaag tgcaatatc                                           19

<210> SEQ ID NO 9
<211> LENGTH: 3000
<212> TYPE: DNA
<213> ORGANISM: Homo sapiens

<400> SEQUENCE: 9
ttttgcagtt aaggagaggg gaggggagg agaggaaggg gagagtgagg gacacaccac    60
aagcgtaaaa cgaactggtg gcattcagtc aagaaggcag gtaaggctcc agaggccgcg   120
aattgtgtac aagtcagctg gactctccaa agccttccag agccgggctg cttcgcgctt   180
cttggctttt tcctttcaac ctagcccggt ggcggaggag tgcagcagga gggggatttt   240
tcgctgctgg gaagtggcag gtaggaaaag gaatctgatc cggcccaaaa gtcagcaatt   300
aaagtcttaa ccgcgaccca tctgtcgtgg gacagagaac cccccacccc ctttgcccc    360 agcaaagccc ttcccgtgcc ctttgtctga gcagggaaaa ggaggagact ggttctgcgg   420
ccccaacagc aaaggaaag aaaatttcca gcgctgacca atactgagtg tctgcgcccg    480
gtccaaggac aactacgaag cgcctctcgg ggatgtggcg cctctccgct tgctctgccc    540
aggtgctctg tcccgtggcc ccagcaaaag gaaagaaaaa tttgcagtct gggcgaatcc    600
aaagtaggtg cacccgggcc aaggacggtt ccaaagggcc gccttggagt gtagcgcctc    660
```

```
tttgctttct ccccccgggc gctctgccct tctctgctgc atcagttgtc ccagcctgaa      720
gccacctcga ggcctgaaac gaggcactcc caggcctagc tgctgaagcc cgtcgtattc      780
agccagacct ctcccccat cttgccccctt ggctgtcctc aacttccaat aagactcact      840
cccctccc catttcttca gcctgtgagc tttcccacca ctcacccagc tgccactgcc       900
tttctgttag acatcaggcg cgttcccagc ccaagctctc ttcctttcca ccctcttgg       960
ctcttggggc agaggcggaa ctgattttcg cggaaagtta gagtggggcg gagggacccg      1020
ggtagcttgc ctggcatgtg ttgagaatgg ggtagagagg agggaatact ttgacgtcaa      1080
tttccttcgt ttaaggtcca gtttcgcatc tttgagtgaa attgctcagg gacttaataa      1140
tgccagggtt tctagtccgc cgttatccag ccttccgggg ccaaccctt tcagagctct      1200
agcagaagga cgccccccact acacttggcc caatacctga cacccgccac cacctgtctc     1260
acagccacgt ggggttaact caccaggcag atggcacctt gagctgctgc ggtcggccac      1320
tcacttcagg gtccaggccc caccgccctt tgcttgcagc tctgcgcgct cctttggcct      1380
cctcacgcca gcttacagct gccgtgtctt caaactctgt gcagcccttc ctgcgcgcct      1440
agctgcgggg ttcagctctg cgtgatcgcc ggctggcaag agactgcgcc ggggaaggtg      1500
cgcgccgcag cttccagcgc gctcctggac gctcttgcct gggcggcggg agcccgcaca      1560
gtcggagccg cagccgtagg cgtcttcccg gaaacctcca cacgctccac cgcgccgccc      1620
caggagtttc ggccgaggtg ccacacccgg cgggtgttcg gctgggggc gttgcagggg      1680
aaatggtctc tacgcgcgct ctttgggagg cacaagtgca cctgtggaca caactctggc      1740
gccggcaagt ctccttgatg cgcacagaca tccaggctgc cgcctgcgct gcttagagga      1800
ggcttgcaga caccggcaac cggagtgggg attaatacac tctgtttccc ttctccgctc      1860
ggcattcagt atttaaaatg ctccgggaga gctctagctg agcgcaggta cttaagaaag      1920
aaatgctctt tccagactct caatggaaac tcggaagcgt gcgcgcgcgc gcgtctgtgt      1980
gtatcctggg tggggtccga tcgagtcaag gttgcttgtg gtgtgacacc caattattcc      2040
ttgcaactcc tcaactttgt ggatgaaagt gcgactttcc caggcctatt gccgcgggca      2100
ttgcctttac aaaaccacaa acacagaaca agcctcctaa ggcttttaat tttcggggcg      2160
tttggggagg ccagttacct gccggcgtct tctaaatggt ccagactcgg ttcgggccgc      2220
ggagactccg ggattccggg agcgggcaac cccgagccct ggaggaagaa ataggtctgc      2280
ggaggtggca cagatctgac ccggcccagc ccggcccagc ccggcccacc caggcccagt      2340
ggaaccaagc agcgaaacct cggatttcac tgccgaggct tcctagccga ggctttctgg      2400
agcttggcgt ttgataaata tagcctggcg tttgcccctg aattagactc cgtttcctta      2460
tttagcccctt gcacaatgat tttagatgat gtcacttaga gctaaacgag aaaattgatc      2520
tcagatttgc ttggcctcta aagcctggtt aagcagattg agaattagaa aggcagagga      2580
agcaaaaggg gggtggggat ggggggtgc ggagggtagt gaagtgtgcg cggcagagtg      2640
tgtgcgcaga ggggagggcg cgccaagcgg gtgaaagcgc cccgcctttt tctgggcggg      2700
gaacctcact caccaatgaa aagtagttac tgactgcaga tgaaaaaaaa aaagttttc      2760
ctgttgactg ttggaagcga attgagcaat tatctagttt accttctcct cttggaagtt      2820
aacgattggc gagatcttgg ctgcgttatt gacacaacac tttctattga tagaaataag      2880
tagtgattgt ccccgagtca ttggtgcgcc aagaactctg cgatgggctg gcaggagtcc      2940
attgggctgg gcaggcaggt tcggctggtg atgctgggga ggaggaggag gaggaggcta      3000
```

<210> SEQ ID NO 10

<211> LENGTH: 2000
<212> TYPE: DNA
<213> ORGANISM: Homo sapiens

<400> SEQUENCE: 10

| | | | | | | |
|---|---|---|---|---|---|---|
| gagtggggcg | agggacccg | ggtagcttgc | ctggcatgtg | ttgagaatgg | ggtagagagg | 60 |
| agggaatact | ttgacgtcaa | tttccttcgt | ttaaggtcca | gtttcgcatc | tttgagtgaa | 120 |
| attgctcagg | gacttaataa | tgccaggggtt | tctagtccgc | cgttatccag | ccttccgggg | 180 |
| ccaaccctttt | tcagagctct | agcagaagga | cgcccccact | acacttggcc | caatacctga | 240 |
| cacccgccac | cacctgtctc | acagccacgt | ggggttaact | caccaggcag | atggcaccttt | 300 |
| gagctgctgc | ggtcggccac | tcacttcagg | gtccaggccc | caccgcccttt | tgcttgcagc | 360 |
| tctgcgcgct | cctttggcct | cctcacgcca | gcttacagct | gccgtgtcttt | caaactctgt | 420 |
| gcagccttc | ctgcgcgcct | agctgcgggg | ttcagctctg | cgtgatcgcc | ggctggcaag | 480 |
| agactgcgcc | ggggaaggtg | cgcgccgcag | cttccagcgc | gctcctggac | gctcttgcct | 540 |
| gggcggcggg | agcccgcaca | gtcggagccg | cagccgtagg | cgtcttcccg | gaaacctcca | 600 |
| cacgctccac | cgcgccgccc | caggagtttc | ggccgaggtg | ccacacccgg | cgggtgttcg | 660 |
| gctgggggggc | gttgcagggg | aaatggtctc | tacgcgcgct | ctttgggagg | cacaagtgca | 720 |
| cctgtggaca | caactctggc | gccggcaagt | ctccttgatg | cgcacagaca | tccaggctgc | 780 |
| cgcctgcgct | gcttagagga | ggcttgcaga | caccggcaac | cggagtgggg | attaatacac | 840 |
| tctgttttccc | ttctccgctc | ggcattcagt | atttaaaatg | ctccgggaga | gctctagctg | 900 |
| agcgcaggta | cttaagaaag | aaatgctctt | tccagactct | caatggaaac | tcggaagcgt | 960 |
| gcgcgcgcgc | gcgtctgtgt | gtatcctggg | tggggtccga | tcgagtcaag | gttgcttgtg | 1020 |
| gtgtgacacc | caattattcc | ttgcaactcc | tcaactttgt | ggatgaaagt | gcgactttcc | 1080 |
| caggcctatt | gccgcgggca | ttgccttttac | aaaaccacaa | acacagaaca | agcctcctaa | 1140 |
| ggcttttaat | tttcggggcg | tttggggagg | ccagttacct | gccggcgtct | tctaaatggt | 1200 |
| ccagactcgg | ttcgggccgc | ggagactccg | ggattccggg | agcgggcaac | cccgagccct | 1260 |
| ggaggaagaa | ataggtctgc | ggaggtggca | cagatctgac | ccggcccagc | ccggcccagc | 1320 |
| ccggcccacc | caggcccagt | ggaaccaagc | agcgaaacct | cggatttcac | tgccgaggct | 1380 |
| tcctagccga | ggctttctgg | agcttggcgt | ttgataaata | tagcctggcg | tttgcccctg | 1440 |
| aattagactc | cgtttcctta | tttagcccttt | gcacaatgat | tttagatgat | gtcacttaga | 1500 |
| gctaaacgag | aaaattgatc | tcagatttgc | ttggcctcta | aagcctggtt | aagcagattg | 1560 |
| agaattagaa | aggcagagga | agcaaagggg | gggtggggat | ggggggggtgc | ggagggtagt | 1620 |
| gaagtgtgcg | cggcagagtg | tgtgcgcaga | ggggagggcg | cgccaagcgg | gtgaaagcgc | 1680 |
| ccccgccttt | tctgggcggg | gaacctcact | caccaatgaa | aagtagttac | tgactgcaga | 1740 |
| tgaaaaaaaa | aaaagtttttc | ctgttgactg | ttggaagcga | attgagcaat | tatctagttt | 1800 |
| accttctcct | cttggaagtt | aacgattggc | gagatcttgg | ctgcgttatt | gacacaacac | 1860 |
| tttctattga | tagaaataag | tagtgattgt | ccccgagtca | ttggtgcgcc | aagaactctg | 1920 |
| cgatgggctg | gcaggagtcc | attgggctgg | gcaggcaggt | tcggctggtg | atgctgggga | 1980 |
| ggaggaggag | gaggaggcta | | | | | 2000 |

<210> SEQ ID NO 11
<211> LENGTH: 1000
<212> TYPE: DNA
<213> ORGANISM: Homo sapiens -continued

```
<400> SEQUENCE: 11
tcgagtcaag gttgcttgtg gtgtgacacc caattattcc ttgcaactcc tcaactttgt      60
ggatgaaagt gcgactttcc caggcctatt gccgcgggca ttgcctttac aaaaccacaa     120
acacagaaca agcctcctaa ggcttttaat tttcggggcg tttggggagg ccagttacct     180
gccggcgtct tctaaatggt ccagactcgg ttcgggccgc ggagactccg ggattccggg     240
agcgggcaac cccgagccct ggaggaagaa ataggtctgc ggaggtggca cagatctgac     300
ccggcccagc ccggcccagc ccggcccacc caggcccagt ggaaccaagc agcgaaacct     360
cggatttcac tgccgaggct tcctagccga ggctttctgg agcttggcgt ttgataaata     420
tagcctggcg tttgcccctg aattagactc cgtttcctta tttagcccctt gcacaatgat    480
tttagatgat gtcacttaga gctaaacgag aaaattgatc tcagatttgc ttggcctcta     540
aagcctggtt aagcagattg agaattagaa aggcagagga agcaaaaggg gggtggggat     600
ggggggggtgc ggagggtagt gaagtgtgcg cggcagagtg tgtgcgcaga ggggagggcg    660
cgccaagcgg gtgaaagcgc ccccgccttt tctgggcggg gaacctcact caccaatgaa    720
aagtagttac tgactgcaga tgaaaaaaaa aaaagttttc ctgttgactg ttggaagcga    780
attgagcaat tatctagttt accttctcct cttggaagtt aacgattggc gagatcttgg     840
ctgcgttatt gacacaacac tttctattga tagaaataag tagtgattgt ccccgagtca    900
ttggtgcgcc aagaactctg cgatgggctg gcaggagtcc attgggctgg gcaggcaggt    960
tcggctggtg atgctgggga ggaggaggag gaggaggcta                         1000

<210> SEQ ID NO 12
<211> LENGTH: 850
<212> TYPE: DNA
<213> ORGANISM: Homo sapiens

<400> SEQUENCE: 12
tttcggggcg tttggggagg ccagttacct gccggcgtct tctaaatggt ccagactcgg      60
ttcgggccgc ggagactccg ggattccggg agcgggcaac cccgagccct ggaggaagaa     120
ataggtctgc ggaggtggca cagatctgac ccggcccagc ccggcccagc ccggcccacc     180
caggcccagt ggaaccaagc agcgaaacct cggatttcac tgccgaggct tcctagccga     240
ggctttctgg agcttggcgt ttgataaata tagcctggcg tttgcccctg aattagactc     300
cgtttcctta tttagcccctt gcacaatgat tttagatgat gtcacttaga gctaaacgag    360
aaaattgatc tcagatttgc ttggcctcta aagcctggtt aagcagattg agaattagaa     420
aggcagagga agcaaaaggg gggtggggat ggggggggtgc ggagggtagt gaagtgtgcg    480
cggcagagtg tgtgcgcaga ggggagggcg cgccaagcgg gtgaaagcgc ccccgccttt    540
tctgggcggg gaacctcact caccaatgaa aagtagttac tgactgcaga tgaaaaaaaa     600
aaaagttttc ctgttgactg ttggaagcga attgagcaat tatctagttt accttctcct    660
cttggaagtt aacgattggc gagatcttgg ctgcgttatt gacacaacac tttctattga    720
tagaaataag tagtgattgt ccccgagtca ttggtgcgcc aagaactctg cgatgggctg    780
gcaggagtcc attgggctgg gcaggcaggt tcggctggtg atgctgggga ggaggaggag     840
gaggaggcta                                                          850

<210> SEQ ID NO 13
<211> LENGTH: 650
<212> TYPE: DNA
<213> ORGANISM: Homo sapiens
```

```
<400> SEQUENCE: 13
agcgaaacct cggatttcac tgccgaggct tcctagccga ggctttctgg agcttggcgt    60
ttgataaata tagcctggcg tttgcccctg aattagactc cgtttcctta tttagcccct   120
gcacaatgat tttagatgat gtcacttaga gctaaacgag aaaattgatc tcagatttgc   180
ttggcctcta aagcctggtt aagcagattg agaattagaa aggcagagga agcaaaaggg   240
gggtggggat ggggggggtgc ggagggtagt gaagtgtgcg cggcagagtg tgtgcgcaga   300
ggggagggcg cgccaagcgg gtgaaagcgc ccccgccttt tctgggcggg gaacctcact   360
caccaatgaa aagtagttac tgactgcaga tgaaaaaaaa aaagttttc ctgttgactg    420 ttggaagcga attgagcaat tatctagttt accttctcct cttggaagtt aacgattggc   480
gagatcttgg ctgcgttatt gacacaacac tttctattga tagaaataag tagtgattgt   540
ccccgagtca ttggtgcgcc aagaactctg cgatgggctg gcaggagtcc attgggctgg   600
gcaggcaggt tcggctggtg atgctgggga ggaggaggag gaggaggcta              650

<210> SEQ ID NO 14
<211> LENGTH: 500
<212> TYPE: DNA
<213> ORGANISM: Homo sapiens

<400> SEQUENCE: 14
gctaaacgag aaaattgatc tcagatttgc ttggcctcta aagcctggtt aagcagattg    60
agaattagaa aggcagagga agcaaaaggg gggtggggat ggggggggtgc ggagggtagt  120 gaagtgtgcg cggcagagtg tgtgcgcaga ggggagggcg cgccaagcgg gtgaaagcgc  180
ccccgccttt tctgggcggg gaacctcact caccaatgaa aagtagttac tgactgcaga  240
tgaaaaaaaa aaagttttc ctgttgactg ttggaagcga attgagcaat tatctagttt   300
accttctcct cttggaagtt aacgattggc gagatcttgg ctgcgttatt gacacaacac  360
tttctattga tagaaataag tagtgattgt ccccgagtca ttggtgcgcc aagaactctg  420
cgatgggctg gcaggagtcc attgggctgg gcaggcaggt tcggctggtg atgctgggga  480
ggaggaggag gaggaggcta                                              500

<210> SEQ ID NO 15
<211> LENGTH: 2000
<212> TYPE: DNA
<213> ORGANISM: Homo sapiens

<400> SEQUENCE: 15
ttaggtgctg gaaatttagc agtaaatgaa acagaccaaa acccatgccc tcatggagct    60
tacattctga tggtagagag acaagaaaac aaaatagata gtgtattatt gaaggtgatg   120
agagctctgg agaaaaagta ggaaaagaga cagatctggg acaagggcga aattacagta   180
tcaaagatga tcttttttagg gaagatctcc ttttaaaaac actttggaac aaagatttaa   240
atgaggtgcc agaggggtag caagtgcata ttccctgagg aagacgcctg cctggcattt   300
tcaaggaaca gccagtaacc aatgtttatc tacgtaagta aggaagggag aacagtagga   360
tgagagttca gagaagaggg taggggatat caaataattt aaggccatgt aggattttg    420 agaagaattt tgcttttatg tcaagtggaa tgagggccac tgatgatctg ggagtagagt   480
gactatgatc cgacatgaag tatactccat tttttaacta tgtgaacttg tgccaacgtt   540
ttaacctcta aatctgtttc gtcatttgta aacggtaaa aagtatttta cctcataagg    600
ttgtcgtgat gattaaataa gatgatacga taagtgcaaa agatttagct tgtacttaac  660
```

```
atagagtagg cacattttct cccttccct gtctttcact tttctcttct gcccttcca      720
cctggcgcta ggaggggag actggaataa accttgcaga ttacagcccg tgtaagagta      780
gaaaggaaag gatgacagtt gatgtaaagc cttggttaac agacataata gctgggattt      840
aaattcagct ttattggtgg tttatgatgt ggactagagg aatggaactg aaagtctcgg      900
aggaggggcg atcctatcag gtacaggcgc tgcttttcca gccctcaatc ctcaagactc      960
tcccaagata catttctagg tagtttatca acacagactc cgggtatgct agcatgttta     1020
attgccccat tgtttaatgt cttaactcca cgaactttaa ctgattaatc tgtcttctaa     1080
ttaatgtttg aatgactctc ctcaggtcta aactaccaag gccatctcta cttaaaaaca     1140
gttgtctttt gtttgtgatt tcaggggccc tgggtataag cgaagtccct gtttagagac     1200
cttgtgatgg gttcaaaata tcaagaaaga tagcaaaata tcacaagcct cctgacccga     1260
gaagattagc gttgaaaggg tctgtcgtgt ttgtttgggc ctggggctaa attcccagcc     1320
caagtgctga ggctgataat aatcggggcg gcgatcagac agccccggtg tgggaaatcg     1380
tccgcccggt ctccctaagt ccccgaagtc gcctcccact tttggtgact gcttgtttat     1440
ttacatgcag tcaatgatag taaatggatg cgcgccagta taggccgacc ctgagggtgg     1500
cggggtgctc ttcgcagctt ctctgtggag accggtcagc ggggcggcgt ggccgctcgc     1560
ggcgtctccc tggtggcatc cgcacagccc gccgcggtcc ggtcccgctc cgggtcagaa     1620
ttggcggctg cggggacagc cttgcggcta ggcaggggc gggccgccgc gtgggtccgg      1680
cagtccctcc tcccgccaag gcgccgccca gacccgctct ccagccggcc cggctcgcca     1740
ccctagaccg ccccagccac cccttcctcc gccggcccgg ccccgctcc tccccgccg      1800
gcccggcccg gccccctcct tctccccgcc ggcgctcgct gcctcccct cttccctctt      1860
cccacaccgc cctcagccgc tccctctcgt acgcccgtct gaagaagaat cgagcgcgga     1920
acgcatcgat agctctgccc tctgcggccg cccggccccg aactcatcgg tgtgctcgga     1980
gctcgatttt cctaggcggc                                                2000

<210> SEQ ID NO 16
<211> LENGTH: 1000
<212> TYPE: DNA
<213> ORGANISM: Homo sapiens

<400> SEQUENCE: 16
cgggtatgct agcatgttta attgccccat tgtttaatgt cttaactcca cgaactttaa       60
ctgattaatc tgtcttctaa ttaatgtttg aatgactctc ctcaggtcta aactaccaag      120
gccatctcta cttaaaaaca gttgtctttt gtttgtgatt tcaggggccc tgggtataag      180
cgaagtccct gtttagagac cttgtgatgg gttcaaaata tcaagaaaga tagcaaaata      240
tcacaagcct cctgacccga gaagattagc gttgaaaggg tctgtcgtgt ttgtttgggc      300
ctggggctaa attcccagcc caagtgctga ggctgataat aatcggggcg gcgatcagac      360
agccccggtg tgggaaatcg tccgcccggt ctccctaagt ccccgaagtc gcctcccact      420
tttggtgact gcttgtttat ttacatgcag tcaatgatag taaatggatg cgcgccagta      480
taggccgacc ctgagggtgg cggggtgctc ttcgcagctt ctctgtggag accggtcagc      540
ggggcggcgt ggccgctcgc ggcgtctccc tggtggcatc cgcacagccc gccgcggtcc      600
ggtcccgctc cgggtcagaa ttggcggctg cggggacagc cttgcggcta ggcaggggc      660
gggccgccgc gtgggtccgg cagtccctcc tcccgccaag gcgccgccca gacccgctct      720
ccagccggcc cggctcgcca ccctagaccg ccccagccac cccttcctcc gccggcccgg      780
```

| | |
|---|---|
| ccccgctcc tcccccgccg gcccggcccg gcccctcct tctcccgcc ggcgctcgct | 840 |
| gcctccccct cttccctctt cccacaccgc cctcagccgc tccctctcgt acgcccgtct | 900 |
| gaagaagaat cgagcgcgga acgcatcgat agctctgccc tctgcggccg cccggccccg | 960 |
| aactcatcgg tgtgctcgga gctcgatttt cctaggcggc | 1000 |

<210> SEQ ID NO 17
<211> LENGTH: 650
<212> TYPE: DNA
<213> ORGANISM: Homo sapiens

<400> SEQUENCE: 17

| | |
|---|---|
| gcgatcagac agccccggtg tgggaaatcg tccgcccggt ctccctaagt ccccgaagtc | 60 |
| gcctcccact tttggtgact gcttgtttat ttacatgcag tcaatgatag taaatggatg | 120 |
| cgcgccagta taggccgacc ctgagggtgg cggggtgctc ttcgcagctt ctctgtggag | 180 |
| accggtcagc ggggcggcgt ggccgctcgc ggcgtctccc tggtggcatc cgcacagccc | 240 |
| gccgcggtcc ggtcccgctc cgggtcagaa ttggcggctg cggggacagc cttgcggcta | 300 |
| ggcaggggc gggccgccgc gtgggtccgg cagtccctcc tcccgccaag gcgccgccca | 360 |
| gacccgctct ccagccggcc cggctcgcca ccctagaccg ccccagccac cccttcctcc | 420 |
| gccggcccgg cccccgctcc tcccccgccg gcccggcccg gcccctcct tctcccgcc | 480 |
| ggcgctcgct gcctccccct cttccctctt cccacaccgc cctcagccgc tccctctcgt | 540 |
| acgcccgtct gaagaagaat cgagcgcgga acgcatcgat agctctgccc tctgcggccg | 600 |
| cccggccccg aactcatcgg tgtgctcgga gctcgatttt cctaggcggc | 650 |

<210> SEQ ID NO 18
<211> LENGTH: 500
<212> TYPE: DNA
<213> ORGANISM: Homo sapiens

<400> SEQUENCE: 18

| | |
|---|---|
| cggggtgctc ttcgcagctt ctctgtggag accggtcagc ggggcggcgt ggccgctcgc | 60 |
| ggcgtctccc tggtggcatc cgcacagccc gccgcggtcc ggtcccgctc cgggtcagaa | 120 |
| ttggcggctg cggggacagc cttgcggcta ggcaggggc gggccgccgc gtgggtccgg | 180 |
| cagtccctcc tcccgccaag gcgccgccca gacccgctct ccagccggcc cggctcgcca | 240 |
| ccctagaccg ccccagccac cccttcctcc gccggcccgg cccccgctcc tcccccgccg | 300 |
| gcccggcccg gcccctcct tctcccgcc ggcgctcgct gcctccccct cttccctctt | 360 |
| cccacaccgc cctcagccgc tccctctcgt acgcccgtct gaagaagaat cgagcgcgga | 420 |
| acgcatcgat agctctgccc tctgcggccg cccggccccg aactcatcgg tgtgctcgga | 480 |
| gctcgatttt cctaggcggc | 500 |

<210> SEQ ID NO 19
<211> LENGTH: 57
<212> TYPE: DNA
<213> ORGANISM: Homo sapiens

<400> SEQUENCE: 19

| | |
|---|---|
| tgtttattta catgcagtca atgatagtaa atggatgcgc gccagtatag gccgacc | 57 |

<210> SEQ ID NO 20
<211> LENGTH: 10

```
<212> TYPE: PRT
<213> ORGANISM: Homo sapiens

<400> SEQUENCE: 20

Pro Pro Pro Pro Leu Pro Gln Gln Pro Pro
1               5                   10
```

GASTRIC CARCINOMA GENE ZNF312B, A PROTEIN TRANSLATED FROM THE GENE, AND A DIAGNOSTIC KIT AND A SCREENING METHOD FOR ANTICANCER AGENTS USING THE SAME

TECHNICAL FIELD

The present invention relates to a diagnostic marker for stomach cancer containing a gastric carcinoma gene ZNF312b or fragments thereof, a diagnostic method for stomach cancer using the same, and a screening method for stomach cancer inducers or inhibitors using the marker.

BACKGROUND ART

Higher animals including human have approximately 30,000 genes. Among these genes, only about 15% are expressed in each individual. Therefore, every biological phenomenon, such as development, differentiation, homeostasis, response to stimulus, cell cycle regulation, aging and apoptosis (programmed cell death) is determined by what gene is chosen to be expressed (Liang, P. and A. B. Pardee, *Science*, 257: 967-971, 1992).

The pathological phenomenon such as tumorigenesis is caused by genetic mutation and at last induces changes in gene expression. This kind of genetic change causes abnormality of cell signaling system. Thus, comparison of gene expressions among different cells can be a basic, efficient approach for understanding various biological phenomena. According to the results of previous studies on tumorigenesis, various genetic changes such as loss of chromosomal heterozygosity, activation of oncogenes and inactivation of tumor suppressor genes including p53, are focused on tumor tissues to cause cancer in human (Bishop, J. M., *Cell*, 64:235-248, 1991, and Hunter, T., *Cell*, 64:249-270, 1991). 10-30% of cancer is presumably caused by activation of oncogenes resulted from amplification of the oncogenes. The activation of oncogenes becomes an important factor for the studies of etiology of cancer, so that it has been a major target of cancer studies.

Stomach cancer is the most frequent cancer in Asia including Korea and Japan, which has the highest death rate (Parkin et al, *Int. J. Cancer* 80: 827-841, 1999; Neugut et al, *Semin. Oncol.* 23: 281-291, 1996). A few genes involved in stomach cancer have been disclosed, so far.

However, it has been recently found out that such genes as p53 (Yokozaki et al, *Int. Rev. Cytol.* 204: 49-95, 2001), β-catenin (Park, et al, *Cancer Res.* 59: 4257-4260, 1999), E-cadherin (Berx et al, *Hum. Mutat.* 12: 226-237, 1998), trefoil factor 1 (Park et al, *Gastroenterology* 119: 691-698, 2000) and c-met (Lee et al, *Oncogene* 19: 4947-4953, 2000) demonstrate genetic changes in stomach cancer cases. It was also reported that CA11 (Yoshikawa et al, *Jpn. J. Cancer Res.* 91: 459-463, 2000; Shiozaki et al, *Int. J. Oncol.* 19: 701-707, 2001) and TFF1 and TFF2, the trefoil factors synthesized in mucous membrane of stomach (Shiozaki et al, *Int. J. Oncol.* 19: 701-707, 2001; Kirikoshi and KatohKirikoshi, *Int. J. Oncol.* 21: 655-659, 2002), were reduced in stomach cancer patients. Hasegawa et al confirmed by cDNA microarray using 23.040 genes expressed in colon type stomach cancer that the expressions of RPL10, HSPCB, LOC56287, IGHM, PGC, REGIA, RNASE1, TFF1 and TFF2 were related to metastasis of stomach cancer (Hasegawa et al, *Cancer Res.* 62: 7012-7017, 2002). However, diagnosis or treatment of stomach cancer with these genes alone is not enough and a specific target gene of stomach cancer has not been established, yet.

ZNF312b gene is also called as Fezf1 (forebrain embryonic zinc finger-like 1) gene, which was the first identified gene in olfactory sensory neuron (OSN) of the forebrain of Xenopus and has been known to encode a protein having zinc ions (Matsuo-Takasaki et al., *Mech. Dev.* 93: 201-204, 2000)). This gene is essential for proper termination of the olfactory nerve, formation of olfactory bulb and rostral stream migration of interneuron progenitor and is also an essential factor for cell-autonomously control of axonal projection and olfactory bulb membrane formation control (Tsutomu Hirata et al., *Development* 133: 1433-1443, 2006). The expression of ZNF312b is observed in the phase of embryo development, but is weak in an adult. The expression of ZNF312b is not observed in other tissues. A few reports about functions of ZNF312b gene have been known, but none of them is related to stomach cancer or cancer development.

The present inventors noticed the increase of the expression of ZNF312b in stomach cancer tissues. Therefore, the present inventors focused our study on the cancer development-related function of ZNF312b gene. As a result, the present inventors completed this invention by confirming that the ZNF312b gene expression was specifically increased in stomach cancer, suggesting that the gene had tumorigenesis related functions, acted as an essential factor for cell proliferation signaling system and increased K-ras expression by binding to the K-ras promoter.

DISCLOSURE

Technical Problem

It is an object of the present invention to provide 1) a genetic marker containing ZNF312b gene or its fragments for diagnosing and screening stomach cancer, 2) a protein marker containing ZNF312b protein or its fragments for diagnosing and screening stomach cancer, 3) a method for diagnosing stomach cancer, a method for screening stomach cancer inducers and a method for screening stomach cancer inhibitors using the same, and 4) a composition for the prevention and treatment of stomach cancer.

Technical Solution

To achieve the above object, the present invention provides a diagnostic kit for stomach cancer containing oligonucleotide with nucleotide sequences of ZNF312b gene represented by SEQ. ID. NO: 1 or the fragment thereof or a primer set capable of amplifying the oligonucleotide.

The present invention also provides a diagnostic kit for stomach cancer containing an antibody specifically binding to ZNF312b protein represented by SEQ. ID. NO: 2 or the fragment thereof.

The present invention further provides a diagnostic DNA microarray for stomach cancer in which oligonucleotide with nucleotide sequences of ZNF312b gene represented by SEQ. ID. NO: 1 or the fragment thereof or its complementary oligonucleotide is integrated.

The present invention also provides a screening method of a marker for stomach cancer containing the step of contacting an antibody specifically binding to ZNF312b protein represented by SEQ. ID. NO: 2 or the fragment thereof with biological samples selected from the group consisting of stomach tissues, stomach cells, urine, blood, serum and plasma.

The present invention also provides a diagnostic method for stomach cancer comprising the following steps:

1) measuring the expression level of the marker gene in samples of subjects; and
2) selecting the subject showing the higher marker expression, compared with the control group.

The present invention also provides a screening method for stomach cancer inducers or inhibitors comprising the following steps:

1) treating sample compositions or sample compounds to stomach originated cells (experimental group);
2) measuring and comparing the expression levels of the marker gene between the experimental group of step 1) and the non-treated control group; and
3) selecting the sample composition or the sample compound significantly increasing or decreasing the expression level of the marker gene in the experimental group, compared with the control group.

The present invention also provides a screening method for stomach cancer inducers or inhibitors comprising the following steps:

1) preparing a gene construct containing a reporter gene operably linked to ZNF312b promoter composed of nucleotide sequence represented by SEQ. ID. NO: 9 and the fragment thereof;
2) preparing a transformant by transfecting animal cell lines with the expression vector inserted with the gene construct of step 1);
3) preparing the experimental group by treating the transformant of step 2) with sample compositions or sample compounds and the control group by treating with nothing;
4) measuring the expression level of the reporter gene in the experimental group and in the control group of step 3); and
5) selecting the sample composition or the sample compound significantly increasing or decreasing the expression level of the gene in the experimental group, compared with the control group.

The present invention also provides a screening method for stomach cancer inducers or inhibitors comprising the following steps:

1) preparing a gene construct containing a reporter gene operably linked to the K-ras promoter composed of nucleotide sequence represented by SEQ. ID. NO: 15 and the fragment thereof;
2) preparing a transformant by transfecting animal cell lines expressing ZNF312b protein composed of amino acid sequence represented by SEQ. ID. NO: 2 or the fragment thereof with the expression vector inserted with the gene construct of step 1);
3) preparing the experimental group by treating the transformant of step 2) with sample compositions or sample compounds and the control group by treating with nothing;
4) measuring the expression level of the reporter gene in the experimental group and the control group of step 3); and
5) selecting the sample composition or the sample compound significantly increasing or decreasing the expression level of the gene in the experimental group of step 4), compared with the control group.

The present invention also provides a screening method for stomach cancer inducers or inhibitors comprising the following steps:

1) treating oligonucleotide containing K-ras promoter composed of nucleotide sequence represented by SEQ. ID. NO: 15 or the fragment thereof with ZNF312b protein containing amino acid sequence represented by SEQ. ID. NO: 2 or the fragment thereof together with a sample composition or a sample compound;

2) measuring and comparing the binding level of ZNF312b protein or the fragment thereof with K-ras promoter or the fragment thereof between the experimental group and the non-treated control group; and
3) selecting the sample composition or the sample compound significantly increasing or decreasing the binding level in the experimental group, compared with the control group.

The present invention also provides an animal model for diagnosing and screening stomach cancer in which stomach cancer is grafted by injection an animal skin except human with the vector containing ZNF312b gene represented by SEQ. ID. NO: 1 or the fragment thereof The present invention also provides an antisense gene with the complementary sequence to the full length or the part of mRNA transcribed from ZNF312b gene represented by SEQ. ID. NO: 1 or the fragment thereof and inhibiting the expression of ZNF312b gene or the fragment thereof by binding to the mRNA.

The present invention also provides a siRNA sequence with the complementary sequence to the full length or the part of mRNA transcribed from ZNF312b gene represented by SEQ. ID. NO: 1 or the fragment thereof and inhibiting the expression of ZNF312b gene or the fragment thereof by being recognized by Dicer protein.

The present invention also provides a composition for the prevention and treatment of stomach cancer containing the stomach cancer inhibitors screened by the above methods as an active ingredient.

The present invention also provides a method for the prevention and treatment of stomach cancer containing the step of administering a pharmaceutically effective dose of the composition for the prevention and treatment of stomach cancer to a subject.

In addition, the present invention provides a use of the stomach cancer inhibitors screened by the above methods for the preparation of a composition for the prevention and treatment of stomach cancer.

Hereinafter, terms used in this invention are described.

In this invention, "marker" is a material that facilitates distinguishment of stomach cancer cells from normal cells, which can be a nucleic acid marker for ZNF312b gene and a polypeptide marker for ZNF312b protein. These markers are characteristically over-expressed in stomach cancer cells, compared with in normal cells.

In this invention, 'diagnosis' indicates the confirmation of the presence or characteristics of stomach cancer.

In this invention, "gene expression level" indicates the expression level of mRNA of ZNF312b stomach cancer marker gene in a sample.

In this invention, "primer" indicates the nucleic acid sequence having a short free 3' hydroxyl group, which can form base pairs with a complementary template and can be functioning as an origin for replication of the template.

In this invention, "protein expression level" indicates the expression level of a protein translated from ZNF312b stomach cancer marker gene in a sample.

In this invention, "antibody" indicates an epitope-specific protein molecule.

Hereinafter, the present invention is described in detail.

The present invention provides a diagnostic kit for stomach cancer containing oligonucleotide with ZNF312b gene represented by SEQ. ID. NO: 1 (GeneBank Accession number: AY726588) or the fragment thereof or a primer set capable of amplifying the oligonucleotide.

ZNF312b gene fragment preferably contains carboxy-terminal region (SEQ. ID. NO: 20) of the nucleotide sequence represented by SEQ. ID. NO: 1, but not always limited thereto.

ZNF312b gene activates genes involved in cell proliferation by acting as a transcription regulator. The open reading frame corresponding to nucleotide #104 in the nucleotide sequence represented by SEQ. ID. NO: 1 is the full length protein encoding region, and the amino acid sequence translated from the ORF is represented by SEQ. ID. NO: 2 and composed of 475 amino acids (ZNF312b protein). However, considering degeneracy of codon or preferred codon to express the oncogene, the gene of the present invention can be modified in coding region as long as this modification does not affect the expression of the amino acids of the oncogenic protein, and besides, non-coding region can also be modified as long as it does not affect gene expression in the region. And this modified gene can be included in the criteria of the present invention. Therefore, the present invention includes a polynucleotide having the equal nucleotide sequence to that of the oncogene represented by SEQ. ID. NO: 1 and the fragment thereof. The equal 'polynucleotide' herein indicates the one having at least 80%, more preferably 90%, and most preferably at least 95% sequence homology.

To examine whether ZNF312b gene was over-expressed specifically in stomach cancer cells, the present inventors measured the expression of mRNA of ZNF312b gene in stomach cancer cell lines and clinical tissues. As a result, ZNF312b gene was over-expressed specifically in stomach cancer cells (see FIG. 1 and FIG. 2).

To investigate the effect of the expression of ZNF312b gene in stomach cancer cells, the present inventors constructed the expression vector with nucleotide sequences of ZNF312b gene and the expression vector for ZNF312b shRNA (small hairpin RNA). Stomach cancer cell line was transfected with the expression vectors. Then, changes in cell proliferation and cell cycle of the stomach cancer cell line were investigated. As a result, the over-expression of ZNF312b gene accelerated proliferation of the stomach cancer cell line, compared with in normal cells, decreased G1 stage of cell cycle but increased G2+M stage, resulting in the increase of cell growth rate. In the meantime, the inhibition of ZNF312b gene expression resulted in the decrease of cell proliferation in the stomach cancer cell line, increased G1 stage of cell cycle but reduced G2+M stage, and accordingly reduced cell growth rate (see FIGS. 3-11).

The present inventors also performed colony formation test and tumor formation experiment using nude mice to investigate the functions of ZNF312b as an oncogene. As a result, the over-expression of ZNF312b increased colony formation and significantly increased the size of tumor in the nude mice, compared with in the control (see FIGS. 12-17).

Therefore, ZNF312b gene of the present invention can be effectively used as a marker gene for diagnosis of stomach cancer.

The diagnostic kit for stomach cancer herein is to quantify ZNF312b mRNA for diagnosis and screening of stomach cancer, but not always limited thereto.

The diagnostic kit for stomach cancer herein preferably contains additional nucleotides represented by SEQ. ID. NO: 3 or NO: 4 specifically binding to ZNF312b mRNA, but not always limited thereto.

The diagnostic kit for stomach cancer herein preferably contains one or more additional components selected from the group consisting of primers for the production of cDNA corresponding to ZNF312b mRNA, reverse transcriptase, Taq polymerase, PCR primers and dNTP, but not always limited thereto.

The diagnostic kit for stomach cancer herein preferably contains a primer set capable of amplifying the marker gene, but not always limited thereto.

The primer is the nucleotides having a specific sequence to the nucleotide sequence of the marker gene, which is preferably composed of approximately 7-50 bp nucleotide sequence and more preferably 10-30 bp nucleotide sequence, but not always limited thereto.

The primer is capable of initiating DNA synthesis in the presence of PCR reagents, four different nucleotide triphosphates, at proper temperature with proper buffer. The primer can have additional characteristics as long as they do not change the basic characteristics of the primer acting as an origin of DNA replication.

The primer herein can be modified or chemically synthesized by phosphoramidite solid support method or other well known methods.

The diagnostic kit for stomach cancer can additionally contain one or more components selected from the group consisting of test tube, proper container, reaction buffer, dNTPs, Taq polymerase, reverse transcriptase, DNase, RNase inhibitor, DEPC water and sterilized water, but not always limited thereto.

The present invention also provides a diagnostic kit for stomach cancer containing an antibody specifically binding to ZNF312b protein represented by SEQ. ID. NO: 2 or the fragment thereof.

ZNF312b protein fragment preferably contains carboxy-terminal region of the amino acid sequence represented by SEQ. ID. NO: 2, but not always limited thereto.

To investigate the function of ZNF312b protein or the fragment thereof as a transcription factor and a target region for that function, the present inventors transfected a recombinant vector over-expressing the said protein or the fragment thereof into a stomach cancer cell line, followed by identification of the intracellular location by using nuclear fraction staining and immunocytochemistry. As a result, it was confirmed that ZNF312b protein or the fragment containing carboxy-terminal region of the protein (SEQ. ID. NO: 20) was translocated into nucleus (see FIGS. 18-20).

To investigate the effect of ZNF312b protein or the fragment thereof on cell proliferation and colony formation of a stomach cancer cell line, the present inventors transfected a recombinant vector over-expressing the protein or the fragment thereof into the stomach cancer cell line, followed by measuring the cell proliferation and colony formation. As a result, the over-expression of ZNF312b protein or the fragment thereof containing carboxy-terminal region increased cell proliferation and colony formation (see FIGS. 21-23).

To examine the cell proliferation signaling system in a stomach cancer cell line by ZNF312b protein or the fragment thereof, the present inventors transfected a over-expressing vector or siRNA for the ZNF312b or the fragment thereof into the stomach cancer cell line, followed by Western blotting using different antibodies. As a result, the reduction of ZNF312b and the fragment thereof resulted in the decrease of K-ras expression, suggesting the inactivation of ERK signaling system, while the over-expression of ZNF312b and the fragment thereof induced the activation of K-ras expression, indicating the activation of ERK signaling system (see FIGS. 24-25).

Therefore, ZNF312b protein and the fragment containing carboxy-terminal region of the protein (SEQ. ID. NO: 20) of the present invention can be used as a protein marker for diagnosis and screening of stomach cancer.

The kit preferably contains ZNF312b protein or the fragment thereof additionally, but not always limited thereto.

The antibody included in the kit is preferably a polyclonal antibody, a monoclonal antibody or a recombinant antibody, but not always limited thereto.

The antibody can be produced easily by the conventional method well known to those in the art. For example, the polyclonal antibody can be obtained by the procedure comprising the steps of injecting ZNF312b protein antigen into an animal; and taking blood sample from the animal to obtain serum containing the antibody against the antigen. At this time, the animal is selected from the group consisting of goat, rabbit, and pig, etc. The monoclonal antibody can be produced by hybridoma method (hybridoma method) (Kohler & Milstein, *European J. Immunology* 6:511-519, 1976) or phage antibody library technique (Clackson et al., *Nature*, 352:624-628, 1991; Marks et al, *J. Mol. Biol.*, 222:58, 1-597, 1991), well known to those in the art.

According to the hybridoma method, cells of an immunologically proper host animal such as a mouse injected with ZNF312b protein antigen and cancer or myeloma cell lines can be used. These two types of cells are fused according to the conventional method well known to those in the art, for example by using polyethylene glycol, and then antibody producing cells are proliferated by the standard tissue culture method. Homogenous cells are obtained by sub-cloning by limited dilution technique. Then, hybridoma capable of producing ZNF312b protein specific antibody is mass-cultured in vitro or in vivo by the standard technique.

According to the phage antibody library method, ZNF312b protein specific antibody gene is obtained, which is expressed as a fusion protein on the phage surface to construct an antibody library in vitro. Then, the monoclonal antibody specifically binding to ZNF312b protein is separated from the library.

The antibodies produced by the above methods can be separated by electrophoresis, dialysis, ion exchange chromatography, affinity chromatography, etc.

The antibody included in the kit of the present invention contains two full length light chains and two full length heavy chains and functional fragments of an antibody molecule as well. The functional fragment indicates a fragment retaining antigen binding capacity, which can be exemplified by Fab, F(ab'), F(ab')$_2$, F(ab)$_2$ and Fv, etc.

The kit is preferably for ELISA and can contain the control protein specific antibody in addition to the reagents for detecting antigen-antibody complex such as labeled secondary antibody, chromophore, antibody-conjugated enzyme and its substrate or other substances binding antibody.

The present invention further provides a diagnostic DNA microarray for stomach cancer in which oligonucleotide with the full length or the part of the marker gene nucleotide sequence or its complementary oligonucleotide is integrated.

The present invention also provides a screening method of a marker for stomach cancer containing the step of contacting an antibody specifically binding to ZNF312b protein represented by SEQ. ID. NO: 2 or the fragment thereof with biological samples selected from the group consisting of stomach tissues, stomach cells, urine, blood, serum and plasma.

Particularly, the screening method of a marker for stomach cancer is composed of the following steps:

1) contacting a biological sample with an antibody specifically binding to ZNF312b protein or the fragment thereof;

2) quantifying the antigen-antibody complex formed by the contact of step 1); and 3) selecting a marker by comparing the quantified level of step 2) with that of the control.

In the above method, the method for quantifying the antigen-antibody complex of step 2) is preferably selected from the group consisting of Western blotting, ELISA (enzyme linked immunosorbent assay), RIA (radioimmunoassay), radioimmunodiffusion, ouchterlony immunodiffusion, rocket immunoelectrophoresis, immunohistostaining, immunoprecipitation, complement fixation assay, FACS and protein chip, but not always limited thereto.

In this method, the amount of antigen-antibody complex of step 2) can be measured by detecting signal intensity. The detection can be performed by using one or more elements selected from the group consisting of enzyme, fluorescent material, ligand, luminescent material, microparticle, redox molecule and radio-isotope, but not always limited thereto.

The enzyme herein is preferably selected from the group consisting of β-glucuronidase, β-D-glucosidase, β-D-galactosidase, urease, peroxidase, alkaline phosphatase, acetylcoline esterase, glucose oxidase and hexokinase, but not always limited thereto. The fluorescent material herein is preferably selected from the group consisting of fluorescein, phycocyanin and fluorescamine, but not always limited thereto. The ligand is preferably biotin derivative, but not always limited thereto. The luminescent material is preferably luciferin, but not always limited thereto. The microparticle is preferably colloidal gold, but not always limited thereto. The redox molecule is preferably quinone, 1,4-benzoquinone or hydroquinone, but not always limited thereto. The radio-isotope is $^3$H or $^{14}$C, but not always limited thereto.

The present invention also provides a diagnostic method for stomach cancer comprising the following steps:

1) measuring the expression level of ZNF312b marker gene in samples of subjects; and 2) selecting the subject showing the higher marker expression, compared with the control group.

In the above method, the sample of step 1) is preferably selected from the group consisting of stomach tissues, stomach cells, urine, blood, serum and plasma, but not always limited thereto.

In the above method, the expression level of step 1) can be measured at mRNA level and protein level.

Measurement of the expression at mRNA level is preferably performed by the method such as RT-PCR, competitive RT-PCR, real time RT-PCR, RNase protection assay, Northern blotting and DNA chip, but not always limited thereto. By one of these methods, the expression of mRNA in a stomach cancer suspected patient can be compared with the expression of mRNA in the normal control group. That is, whether the stomach cancer suspected patient is a real stomach cancer patient or not can be diagnosed by measuring the expression of mRNA using ZNF312b gene marker, which means the stomach cancer can be diagnosed when the expression of mRNA is significantly increased.

Measurement of the expression at protein level is preferably performed by the method such as two-dimensional electrophoresis, protein chip, ELISA and a method using the marker protein specific antibody, but not always limited thereto.

The protein expression level can be measured by direct sandwich ELISA using a labeled antibody recognizing an antigen of the antibody-antigen complex fixed on a solid support, or indirect sandwich ELISA in which the antigen-antibody complex fixed on a solid support is reacted with another antibody recognizing the antigen of the antibody-antigen complex and then a labeled secondary antibody recognizing the above antibody is used. More preferably, the protein expression level can be measured by another sandwich ELISA, in which an antibody is fixed on a solid support and then reacted with a sample; a labeled antibody recognizing an antigen of the antibody-antigen complex is adhered thereon, followed by color development using an enzyme; or a labeled secondary antibody recognizing an antigen of the antibody-antigen complex is adhered thereon, followed by color development using an enzyme.

The expression level of the protein can be quantified by using a protein chip on which at least one of antibodies against ZNF312b protein marker is arranged and fixed at high density on the target area of a substrate. The method to analyze samples using a protein chip is composed of the following steps: isolating a protein from a sample; hybridizing the separated protein with a protein chip to form an antigen-antibody complex; and confirming the expression of the protein to diagnose stomach cancer.

The expression level of the protein can be quantified by Western blotting using an antibody against ZNF312b. Particularly, total proteins are isolated from a sample; the separated proteins proceed to electrophoresis to sort the proteins out according to sizes; and then the proteins are transferred to nitrocellulose membrane to react with an antibody. The generated antigen-antibody complex is quantified by using a labeled antibody, leading to the diagnosis of stomach cancer.

The present invention also provides a screening method for stomach cancer inducers comprising the following steps:

1) treating sample compositions or sample compounds to stomach originated cells (experimental group);

2) measuring and comparing the expression levels of ZNF312b marker gene with the nucleotide sequence represented by SEQ. ID. NO: 1 or the fragment thereof between the experimental group of step 1) and the non-treated control group; and 3) selecting the sample composition or the sample compound significantly increasing the expression level of the marker gene in the experimental group, compared with the control group.

In the above method, ZNF312b gene of step 2) preferably contains the nucleotide sequence represented by SEQ. ID. NO: 1 or the fragment thereof, and the fragment preferably contains carboxy-terminal region of the nucleotide sequence represented by SEQ. ID. NO: 1, but not always limited thereto.

In the above method, the measurement of the gene expression of step 2) can be performed by one of the methods selected from the group consisting of RT-PCR, competitive RT-PCR, real time RT-PCR, RNase protection assay, Northern blotting and DNA chip, but not always limited thereto. By one of these methods, the mRNA expressions are compared between the normal control and the experimental group. Stomach cancer inducers can be screened by detecting significant increase of the mRNA expression of ZNF312b gene marker.

The present invention also provides a screening method for stomach cancer inhibitors comprising the following steps:

1) treating sample compositions or sample compounds to stomach originated cells (experimental group);

2) measuring and comparing the expression levels of ZNF312b marker gene with the nucleotide sequence represented by SEQ. ID. NO: 1 or the fragment thereof between the experimental group of step 1) and the non-treated control group; and 3) selecting the sample composition or the sample compound significantly decreasing the expression level of the marker gene in the experimental group, compared with the control group.

In the above method, ZNF312b gene of step 2) preferably contains the nucleotide sequence represented by SEQ. ID. NO: 1 or the fragment thereof, and the fragment preferably contains carboxy-terminal region of the nucleotide sequence represented by SEQ. ID. NO: 1, but not always limited thereto.

In the above method, the measurement of the gene expression of step 2) can be performed by one of the methods selected from the group consisting of RT-PCR, competitive RT-PCR, real time RT-PCR, RNase protection assay, Northern blotting and DNA chip, but not always limited thereto. By one of these methods, the mRNA expressions are compared between the normal control and the experimental group. Stomach cancer inhibitors can be screened by detecting significant decrease of the mRNA expression of ZNF312b gene marker.

The present invention also provides a screening method for stomach cancer inducers comprising the following steps:

1) preparing a gene construct containing a reporter gene operably linked to ZNF312b promoter composed of nucleotide sequence represented by SEQ. ID. NO: 9 and the fragment thereof 2) preparing a transformant by transfecting animal cell lines with the expression vector inserted with the gene construct of step 1);

3) preparing the experimental group by treating the transformant of step 2) with sample compositions or sample compounds and the control group by treating with nothing;

4) measuring the expression levels of the reporter gene in the experimental group and the control group of step 3); and 5) selecting the sample composition or the sample compound significantly increasing the expression level of the gene in the experimental group of step 4), compared with the control group.

In the above method, the fragment of step 1) preferably contains a region of −850 bp~+1 bp (SEQ. ID. NO: 12) from the transcription start site in the nucleotide sequence represented by SEQ. ID. NO: 9, but not always limited thereto.

In the above method, the reporter gene of step 1) is luciferase gene, but not always limited thereto.

To establish a cell line and to select a region of ZNF312b promoter that exhibits high transcription activity, different fragments of the promoter were inserted into a vector encoding luciferase reporter gene, followed by transfection of a stomach cancer cell line with the vector. Then, the luciferase activity was investigated. As a result, a region having the highest transcription activity of ZNF312b promoter ranges from −850 bp to +1 bp (SEQ. ID. NO: 12) from the transcription start site. And, the transcription activity from the cell lines consistently expressing the vector was higher than that of the cell lines transiently expressing the vector.

The present invention also provides a screening method for stomach cancer inhibitors comprising the following steps:

1) preparing a gene construct containing a reporter gene operably linked to ZNF312b promoter composed of nucleotide sequence represented by SEQ. ID. NO: 9 and the fragment thereof 2) preparing a transformant by transfecting animal cell lines with the expression vector inserted with the gene construct of step 1);

3) preparing the experimental group by treating the transformant of step 2) with sample compositions or sample compounds and the control group by treating with nothing;

4) measuring the expression levels of the reporter gene in the experimental group and the control group of step 3); and 5) selecting the sample composition or the sample compound significantly decreasing the expression level of the gene in the experimental group of step 4), compared with the control group.

In the above method, the fragment of step 1) preferably contains a region of −850 bp~+1 bp (SEQ. ID. NO: 12) from the transcription start site in the nucleotide sequence represented by SEQ. ID. NO: 9, but not always limited thereto.

In the above method, the reporter gene of step 1) is luciferase gene, but not always limited thereto.

To screen a compound inhibiting transcription activity of ZNF312b promoter, the present inventors inserted ZNF312b promoter and the fragment thereof having the region of −850 bp~+1 bp (SEQ. ID. NO: 12) from the origin into a vector encoding luciferase reporter gene and exhibiting consistent transcription activity, and then transfected a stomach cancer cell line with the vector. The cell line was treated with different compounds, and inhibition of the luciferase reporter activity by those compounds was measured. As a result, approximately 50% of those compounds used for the experiment inhibited at least 40% of the luciferase reporter activity and approximately 60% of those inhibitor candidates demonstrated very low cytotoxicity of less than 10% (see Table 1 and Table 2).

Therefore, a compound inhibiting ZNF312b expression can be screened by examining the transcription activity of ZNF312b promoter.

The present invention also provides a screening method for stomach cancer inducers comprising the following steps:

1) preparing a gene construct containing a reporter gene operably linked to the K-ras promoter composed of nucleotide sequence represented by SEQ. ID. NO: 15 and the fragment thereof;

2) preparing a transformant by transfecting animal cell lines expressing ZNF312b protein composed of amino acid sequence represented by SEQ. ID. NO: 2 or the fragment thereof with the expression vector inserted with the gene construct of step 1);

3) preparing the experimental group by treating the transformant of step 2) with sample compositions or sample compounds and the control group by treating with nothing;

4) measuring the expression levels of the reporter gene in the experimental group and the control group of step 3); and 5) selecting the sample composition or the sample compound significantly increasing the expression level of the gene in the experimental group of step 4), compared with the control group.

In the above method, the fragment of K-ras promoter of step 1) preferably contains the nucleotide sequence represented by SEQ. ID. NO: 19, but not always limited thereto.

In the above method, the reporter gene of step 1) is luciferase gene, but not always limited thereto.

In the above method, ZNF312b fragment preferably contains carboxy-terminal region represented by SEQ. ID. NO: 20 of the amino acid sequence represented by SEQ. ID. NO: 2, but not always limited thereto.

In the above method, the fragment of ZNF312b of step 2) preferably contains carboxy-terminal region represented by sequence id.no.19 of the amino acid sequence represented by sequence id.no.2, but not always limited thereto.

The present invention also provides a screening method for stomach cancer inhibitors comprising the following steps:

1) preparing a gene construct containing a reporter gene operably linked to the K-ras promoter composed of nucleotide sequence represented by SEQ. ID. NO: 15 and the fragment thereof;

2) preparing a transformant by transfecting animal cell lines expressing ZNF312b protein composed of amino acid sequence represented by SEQ. ID. NO: 2 or the fragment thereof with the expression vector inserted with the gene construct of step 1);

3) preparing the experimental group by treating the transformant of step 2) with sample compositions or sample compounds and the control group by treating with nothing;

4) measuring the expression levels of the reporter gene in the experimental group and the control group of step 3); and 5) selecting the sample composition or the sample compound significantly decreasing the expression level of the gene in the experimental group of step 4), compared with the control group.

In the above method, the fragment of K-ras promoter of step 1) preferably contains the nucleotide sequence represented by SEQ. ID. NO: 19, but not always limited thereto.

In the above method, the reporter gene of step 1) is luciferase gene, but not always limited thereto.

In the above method, ZNF312b fragment preferably contains carboxy-terminal region represented by SEQ. ID. NO: 20 of the amino acid sequence represented by SEQ. ID. NO: 2, but not always limited thereto.

To explain the regulation mechanism of ZNF312b protein or the fragment thereof on the K-ras expression, the present inventors inserted K-ras promoter into a vector encoding luciferase reporter gene, and then transfected a stomach cancer cell line with the vector expressing ZNF312b protein or the fragment thereof, followed by measuring the luciferase activity. As a result, K-ras promoter was activated by the expression of ZNF312b protein or the fragment thereof.

To identify the active region of ZNF312b protein or the fragment thereof affecting K-ras promoter activity, the present inventors inserted different fragments of K-ras promoter into a vector encoding luciferase reporter gene, and then transfected a stomach cancer cell line with the vector expressing ZNF312b protein or the fragment thereof, followed by measuring the luciferase activity. Luciferase activity was measured. As a result, the active region of ZNF312b protein or the fragment thereof affecting K-ras promoter activity was identified the region of 57 bp represented by SEQ. ID. NO: 16.

Thus, stomach cancer inducers or inhibitors can be screened by analyzing an active region of ZNF312b protein or the fragment thereof, precisely by measuring the transcription activity of the region of 57 bp represented by SEQ. ID. NO: 19 of K-ras promoter.

The present invention also provides a screening method for stomach cancer inducers comprising the following steps:

1) treating oligonucleotide containing K-ras promoter composed of nucleotide sequence represented by SEQ. ID. NO: 15 or the fragment thereof with ZNF312b protein containing amino acid sequence represented by SEQ. ID. NO: 2 or the fragment thereof together with a sample composition or a sample compound;

2) measuring and comparing the binding level of ZNF312b protein or the fragment thereof with the K-ras promoter or the fragment thereof between the experimental group of step 1) and the non-treated control group; and 3) selecting the sample composition or the sample compound significantly increasing the binding level in the experimental group, compared with the control group.

In the above method, the fragment of K-ras promoter of step 1) preferably contains the nucleotide sequence represented by SEQ. ID. NO: 16, but not always limited thereto.

In the above method, ZNF312b fragment preferably contains carboxy-terminal region represented by SEQ. ID. NO:

20 of the amino acid sequence represented by SEQ. ID. NO: 2, but not always limited thereto.

In the above method, the measurement of step 2) is preferably performed by the method selected from the group consisting of two-dimensional electrophoresis, protein chip, ELISA and a method using the marker protein specific antibody, but not always limited thereto.

The present invention also provides a screening method for stomach cancer inhibitors comprising the following steps:

1) treating oligonucleotide containing K-ras promoter composed of nucleotide sequence represented by SEQ. ID. NO: 15 or the fragment thereof with ZNF312b protein containing amino acid sequence represented by SEQ. ID. NO: 2 or the fragment thereof together with a sample composition or a sample compound;

2) measuring and comparing the binding level of ZNF312b protein or the fragment thereof with the K-ras promoter or the fragment thereof between the experimental group of step 1) and the non-treated control group; and 3) selecting the sample composition or the sample compound significantly decreasing the binding level in the experimental group, compared with the control group.

In the above method, ZNF312b fragment of step 1) preferably contains carboxy-terminal region represented by SEQ. ID. NO: 20 of the amino acid sequence represented by SEQ. ID. NO: 2, but not always limited thereto.

In the above method, the measurement of step 2) is preferably performed by the method selected from the group consisting of two-dimensional electrophoresis, protein chip, ELISA and a method using the marker protein specific antibody, but not always limited thereto.

To confirm an active region of ZNF312b protein or the fragment thereof working on K-ras promoter, the present inventors performed investigation using DNA binding region assay kit. As a result, it was confirmed that ZNF312b protein and the fragment thereof were conjugated to the region of 57 bp represented by SEQ. ID. NO: 19 of K-ras promoter.

Thus, stomach cancer inducers or inhibitors can be screened by analyzing an active region of ZNF312b protein or the fragment thereof, precisely by measuring the binding level of ZNF312b protein or the fragment thereof to the region of 57 bp represented by SEQ. ID. NO: 19 of K-ras promoter.

The present invention also provides an animal model for diagnosing and screening stomach cancer in which which animal model is constructed by injection an animal embryo except human with the vector containing ZNF312b gene represented by SEQ. ID. NO: 1 or the fragment thereof The transgenic animal can be prepared by introducing ZNF312b gene or the fragment thereof of the present invention into a mammal, for example a rodent like a mouse, etc. At this time, it is preferred to inject the gene in the stage before 8-cell embryo. The transgenic animal can be effectively used for the screening of carcinogens, inhibitors of the gene and anticancer agents.

The present invention also provides a composition for the prevention and treatment of stomach cancer containing the stomach cancer inhibitor screened by the above methods as an active ingredient.

The anticancer agent herein preferably contains a complementary sequence to the total length or the part of mRNA transcribed from ZNF312b gene represented by SEQ. ID. NO: 1 or the fragment thereof, and an anti-sense gene inhibiting the expression of ZNF312b gene or the fragment thereof by combining with the mRNA, but not always limited thereto. The anti-sense gene is supposed to bind to the mRNA so as to introduce DNA sequence harboring the sequence capable of inhibiting translation by ribosome to treat stomach cancer caused by ZNF312b gene expression.

The stomach cancer inhibitor herein preferably contains a complementary sequence to the total length or the part of mRNA transcribed from ZNF312b gene or the fragment thereof and siRNA inhibiting the expression of ZNF312b gene or the fragment thereof by the recognition by Dicer protein, but not always limited thereto. The siRNA is transfected as a RNA fragment of 21-30 nucleotides and then recognized by Dicer, resulting in the degradation of mRNA of the gene, suggesting inhibition of the expression of the gene.

The composition for the prevention and treatment of stomach cancer of the present invention can include one or more pharmaceutically acceptable carriers in addition to an active ingredient selected among the stomach cancer inhibitors, such as saline, sterilized water, Ringer's solution, buffered saline, dextrose solution, maltodextrin solution, glycerol, ethanol, liposome and a mixture comprising one or more of those components. If necessary, a general additive such as an antioxidant and buffer can be additionally added. The composition of the present invention can be formulated in different forms including aqueous solutions, suspensions and emulsions for injection, pills, capsules, granules or tablets by mixing with diluents, dispersing agents, surfactants, binders and lubricants. A target organ specific antibody or other ligands can be mixed with one of the said carriers to be delivered to the target organ. The composition can further be prepared in suitable forms according to ingredients by following the method represented in Remington's Pharmaceutical Science (the newest edition), Mack Publishing Company, Easton Pa.

The present invention also provides a method for treating stomach cancer containing the step of administering a pharmaceutically effective dose of the composition for the prevention and treatment of stomach cancer to a subject.

The present invention also provides a method for preventing stomach cancer containing the step of administering a pharmaceutically effective dose of the composition for the prevention and treatment of stomach cancer to a subject.

The composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage is 0.1~100 mg/kg per day and preferably 0.5~10 mg/kg per day, and administration frequency is once a day or preferably a few times a day.

Among the treatment methods using the composition of the present invention, gene therapy using siRNA or antisense is accomplished by administering the composition to a subject by the conventional method to inhibit the oncogene expression. For example, antisense oligodeoxynucleotide (ODN) is mixed with poly-L-lysine derivatives by electrostatic interactions according to the method of J. S. Kim et al. (J. S. Kim et al., *J. Controlled Release*, 53, 175-182 (1998)) and this mixture is administered to a subject by intravenous injection.

Advantageous Effect

ZNF312b, the novel marker for diagnosis and treatment of stomach cancer of the present invention is over-expressed in a stomach cancer patient. Cell proliferation and tumor formation capacity of a stomach cancer cell line is activated by the over-expression of the gene. In the meantime, cell proliferation and tumor formation capacity is suppressed by the under-expression of the gene. Therefore, ZNF312b can be effectively used for diagnosis of stomach cancer, construction of a stomach cancer animal model, prevention and treatment of stomach cancer and development of a stomach cancer specific anticancer agent.

DESCRIPTION OF DRAWINGS

The application of the preferred embodiments of the present invention is best understood with reference to the accompanying drawings, wherein:

FIG. 5 is a diagram illustrating the cell proliferation of the stomach cancer cell line SNU668 after introducing si-ZNF312b-1 oligomer therein, FIG. 6 is a diagram illustrating the cell proliferation of SNU668-shZNF312b, the cell line in which ZNF312b expression is suppressed, FIG. 7 and FIG. 8 are diagrams illustrating the cell proliferations of SNU638-ZNF312b and SNU668-ZNF312b, the cell lines over-expressing ZNF312b. Significance test was performed to confirm the reliability of the test results. * $P \leq 0.05$: 95% reliability; ** $P \leq 0.05$: 99% reliability; $P \leq 0.01$: 99.9% reliability.

FIG. 9 and FIG. 10 are diagrams illustrating the cell cycle of the stomach cancer cell line SNU668 after introducing si-ZNF312b-1 therein. In these diagrams, cell cycle was investigated by flow cytometry and the analyzed cell cycle was calculated as cell proliferation rate (cell numbers of G2+M+S/total cell number×100) which is presented as the graph below.

FIG. 11 is a diagram illustrating the cell cycles of SNU638-ZNF312b and SNU668-ZNF312b, the cell lines over-expressing ZNF312b.

FIG. 12 and FIG. 13 are diagrams illustrating the colony formation of ZNF312b suppressed cell line SNU668-shZNF312b, and FIG. 14 and FIG. 15 are diagrams illustrating the colony formations of SNU638-ZNF312b and SNU668-ZNF312b, the cell lines over-expressing ZNF312b.

FIG. 18 is a schematic diagram illustrating the deletion mutation of ZNF312b protein, and FIG. 19 is a diagram illustrating the result of Western blotting with each protein, performed after separating cytoplasm and nucleus by nuclear fractionation to investigate translocation of each ZNF312b fragment into nucleus.

FIG. 20 is a diagram illustrating the intracellular location of ZNF312b obtained by nuclear fractionation, identified by immunostaining.

FIG. 21 is a diagram illustrating the cell proliferations, measured by using CCK-8 reagent, of the control (pHA), the cells over-expressing full length ZNF312b (FL), the cells over-expressing ZNF312b fragment containing amino-terminal (N1) and the cells over-expressing ZNF312b fragment containing carboxyl-terminal (C1) containing carboxy-terminal.

FIG. 22 is a diagram illustrating the result of the experiment performed by the same manner as described in FIG. 21 with the cell line established to express constantly the DNA.

FIG. 23 is a diagram illustrating the result of colony formation test performed using the cell line of FIG. 8b, in which colony formation efficiency was measured by using soft-agar.

FIG. 24 is a diagram illustrating the result of Western blotting. Particularly, the intracellular expression of ZNF312b was reduced by ZNF312b siRNA and then the level of RAS protein and the activation of RAS-ERK pathway were measured by Western blotting.

FIG. 25 is a diagram illustrating whether the temporary increase of ZNF312b or ZNF312b fragment containing C-terminal could increase the level of RAS protein and the activation level of ERK pathway.

FIG. 33 is a diagram illustrating that the expected ZNF binding region of K-ras promoter was directly interacted to ZNF312b protein to confirm that ZNF312b was actually interacted to the expected ZNF binding region in −650 bp~−500 bp of K-ras promoter.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Tumor Cell Culture and Total RNA Extraction

<1-1> Tumor Cell Culture

The present inventors cultured SNU-638 and SNU-668, the cell lines established from Korean stomach cancer patients in 1982, distributed from Korean Cell line Bank. The cell lines were maintained in RPMI-1640 (Hyclone, USA) supplemented with 10% FBS, 100 mg/ml of streptomycin and 100 IU/ml of ampicillin.

<1-2> Total RNA Extraction

Total RNA was extracted from stomach cancer patient tissues using RNeasy Total RNA kit (Qiagen Inc., Germany). To eliminate DNA contaminant, DNase (Promega, USA) was used. The total RNA was purified by phenol-chloroform method.

Example 2

Reverse Transcriptase-PCR

Figure 1:
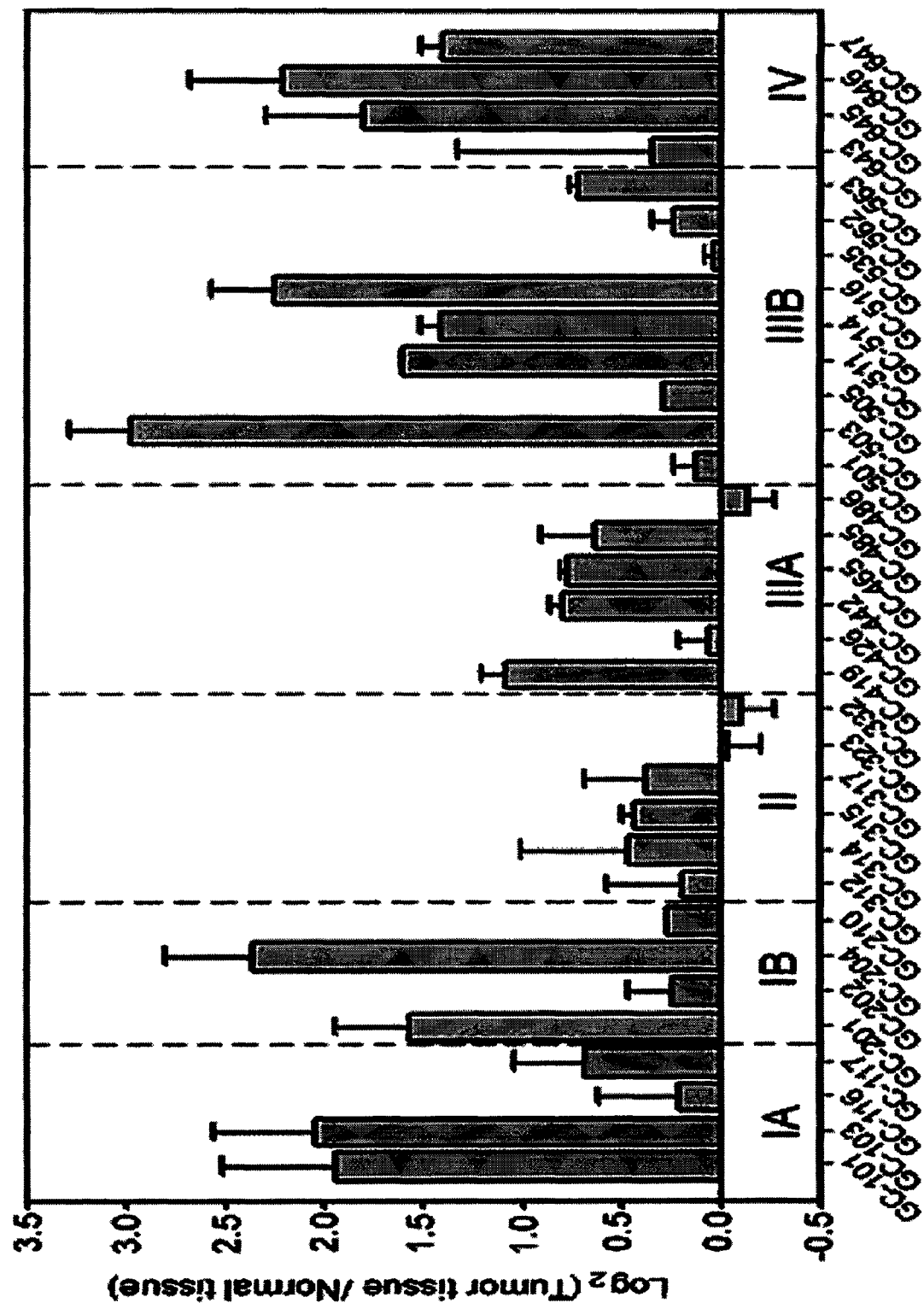
FIG. 1 and FIG. 2 are diagrams illustrating the results of real time RT-PCR with ZNF312b gene using total RNA extracted from patients with stomach cancer.
Figure 2:
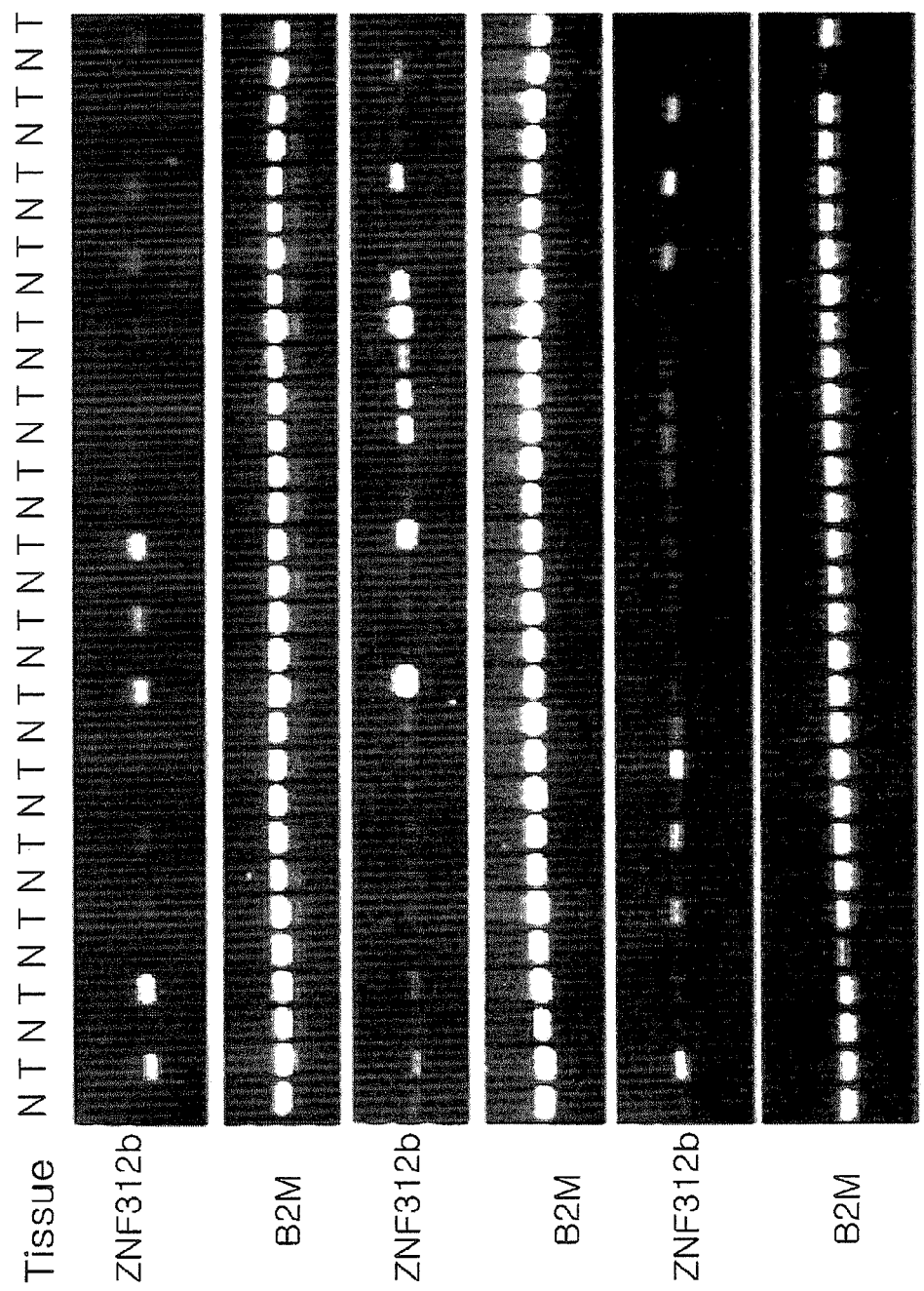

The present inventors performed reverse transcriptase PCR with 1/μg of the total RNA obtained in Example <1-2> using oligo dT primer. The generated cDNA was diluted 1/20, and 2 μl of the diluted cDNA was used as a template for PCR performed with ZNF312b primers [forward: 5'-CGAAGT-GTGTGGAAAGGT-3' (SEQ. ID. NO: 3), reverse: 5'-AATA-CACGCGGGCTACAAAC-3' (SEQ. ID. NO: 4)]. The PCR was performed as follows: at 94° C. for 45 seconds, at 58° C. for 45 seconds and at 72° C. for 45 seconds (35 cycles) and then final extension for 7 minutes. The amplified product was electrophoresed on 1.2% agarose gel, followed by staining with EtBr. The product was UV-irradiated, followed by analysis with image analyzer. The results were quantified by image analysis. B2M was used for the control and the differences among samples were corrected. FIG. 2 illustrates the expression of ZNF312b in stomach cancer patient tissues, and the result was quantified and shown in FIG. 1. As shown in FIG. 1, ZNF312b was excessively over-expressed in stomach cancer tissues (FIG. 1 and FIG. 2).

Example 3

Construction of ZNF312b Expression or Suppression Vector

<3-1> Construction of ZNF312b Expression Vector

The present inventors cloned ZNF312b gene into pcDNA vector. First, PCR was performed using the total cDNA as a template with ZNF312b primers containing KpnI and BamHI restriction enzyme sites. The PCR product was purified and digested with KpnI and BamHI, which was inserted into pcDNA vector to construct pcDNA-ZNF312b expression vector.

<3-2> ZNF312b Suppression Vector

To construct a vector expressing ZNF312b shRNA, si-ZNF312b-1 oligomer [5'-GCA CTC TCT GCA TCT CAA C-3' (SEQ. ID. NO: 5)] containing ZNF312b shRNA sequence was inserted into pSilencer4.1-CMVneo (Ambion, USA). As a result, pSilent-ZNF312b vector was constructed.

Example 4

Establishment of Transfected Stomach Cancer Cell Lines

<4-1> Establishment of Stomach Cancer Cell Line Over-Expressing ZNF312b

ZNF312b over-expressing cell lines SNU638-ZNF312b and SNU668-ZNF312b were established by transfecting the stomach cancer cell lines SNU-638 and SNU-668 with pcDNA-ZNF312b vector constructed in Example <3-1>.

First, to establish ZNF312b over-expressing cell lines, SNU-638 and SNU-668 cells were transfected with pcDNA-ZNF312b respectively using Fugene-6 (Roche, Germany). To select only those cells expressing the gene, 600 μg/ml of G418, the selection marker, was added to the culture solution. Colonies were separated to obtain the cell line containing a single clone. G418 containing medium was replaced every three days. Colonies formed therein were separated and cell numbers were increased, and some of which were used for the extraction of RNA or protein to investigate the gene expression and the rest was stored as frozen.

<4-2> Establishment of Stomach Cancer Cell Line Reppressing ZNF312b

ZNF312b knock-downed cell line SNU668-shZNF312b was established by transfecting the stomach cancer cell line SNU-638 with pSilent-ZNF312b vector constructed in Example <3-2>.

First, to establish ZNF312b knock-downed cell line, SNU-668 cells were transfected with pSilent-ZNF312b using Fugene-6 (Roche, Germany). To select only those cells expressing the gene, 600 μg/ml of G418, the selection marker, was added to the culture solution. Colonies were separated to obtain the cell line containing a single clone. G418 containing medium was replaced every three days. Colonies formed therein were separated and cell numbers were increased, and some of which were used for the extraction of RNA or protein to investigate the gene expression and the rest was stored as frozen. The cell line confirmed to reppress the said gene was mass-cultured, which was stored as frozen or used for the examination of the functions of the gene.

Example 5

Western Blotting

The present inventors performed Western blotting to evaluate the protein expression of the vector constructed in Example 4.

First, lysis buffer A [20 mM HEPES (pH7.5), 150 mM NaCl, 1 mM EDTA, 2 mM EGTA, 1% Triton X-100, 10% glycerol, protease cocktail I, II (Sigma, USA)] was added to the cells, which stood at 4° C. for 20 minutes. The cell lysate was transferred into a new tube, followed by centrifugation at 4° C. at 15,000 rpm for 10 minutes to obtain protein. The cell lysate was heated at 95° C. for 10 minutes after adding 5× sample buffer, resulting in gel loading sample which proceeded to SDS PAGE gel electrophoresis. The protein bands separated according to their molecular weights by the above electrophoresis were transferred onto nitrocellulose membrane by using transfer kit (Bio-Rad, USA), followed by blocking for one hour with 5% skim milk. Next, each antibody [HA antibody for the detection of ZNF312b, and tubulin antibody for the detection of the control tubulin] was treated thereto at 4° C. for 12 hours. The membrane was washed with TBST buffer (0.2% Tween 20), and then treated with a secondary antibody for 1 hour. The membrane was washed with TBST and developed using HRP detection kit (AB frontier, Korea).

Example 6

Cell Proliferation Test

<6-1> Cell Proliferation by Inhibition of ZNF312b Gene Expression

Figure 3:
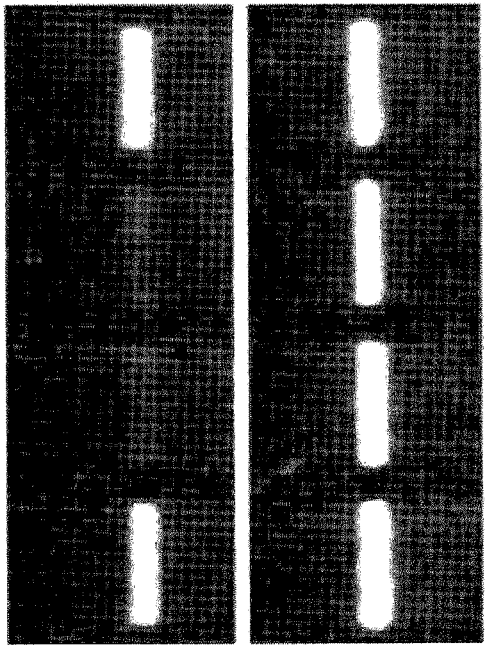
FIG. 3 and FIG. 4 are diagrams illustrating the expression of ZNF312b gene in the stomach cancer cell line SNU668-shZNF312b (FIG. 4) transfected with the vector shZNF312b constructed by using ZNF312b siRNA (FIG. 3) and si-ZNF312b-1 sequence of the said siRNA.
Figure 4:
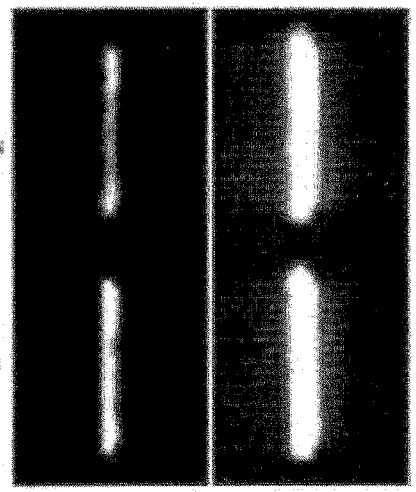

To investigate the cell proliferation capacity of the stomach cancer cell line after inhibiting the expression of ZNF312b gene, three kinds of siRNAs [si-ZNF312b-1: 5'-GCA CTC TCT GCA TCT CAA C-3' (SEQ. ID. NO: 6), si-ZNF312b-2: 5'-GTG TGT GGA AAG GTC TTT A-3' (SEQ. ID. NO: 7), and si-ZNF312b-3': 5'-GCA GTT CAA GTG CAA TAT C-3' (SEQ. ID. NO: 8)] comprising 19 nucleotides of ZNF312b nucleotide sequence (SEQ. ID. NO: 1) were constructed, which were used for the investigation of ZNF312b gene expression inhibition. As a result, as shown in FIG. 3, si-ZNF312b-1 demonstrated the highest inhibition activity, so that it was used for the experiment of transiently inhibition of ZNF312b expression (FIG. 3).

Figure 5:
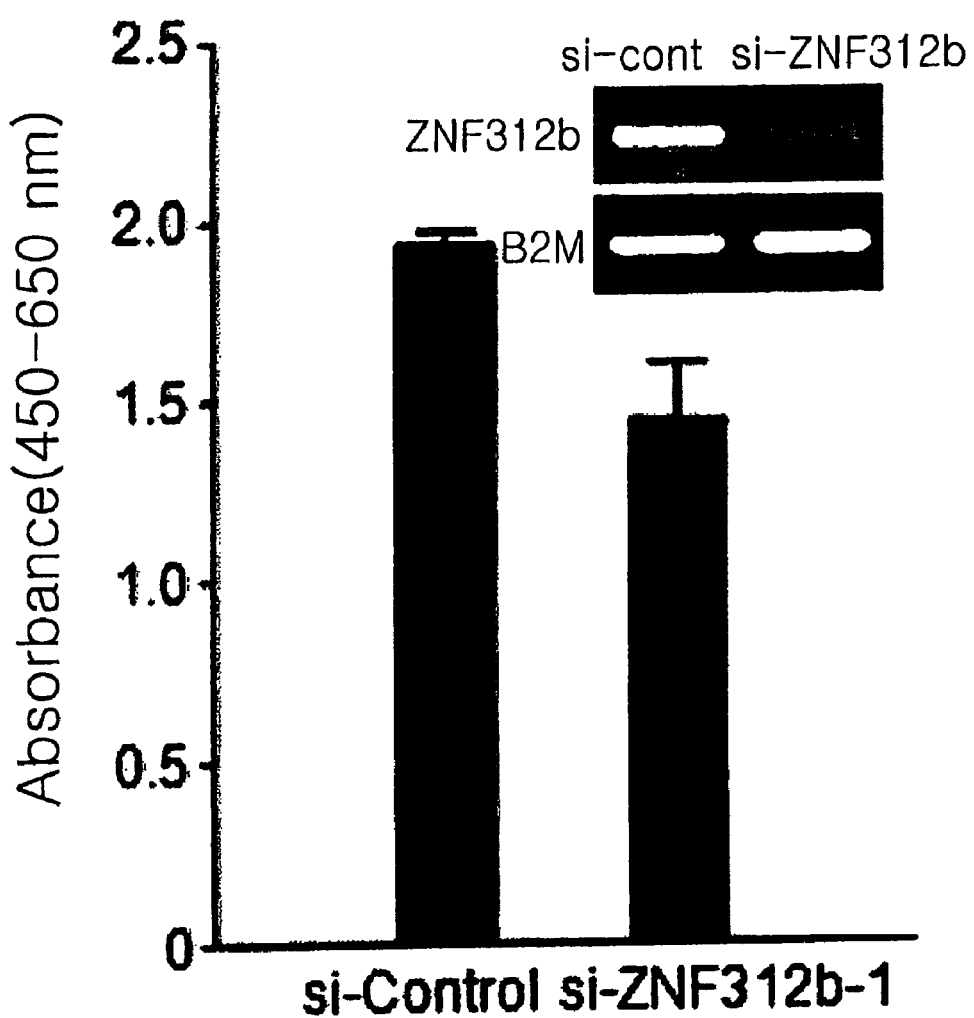
FIG. 5-FIG. 8 are diagrams illustrating the cell proliferation with ZNF312b gene.
Figure 6:
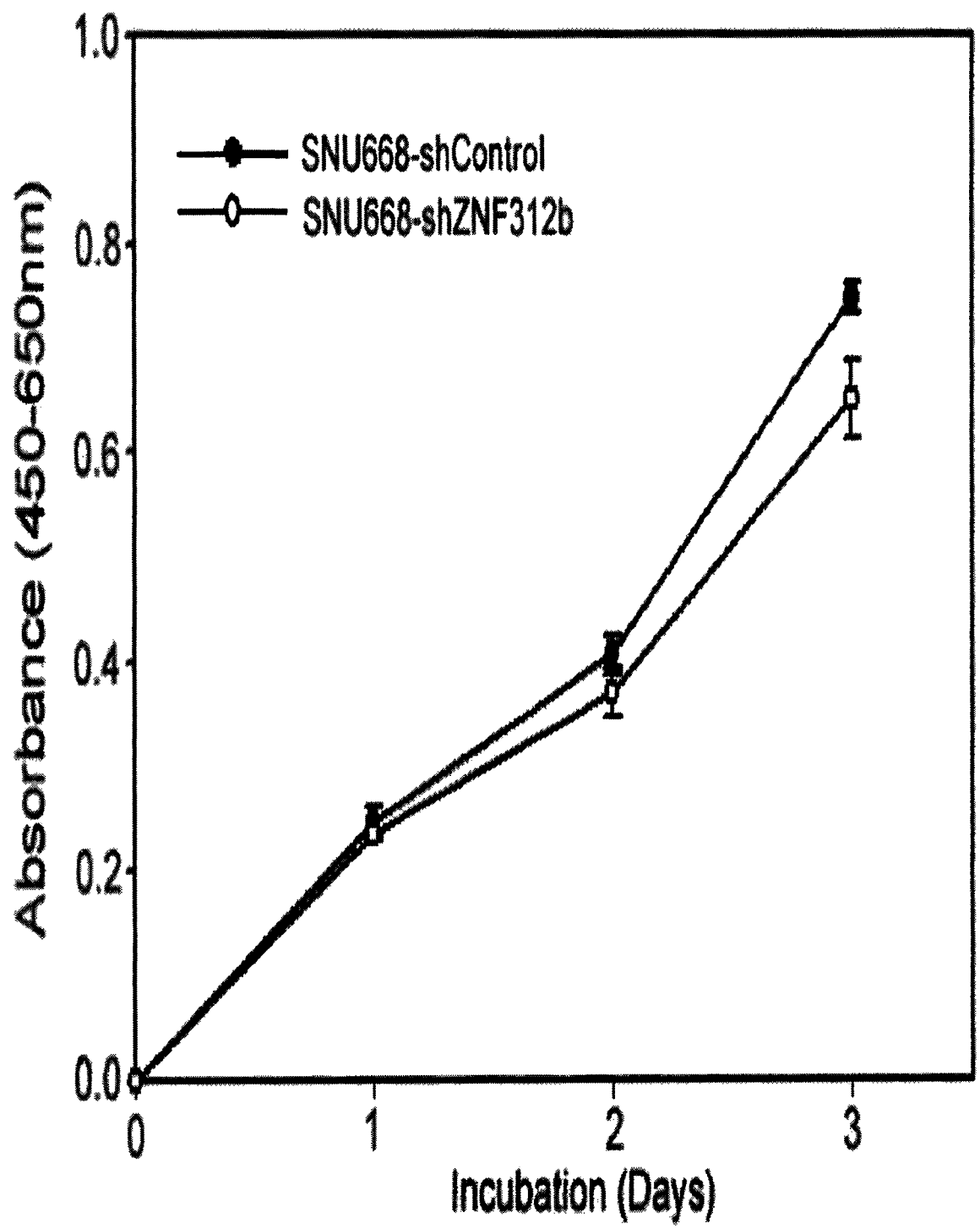

To induce constant inhibition of the said gene, total RNA was extracted from the SNU668-shZNF312b cell line prepared in Example <3-2> and the expression level was measured. As a result, ZNF312b gene expression was inhibited, so that it was used for the experiment of constant inhibition of ZNF312b gene expression. For the cell proliferation experiment, CCK-8 reagent (Dojindo, Japan) was used. Particularly, this method is to evaluate cell proliferation by measuring the conversion into hydrophilic formazan by intracellular dehydrogenase using tetrazolium salt. FIG. 5 illustrates that the cell proliferation was inhibited by transiently inhibition of ZNF312b gene expression. Diagram in the graph indicates ZNF312b inhibition level, confirmed by RT-PCR. FIG. 6 illustrates that the cell proliferation of the cells in which ZNF312b gene expression was constantly inhibited, was reduced, compared with the control (FIG. 5 and FIG. 6).

<6-1> Cell Proliferation by Over-Expression of ZNF312b Gene Expression

Figure 7:
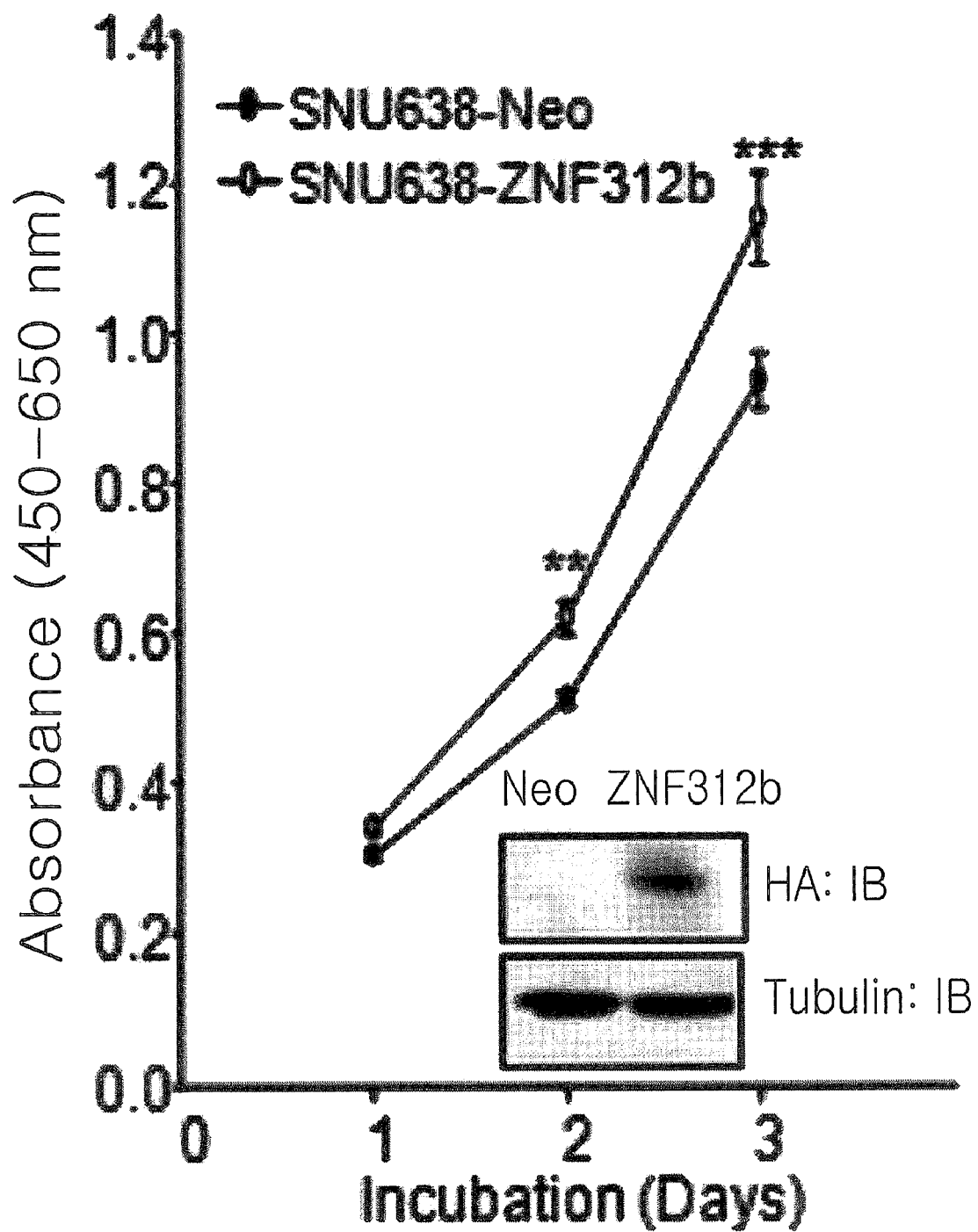
Figure 8:
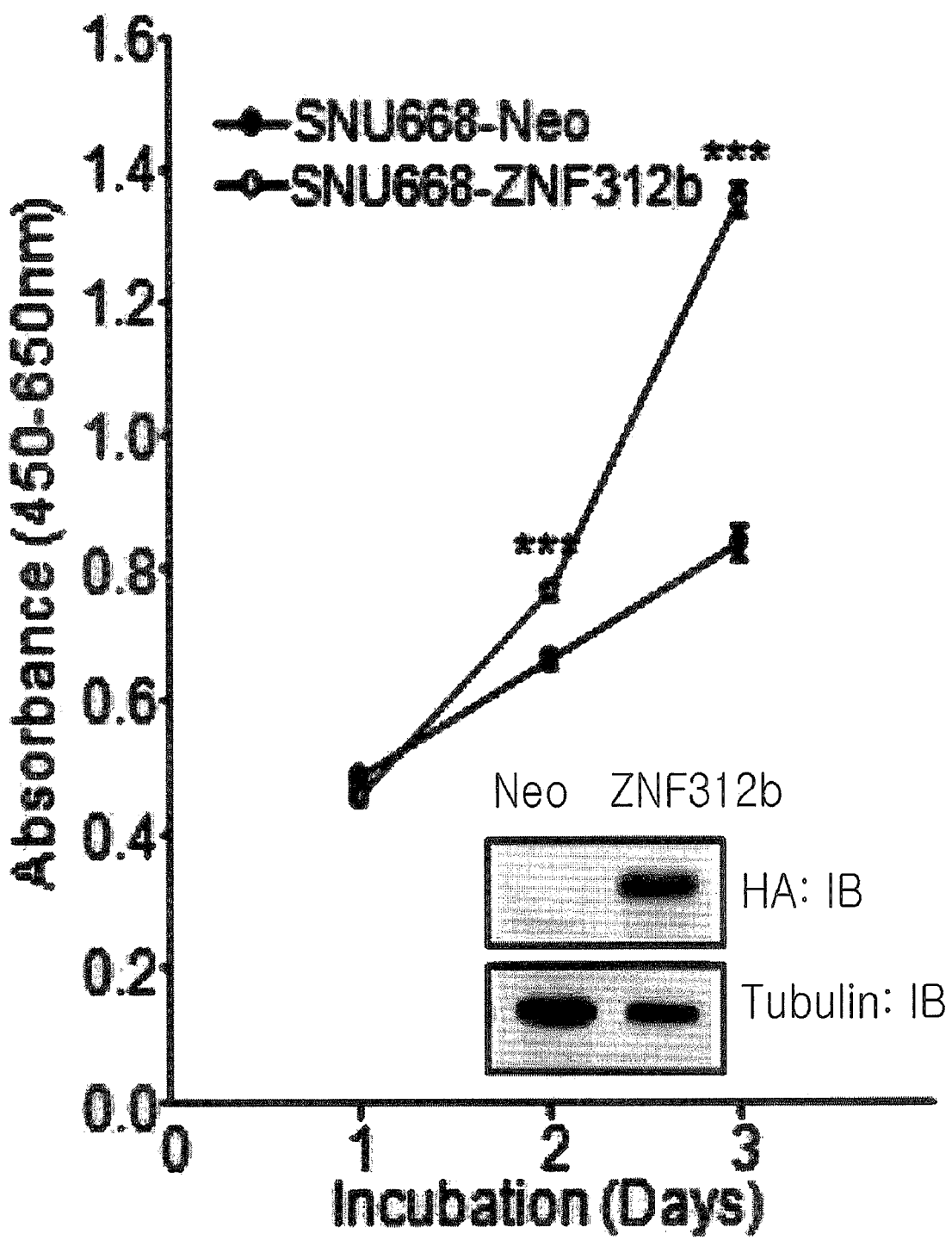

The present inventors investigated the cell proliferation capacity of the stomach cancer cell line after over-expressing the said gene, for which SNU638-ZNF312b and SNU668-ZNF312b, the cell lines established in Example 4, were used. For the cell proliferation experiment, CCK-8 reagent was used. Particularly, the cells ($5 \times 10^3$) were inoculated in a 96-well plate, followed by culture for 24 hours. Cell proliferation was measured every 24 hours. FIG. 7 illustrates the cell proliferation of SNU638-ZNF312b and FIG. 8 illustrates the cell proliferation of SNU668-ZNF312b. Diagram in the graph illustrates the result of Western blotting examining the over-expression of HA-ZNF312b, suggesting that the over-expression of the gene increased the cell proliferation (FIGS. 7 and 8).

Example 7

Cell Cycle Experiment

Figure 9:
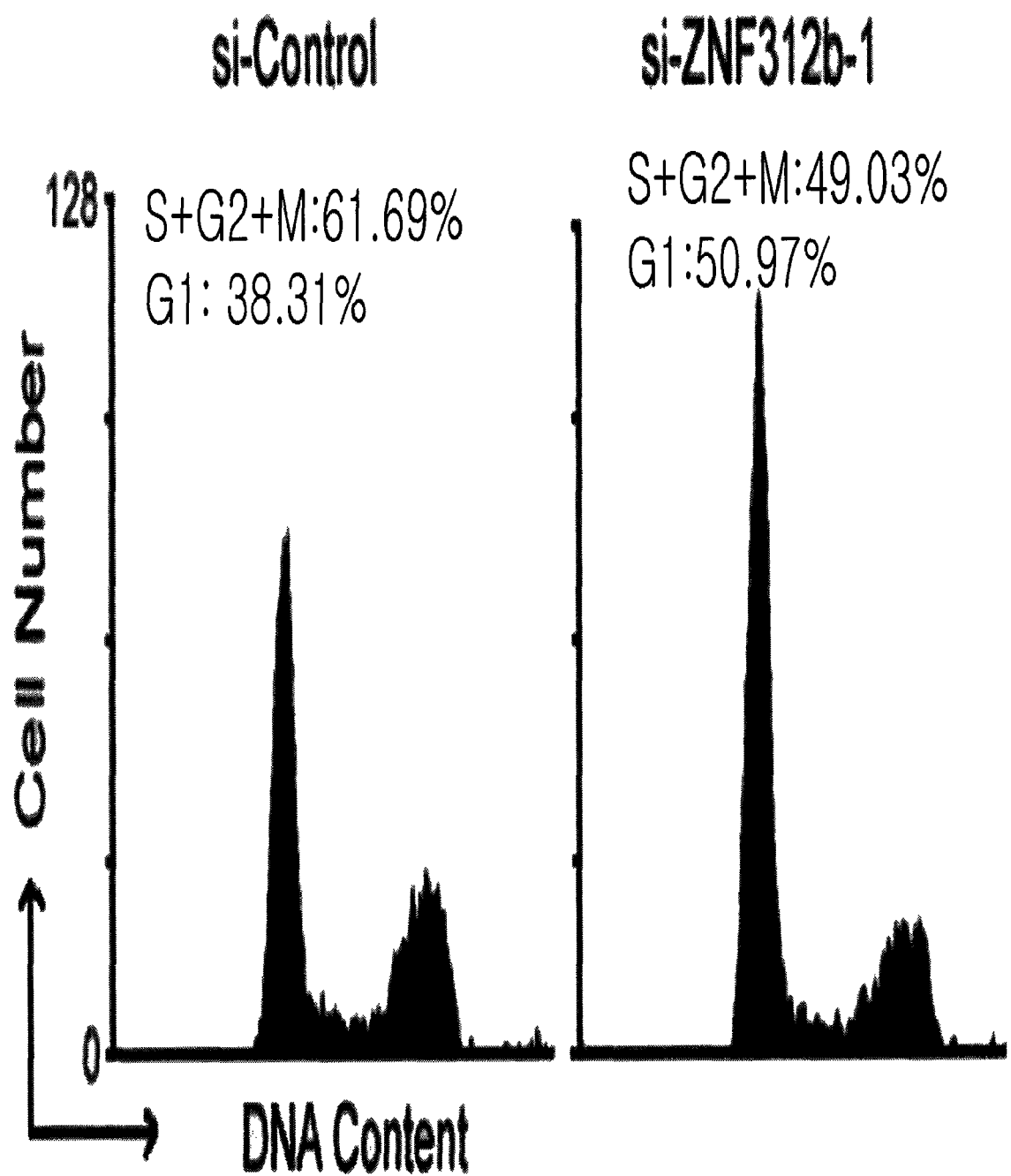
FIG. 9-FIG. 11 are diagrams illustrating the results of cell cycle experiments with ZNF312b gene. DNA was stained by PI, which proceeded to flow cytometry.
Figure 10:
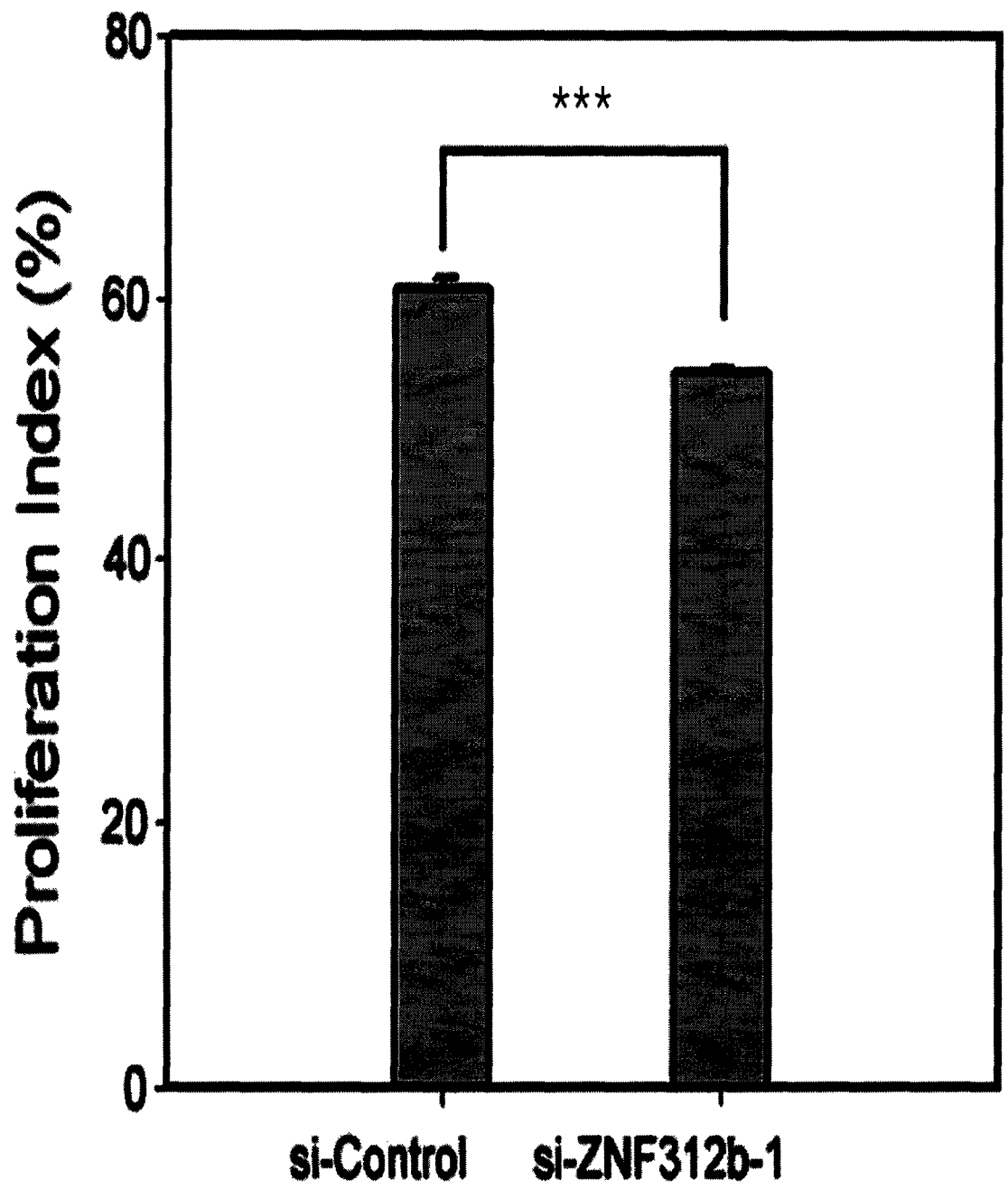
Figure 11:
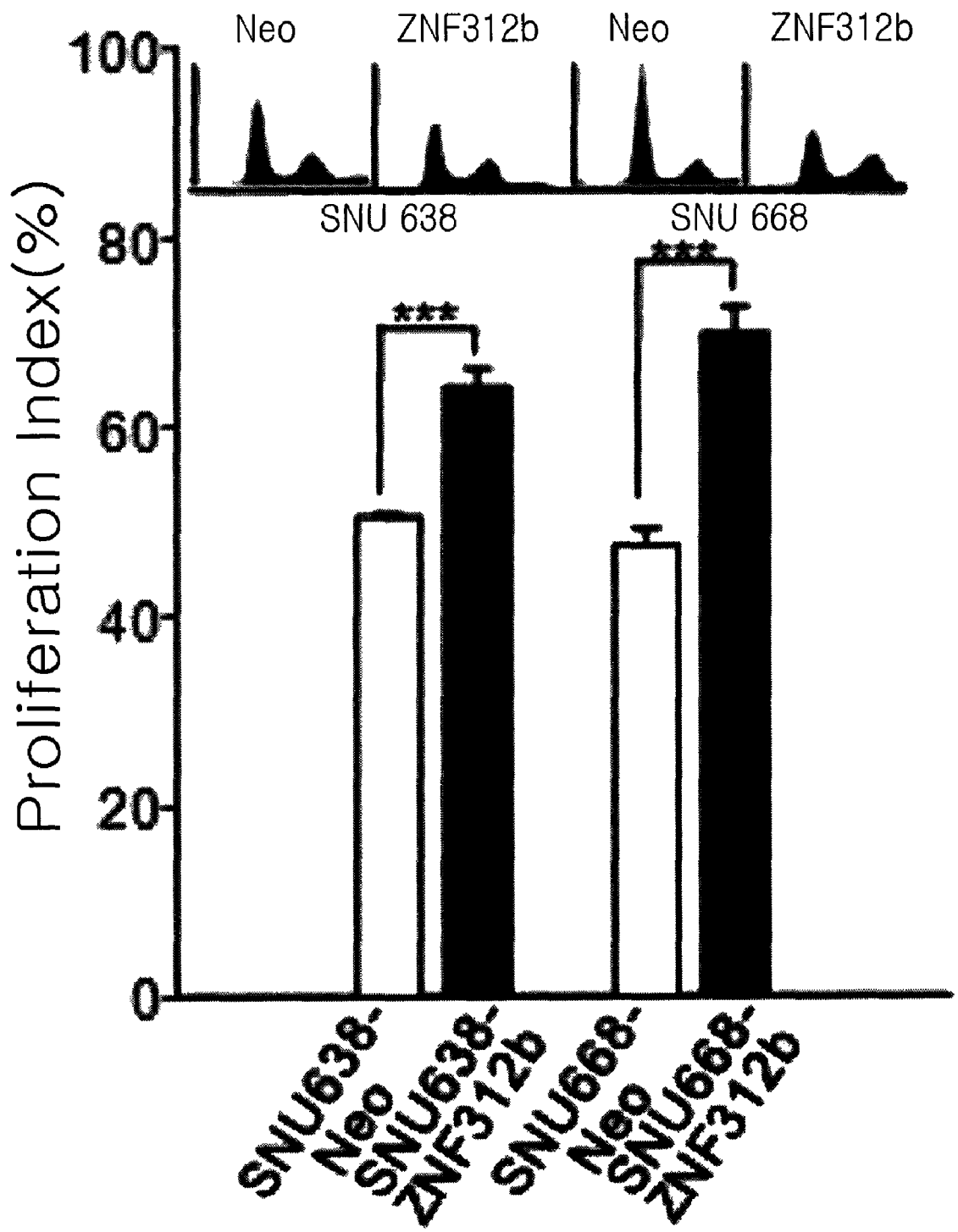

The present inventors investigated the involvement of ZNF312b gene in cell proliferation by measuring cell cycle. Cell cycle experiment was performed by PI staining method. Particularly, each cell was cultured for 24 hours and then fixed in 70% ethanol at 4° C. for at least 12 hours, followed by staining with PI. Cell cycle was measured by FACS. As a result, as shown in FIGS. 9-11, when ZNF312b expression was inhibited, G1 stage was extended but G2+M was reduced, indicating decrease of the cell proliferation. On the contrary, when ZNF312b was over-expression, G1 stage was reduced but G2+M was extended, indicating increase of the cell proliferation. The experiment examining the cell proliferation by measuring cell cycle also confirmed that the cell proliferation could be induced or inhibited by the inhibition or over-expression of ZNF312b gene, indicating the gene is involved in the cell proliferation (FIGS. 9, 10 and 11).

Example 8

Colony Forming Assay

Figure 12:
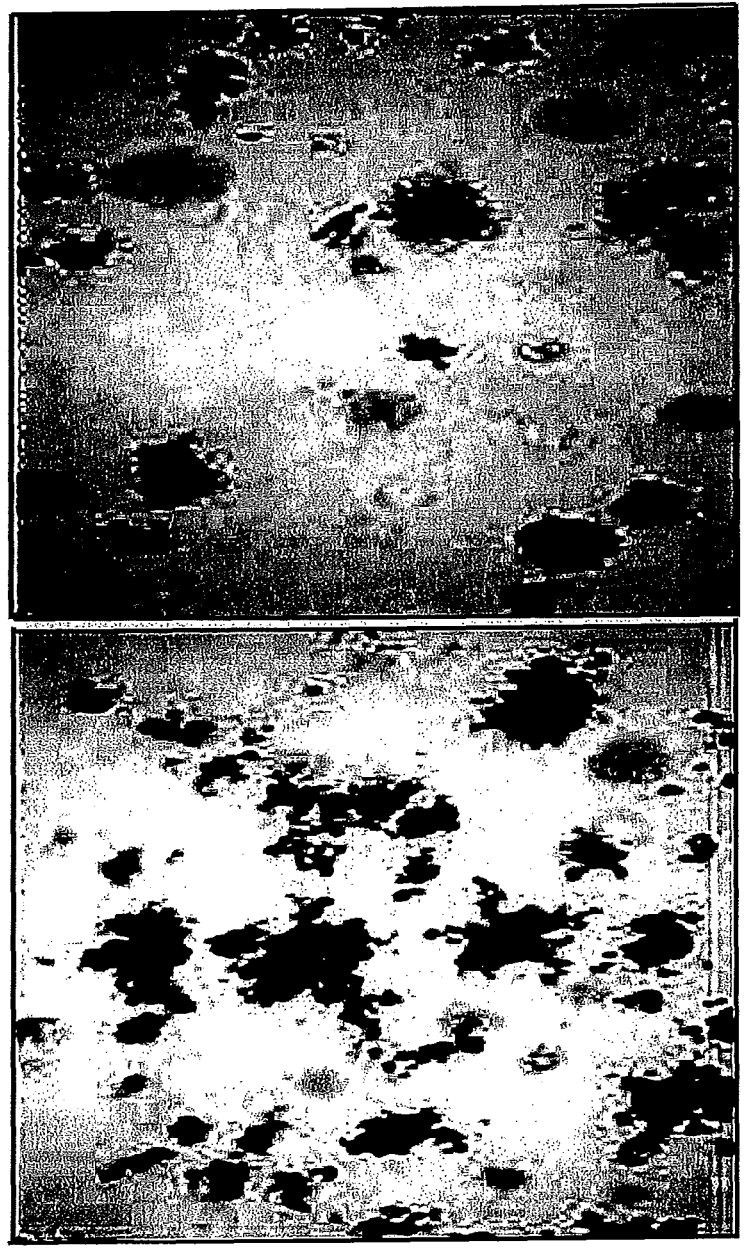
FIG. 12-FIG. 15 are diagrams illustrating the results of colony formation tests to examine tumor formation capacity of ZNF312b gene.
Figure 13:
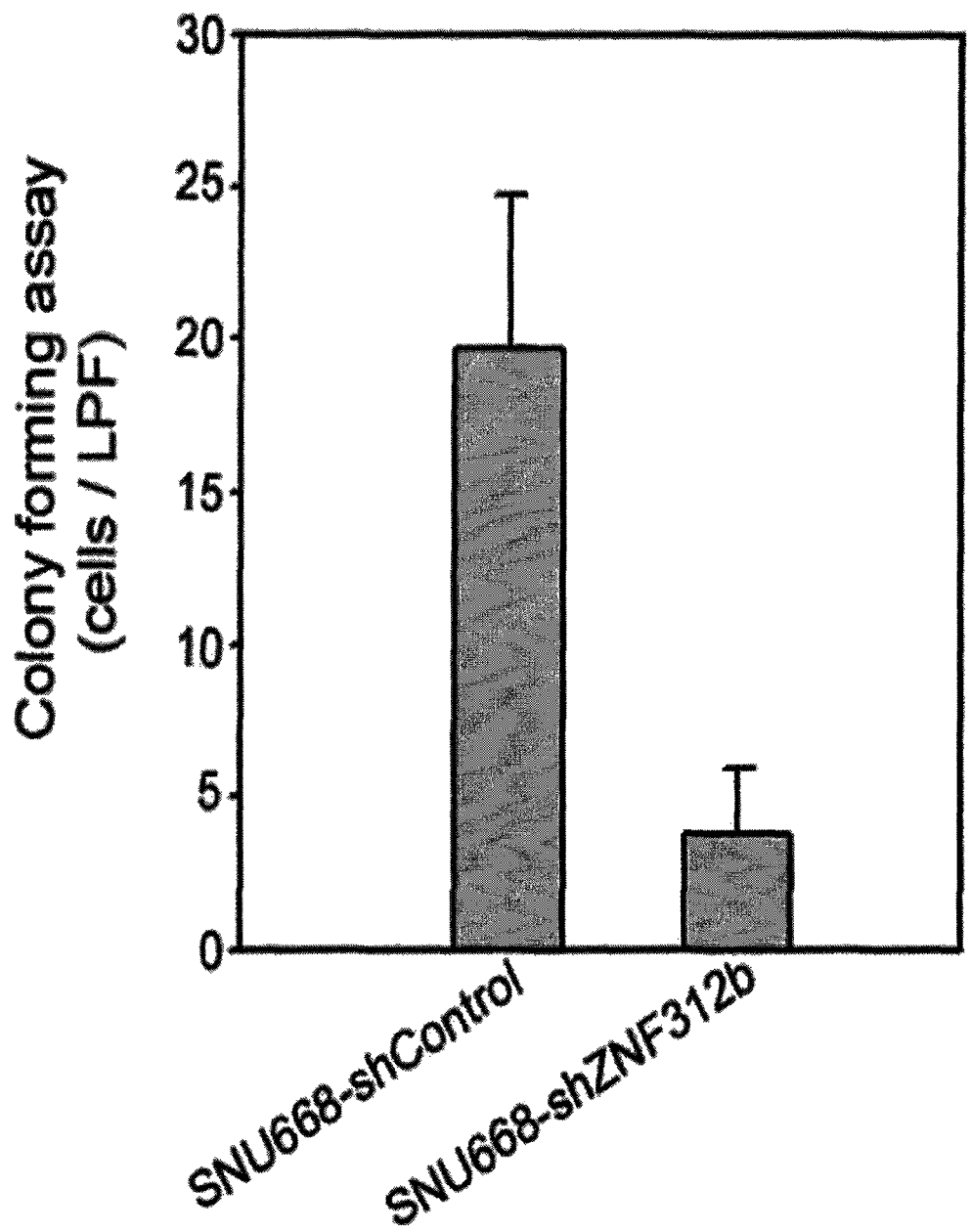
Figure 14:
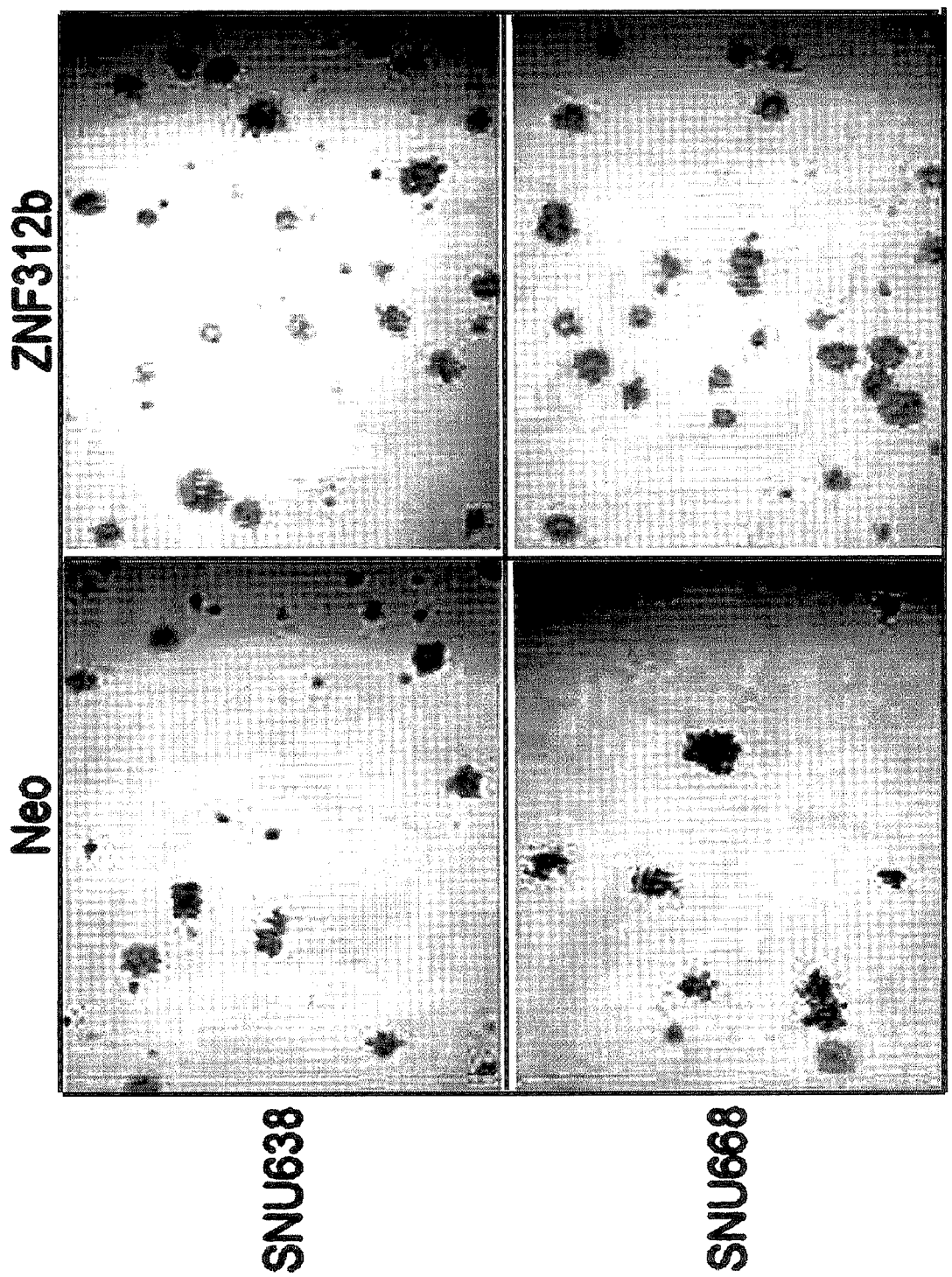
Figure 15:
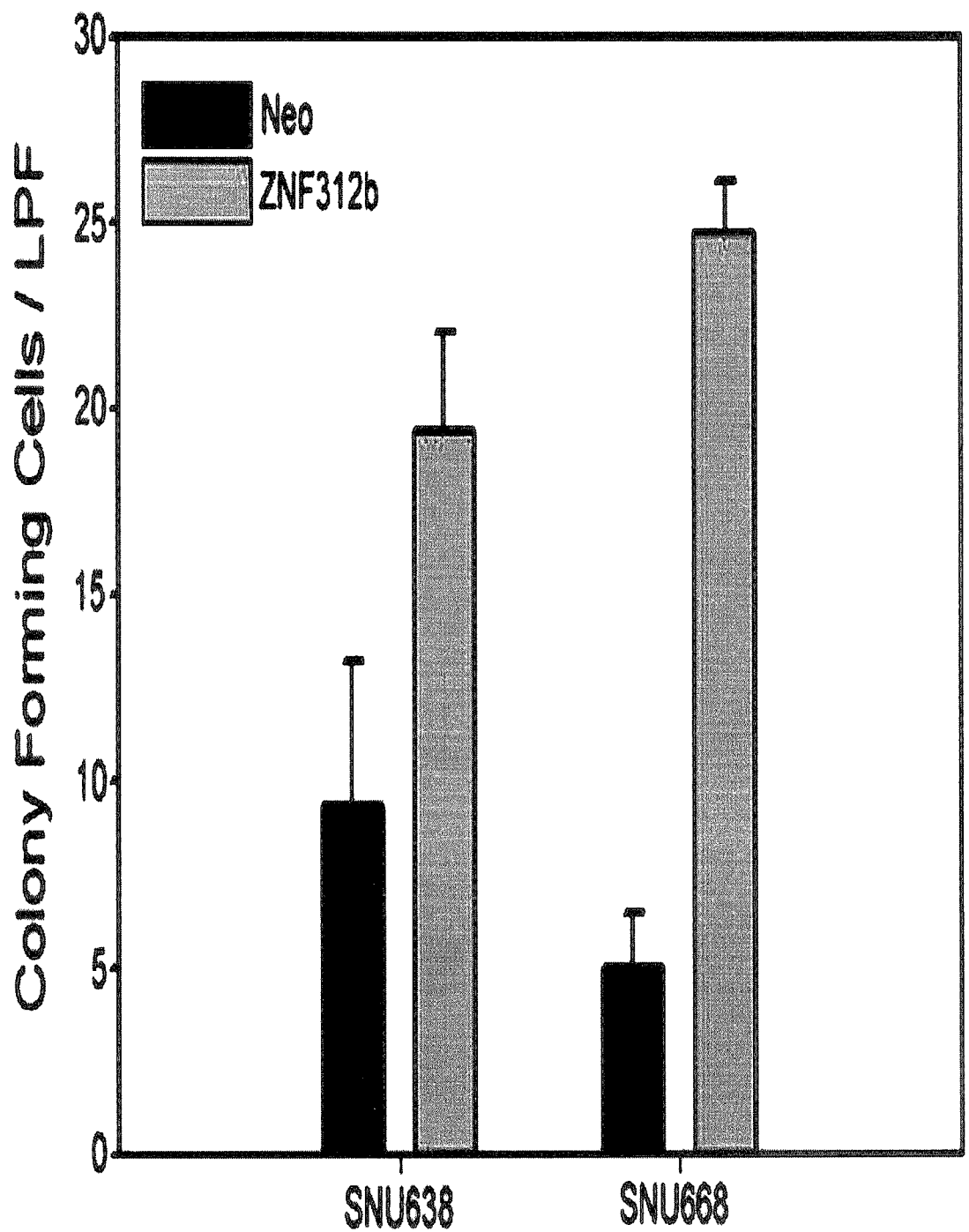

To investigate whether ZNF312b gene could be functioning as an oncogene, Colony forming assay was performed. First, 2×RPMI1640 (45° C.) was mixed with equal amount of 1.2% agarose solution to prepare 0.6% 1× medium, which was placed in a 6-well plate, followed by hardening for one hour. 5000 cells were diluted in 0.5 ml of the medium, which was mixed with equal amount of 0.6% agarose and then placed on the 0.6% agarose plate. After hardening the plate for one hour at room temperature, 1× medium was added thereto, followed by culture in a 37° C. incubator, during which colony formation was observed. The colonies were observed under microscope (100×) and the numbers counted were schematized. FIG. 12 and FIG. 13 illustrate the colony formation of ZNF312b knock-downed cell line SNU668-shZNF312b, and FIG. 14 and FIG. 15 illustrate the colony formation of ZNF312b over-expressing cell lines SNU638-ZNF312b and SNU668-ZNF312b. As a result, as shown in FIGS. 12-15, the colony formation was inhibited when ZNF312b expression was suppressed. In the meantime, the colony formation was increased when ZNF312b gene was over-expressed (FIGS. 12, 13, 14 and 15).

Example 9

Tumorigenecity Test

Figure 16:
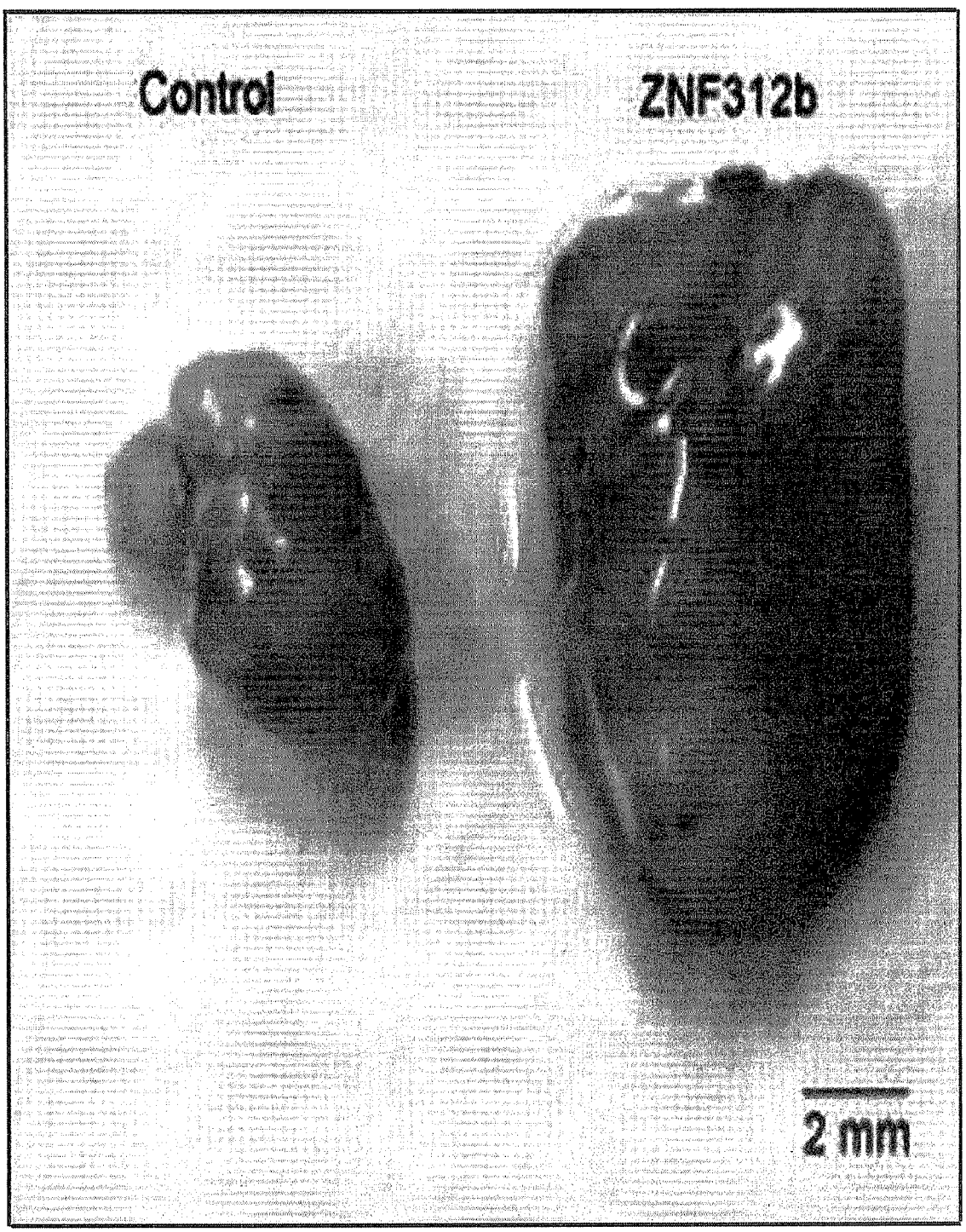
FIG. 16 and FIG. 17 are diagrams illustrating the results of tumor formation tests performed by transplanting ZNF312b over-expressing cell line SNU668-ZNF312b into nude mice.
Figure 17:
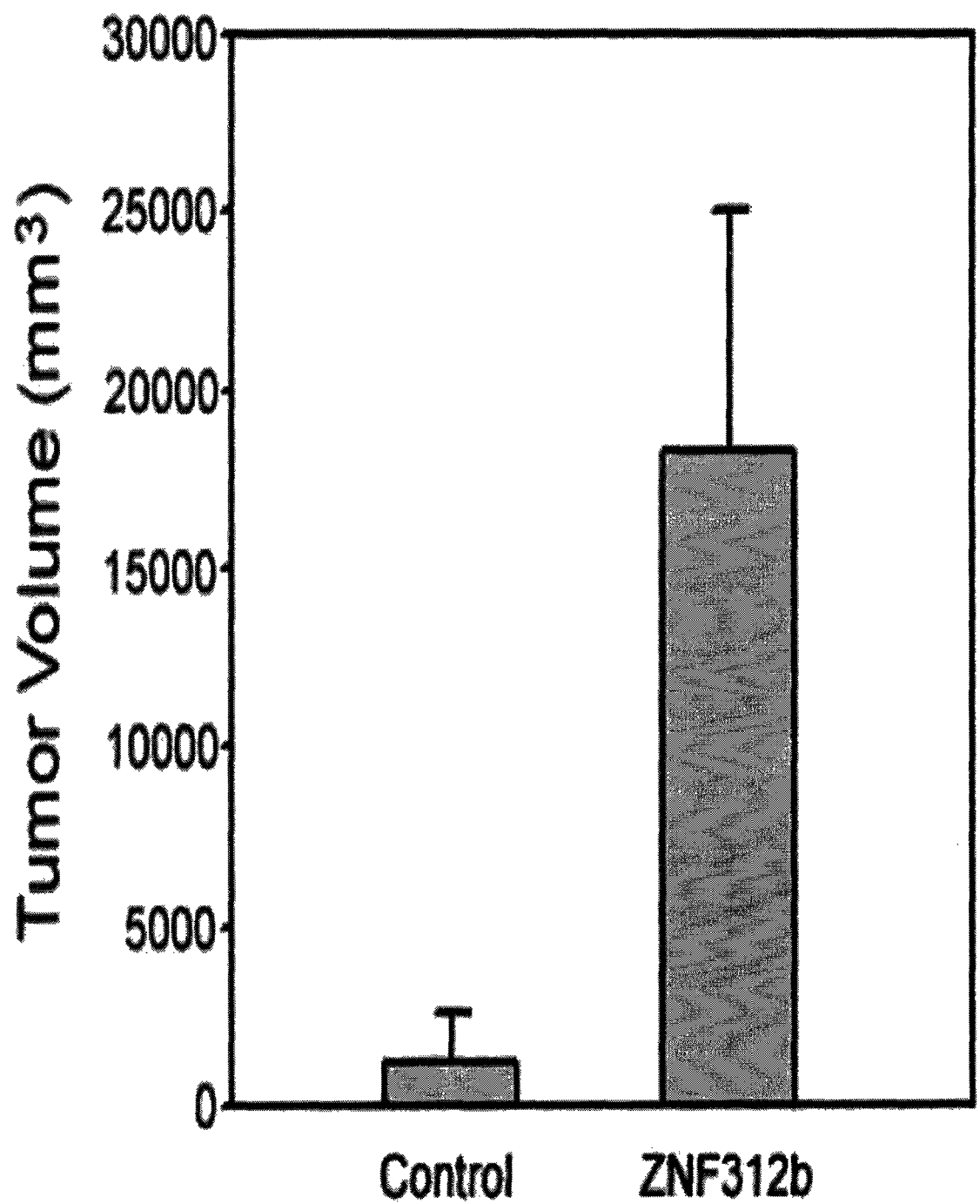

To confirm whether ZNF312b gene could be functioning as an oncogene, tumorigenicity test was performed using nude mice. The cell line established in Example <4-1>, SNU668-ZNF312b, and the control cell line, SNU668-Neo, were transplanted into nude mice respectively, followed by observation of tumorigenicity. For the experimental group, each cell line was inoculated to three nude mice at the density of $5 \times 10^5$ cells/mouse. 4 weeks after the inoculation, size of each tumor was measured and digitized for comparison. The tumor size ($mm^3$) was digitized by the formula of width×height/2. As a result, as shown in FIGS. 16 and 17, the tumor size in the nude mouse transplanted with ZNF312b over-expressing cell line SNU668-ZNF312b was significantly increased (FIGS. 16 and 17).

Example 10

Figure 18:
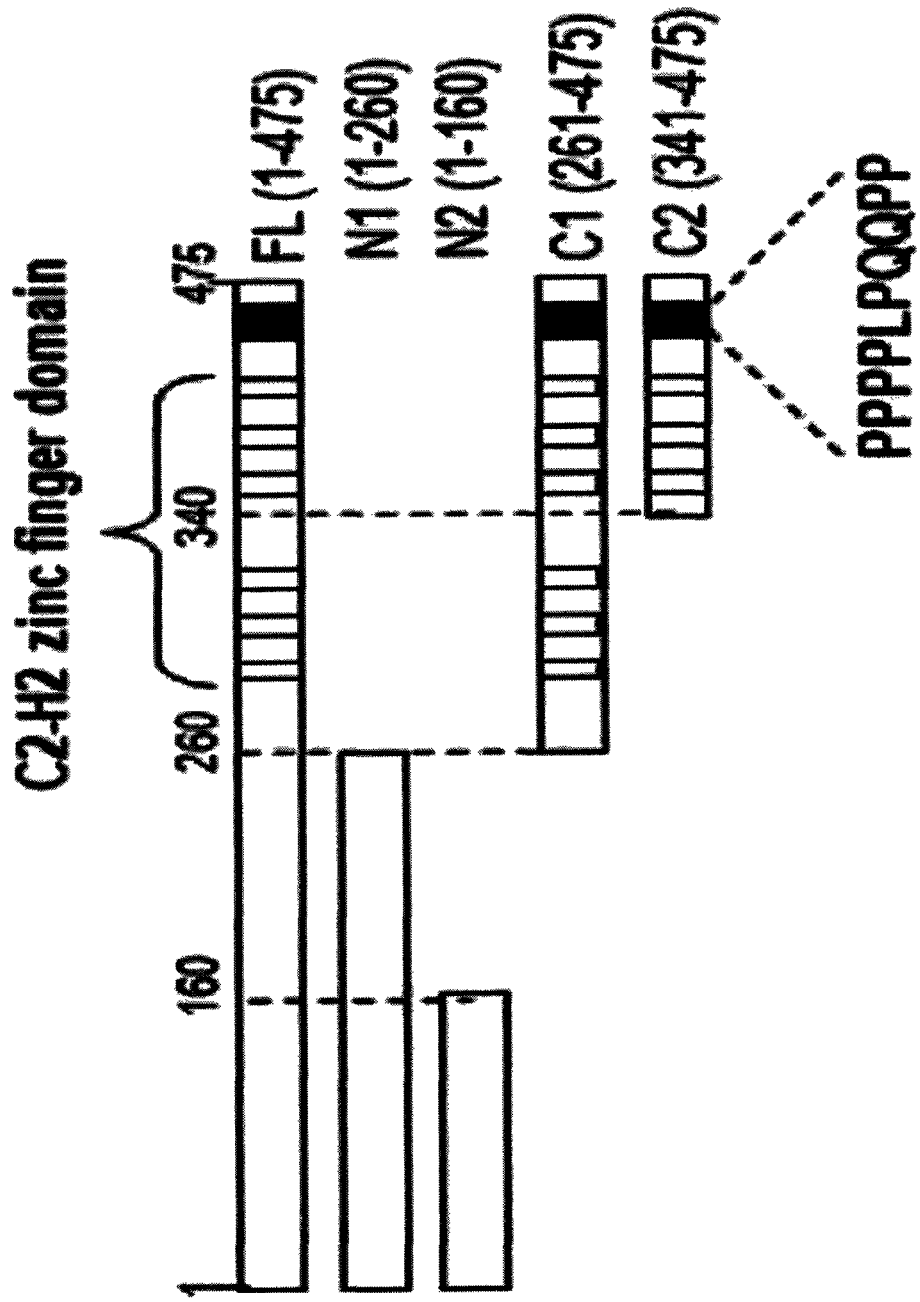
FIG. 18-FIG. 20 are diagrams illustrating the results of ZNF312b domain analysis and intracellular locations thereof, which were performed to identify the tumor-related active region of ZNF312b.

Construction of ZNF312b Deleted Fragments Over-Expressing Vector and Establishment of the Stomach Cancer Cell Line Thereof <10-1> Construction of ZNF312b Deleted Fragments Over-Expressing Vector The present inventors amplified the fragment of FIG. 7a by using pcDNA-ZNF312b vector as a template, and the amplified product was cloned into pcDNA vector. Particularly, PCR was performed using pcDNA-ZNF312b as a template with ZNF312b primers containing KpnI and BamHI restriction enzyme recognition sites. The obtained PCR product was purified and digested with KpnI and BamHI, which were inserted into pcDNA vector. As a result, pcDNA-ZNF312bN (N1), pcDNA-ZNF312bN2 (N2) and pcDNA-ZNF312bC1 (C1) and pcDNA-ZNF312bC2 (C2) expression vectors were constructed (FIG. 18).

<10-2> Establishment of Stomach Cancer Cell Line Over-Expressing ZNF312b Deleted Fragments The present inventors transfected the stomach cancer cell line SNU-638 with pcDNAZNF312-N1 and pcDNA-ZNF312b-C1, the vectors constructed in Example <10-1>, to establish the cell lines over-expressing full length ZNF312b and ZNF312b fragments, SNU638-ZNF312b (SNU638-FL), SNU638-ZNF312bN1 (SNU638-N1) and SNU638-ZNF312bC1 (SNU638-C1).

First, to establish ZNF312b over-expressing cell lines, the stomach cancer cell line SNU-638 was transfected with FL, N1 and C1 respectively using Fugene-6 (Roche, Germany). To select only those cells expressing the gene, 600 µg/ml of G418, the selection marker, was added to the culture solution. Colonies were separated to obtain the cell line containing a single clone. G418 containing medium was replaced every three days. Colonies formed therein were separated and cell numbers were increased, and some of which were used for the extraction of RNA or protein to investigate the gene expression and the rest was stored as frozen.

Example 11

Intracellular Localization of ZNF312b Deleted Fragments

<11-1> Nuclear Fractionation

The present inventors separated cytoplasm and nucleus by nuclear fractionation to localize ZNF312b in a cell and to identify the protein region necessary for transfer of the gene into nucleus. The present inventors confirmed by Western blotting that ZNF312b was in nucleus and the translocation into nucleus was mediated by carboxy-terminal (SEQ. ID. NO: 20).

Figure 19:
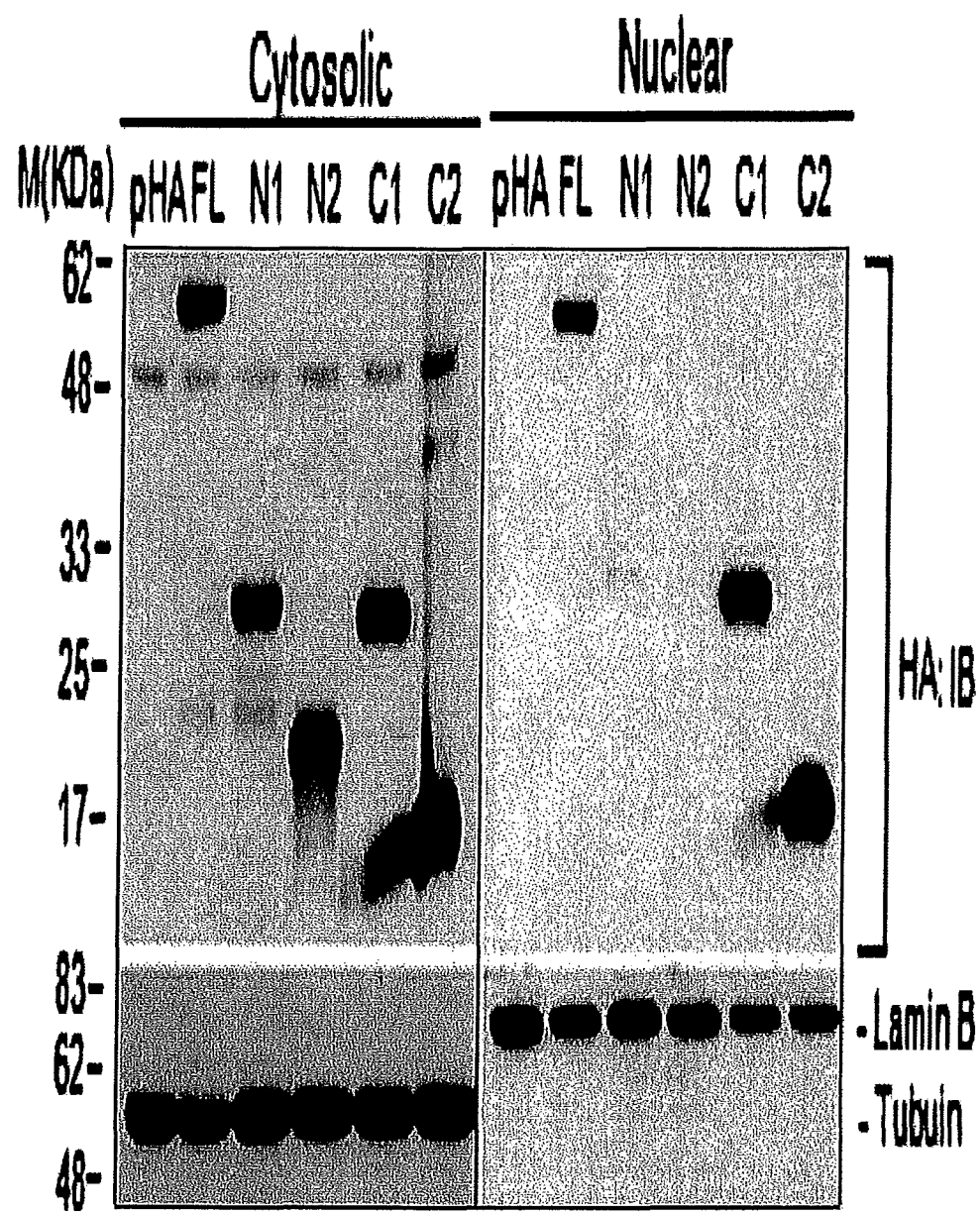

First, SNU-638 cells were transfected with ZNF312b and the fragment thereof. After expressing the gene and the fragment, the cells were recovered and washed with cold PBS twice. The cells were suspended in 1 ml of DNB [10 mM HEPES (pH7.5), 2 mM $MgCl_2$, 10 mM KCl, 0.5 mM EDTA, 0.5 mM EGTA, protease inhibitor cocktail I, II (Sigma, USA), and 0.2% NP-40], followed by rupturing using a 22-gauge needle syringe. The homogenate was centrifuged at 500×g for 10 minutes to separate nuclei. The nuclei were lysed in lysis buffer A [20 mM HEPES (pH7.5), 150 mM NaCl, 1 mM EDTA, 2 mM EGTA, 1% Triton X-100, 10% glycerol, protease cocktail I, II (Sigma, USA)]. Electrophoresis was performed under the same conditions as above to obtain nucleoproteins. As a result, as shown in FIG. 19, only ZNF312b fragments containing carboxy-terminal region were translocated into nucleus (FIG. 19).

<11-2> Localization by Immunostaining

Figure 20:
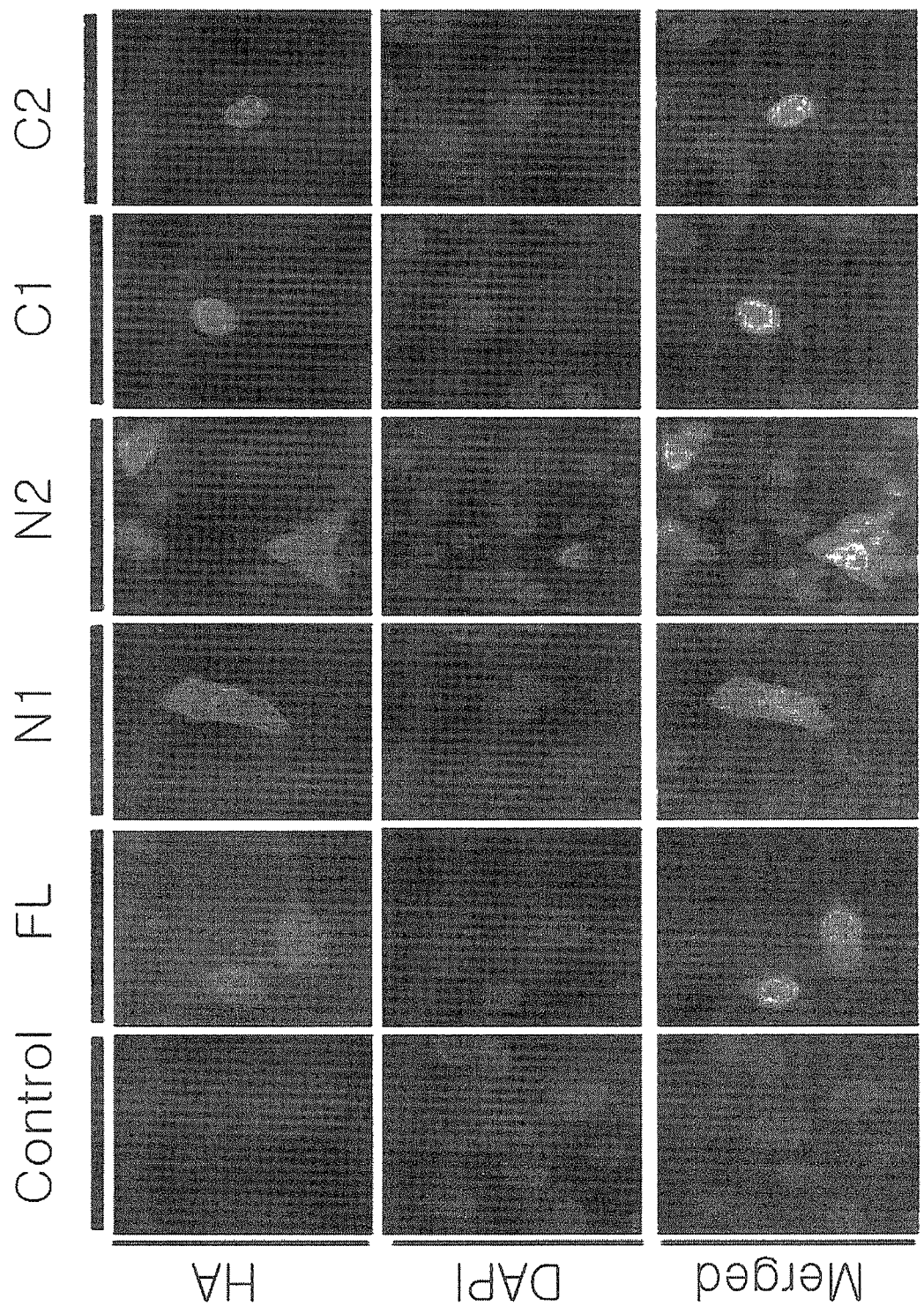

The cells expressing ZNF312b and the fragment thereof were placed on coverslip glass. 24 hours later, the cells were fixed on the glass by treating 4% paraformaldehyde for 20 minutes. The fixed cells were washed with PBS three times and treated with 1% Triton X-100 for 10 minutes, followed by blocking with 1% BSA at room temperature for one hour. The cells were reacted with monoclonal anti-HA at 4° C. for 12 hours. After washing with PBS three times, Alexa-568 conjugated anti-mouse secondary antibody was treated to the cells, followed by washing with PBS three times. After reacting with DPAI for 30 minutes, the cells were washed with PBS three times. Then, the cells accumulated on the slide were analyzed using fluorescent microscope (Olympus, Japan). As a result, as shown in FIG. 20, as consistent with the result of nuclear fractionation above, only ZNF312b fragments containing carboxy-terminal region were found in nucleus, while ZNF312b fragments containing amino-terminal region were found in cytoplasm (FIG. 20).

Example 12

Figure 21:
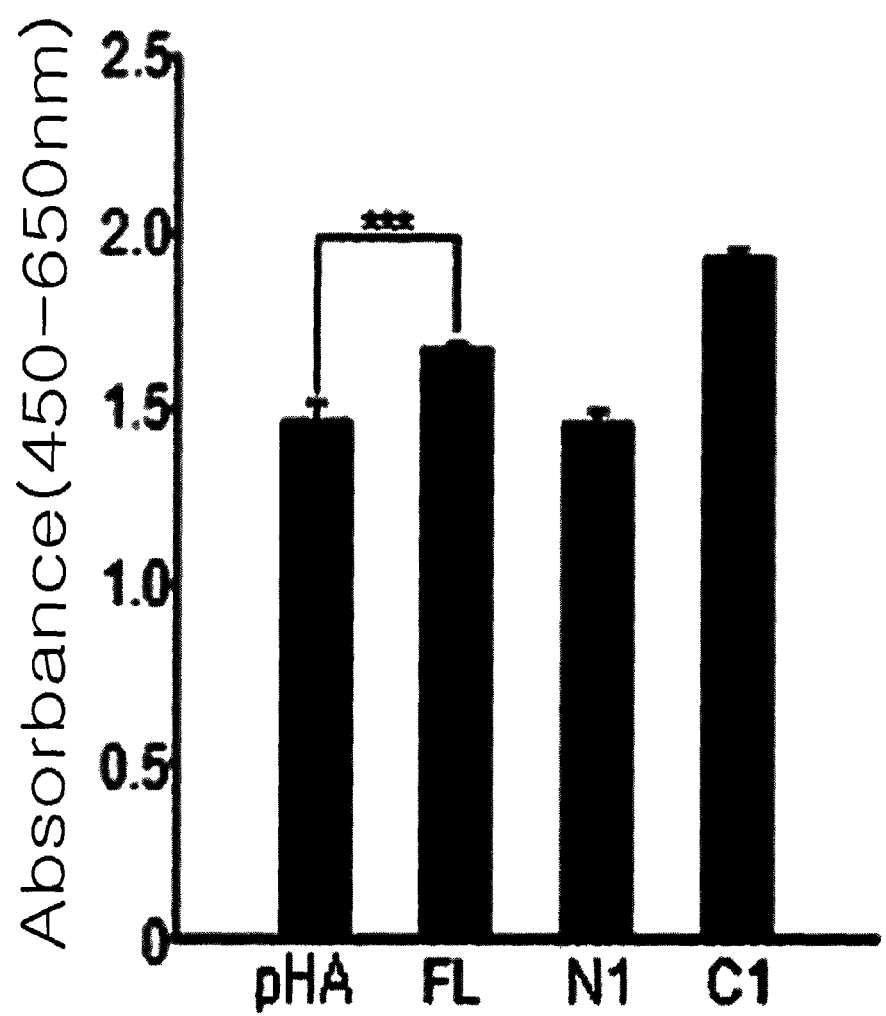
FIG. 21-FIG. 23 are diagrams illustrating the activation of cell proliferation and tumor formation capacity by over-expression of the full length ZNF312b and the fragment containing carboxy-terminal region of the ZNF312b.
Figure 22:
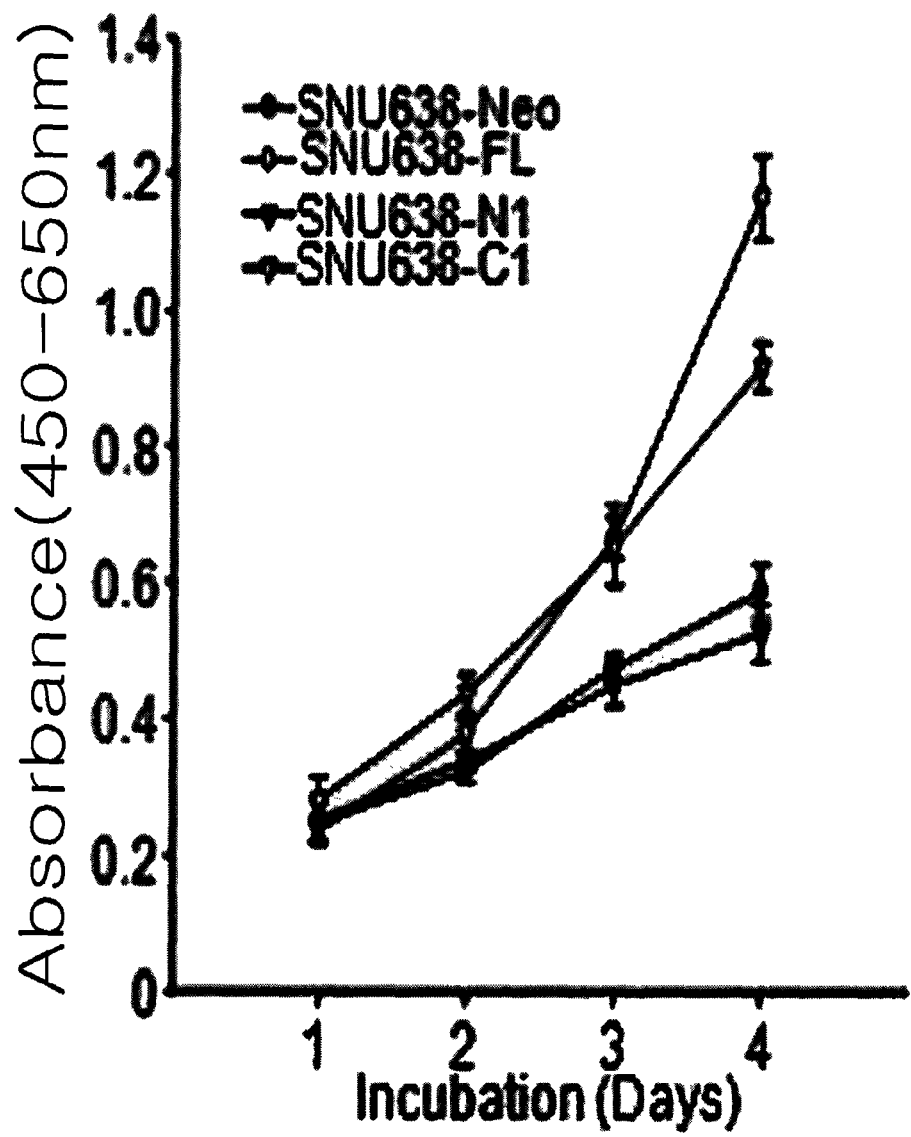

Investigation of Cell Proliferation and Colony Formation of ZNF312b Deleted Fragments Over-Expressing Stomach Cancer Cell Line <12-1> Cell Proliferation of ZNF312b Deleted Fragments Over-Expressing Stomach Cancer Cell Line The present inventors investigated cell proliferation of stomach cancer cell line using ZNF312b expressing cell line SNU638-FL established in Example <10-2> and ZNF312b deleted fragments expressing cell lines SNU SNU638-N1 and SNU638-C1. CCK-8 reagent was used for the cell proliferation experiment, like in the above Example <6-1>, and the cells were transiently transfected with the full length ZNF312b and the fragments thereof containing carboxy terminal region (SEQ. ID. NO: 20), followed by the experiment. As a result, as shown in FIG. 21, the transient over-expression of the gene increased the cell proliferation of those stomach cancer cell lines. As shown in FIG. 22, the constant expression of the gene increased the cell proliferation of the stomach cancer cell lines as well (FIGS. 21 and 22).

Figure 23:
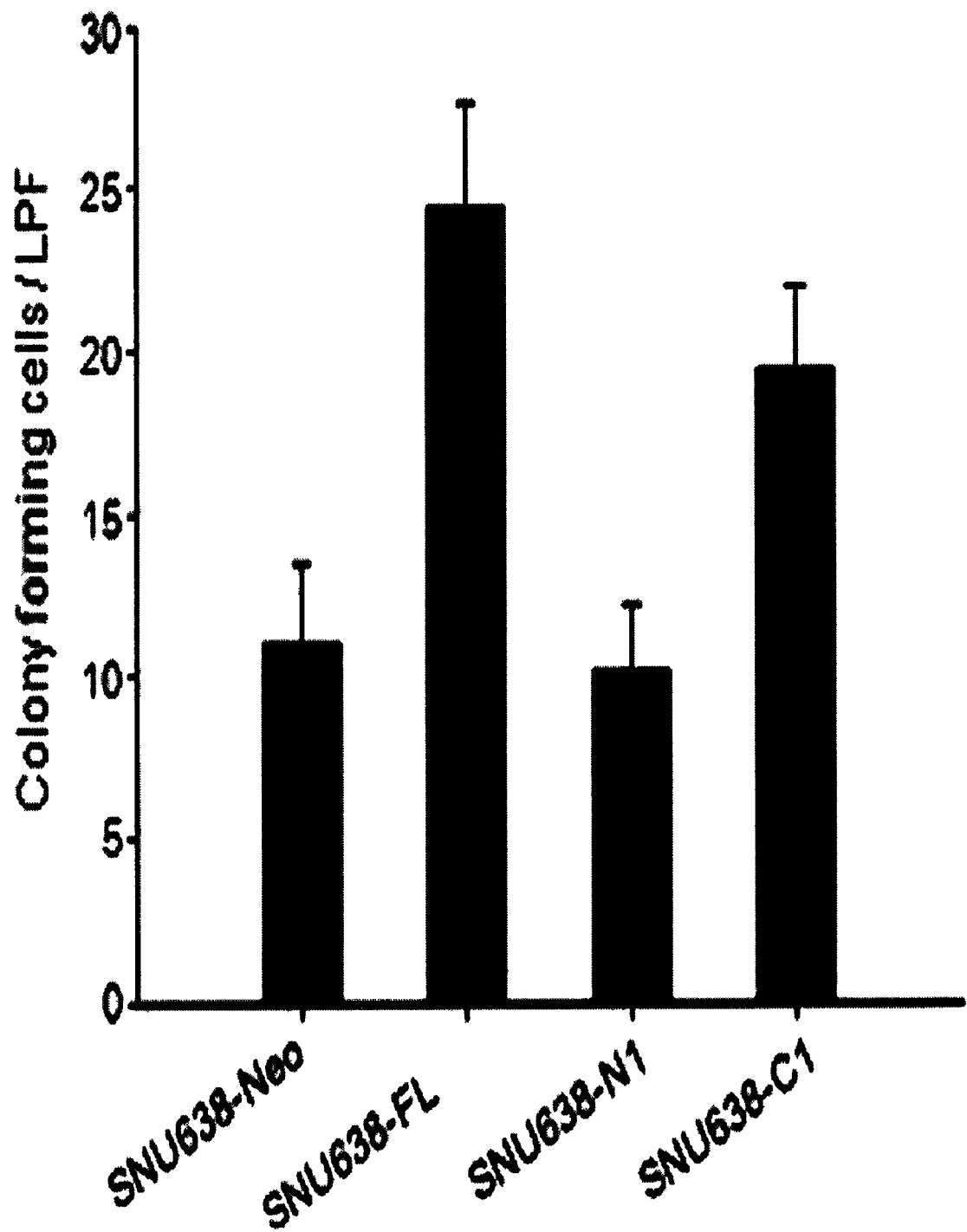

<12-2> Colony Forming Assay with ZNF312b Deleted Fragments Over-Expressing Stomach Cancer Cell Line The present inventors performed Colony forming assay with SNU638-FL, SNU638-N1 and SNU638-C1, the stomach cancer cell lines over-expressing the full length ZNF312b and the fragment thereof containing carboxy-terminal region of the gene, by the same manner as described in Example 8. As a result, as shown in FIG. 8c, colony formation was increased when the full length ZNF312b and the fragments thereof containing carboxy-terminal region of the gene were over-expressed. Therefore, it was confirmed that the carboxy-terminal region of ZNF312b protein plays critical role in the tumorigenecity of the stomach cancer (FIG. 23).

Example 13

Figure 24:
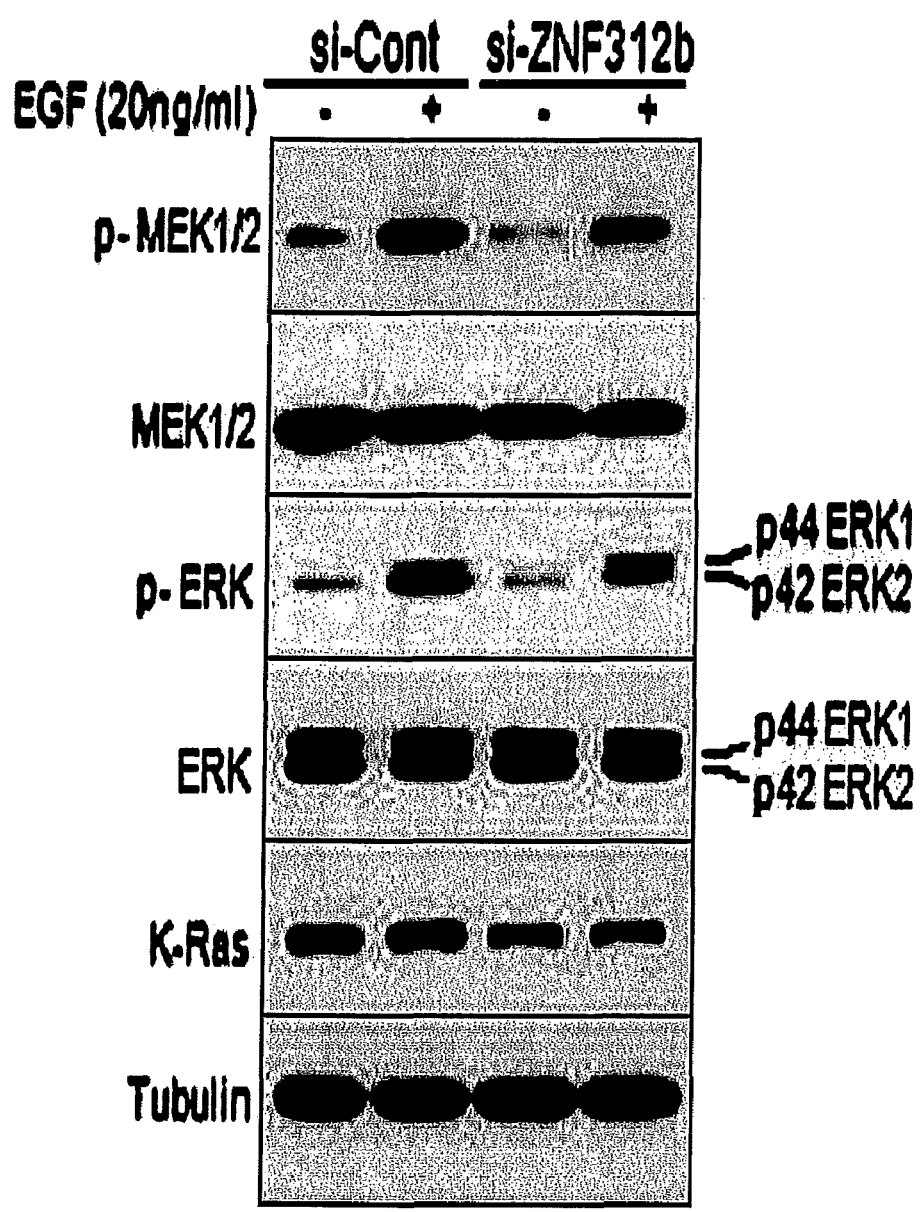
FIG. 24-FIG. 25 are diagrams illustrating the experiment for investigating tumorigenesis related mechanism of ZNF312b, which confirmed that ZNF312b regulated the transcription activity of K-ras, suggesting that ZNF312b activated RAS-ERK-pathway to induce cell proliferation.

Cell Proliferation Related Signaling System Induced by Over-Expression of ZNF312b and the Fragments Thereof <13-1> Cell Proliferation Related Signal Pathway by Inhibition of ZNF312b To investigate whether the signal pathway system involved in the cell proliferation of stomach cancer cell line was affected by inhibition of ZNF312b gene, the present inventors inhibited the expression of ZNF312b in stomach cancer cell line by transfecting the cell line with si-ZNF312b-1. Then, Western blotting was performed by the same manner as described in Example 5. At that time, such antibodies as phospho-MEK1/2, MEK1/2, phospho-ERK1/2, ERK1/2, K-ras, and tubulin were used. Then, it was investigated whether ZNF312b protein could regulate the K-ras expression by using the above antibodies and if so, it was investigated whether the regulated K-ras could affect ERK pathway, the cell proliferation signaling system. As a result, as shown in FIG. 24, the inhibition of ZNF312b resulted in the decrease of K-ras expression, suggesting that phosphorylation of MEK1/2 and ERK1/2ERK, leading to the inactivation of ERK pathway (FIG. 24).

Figure 25:
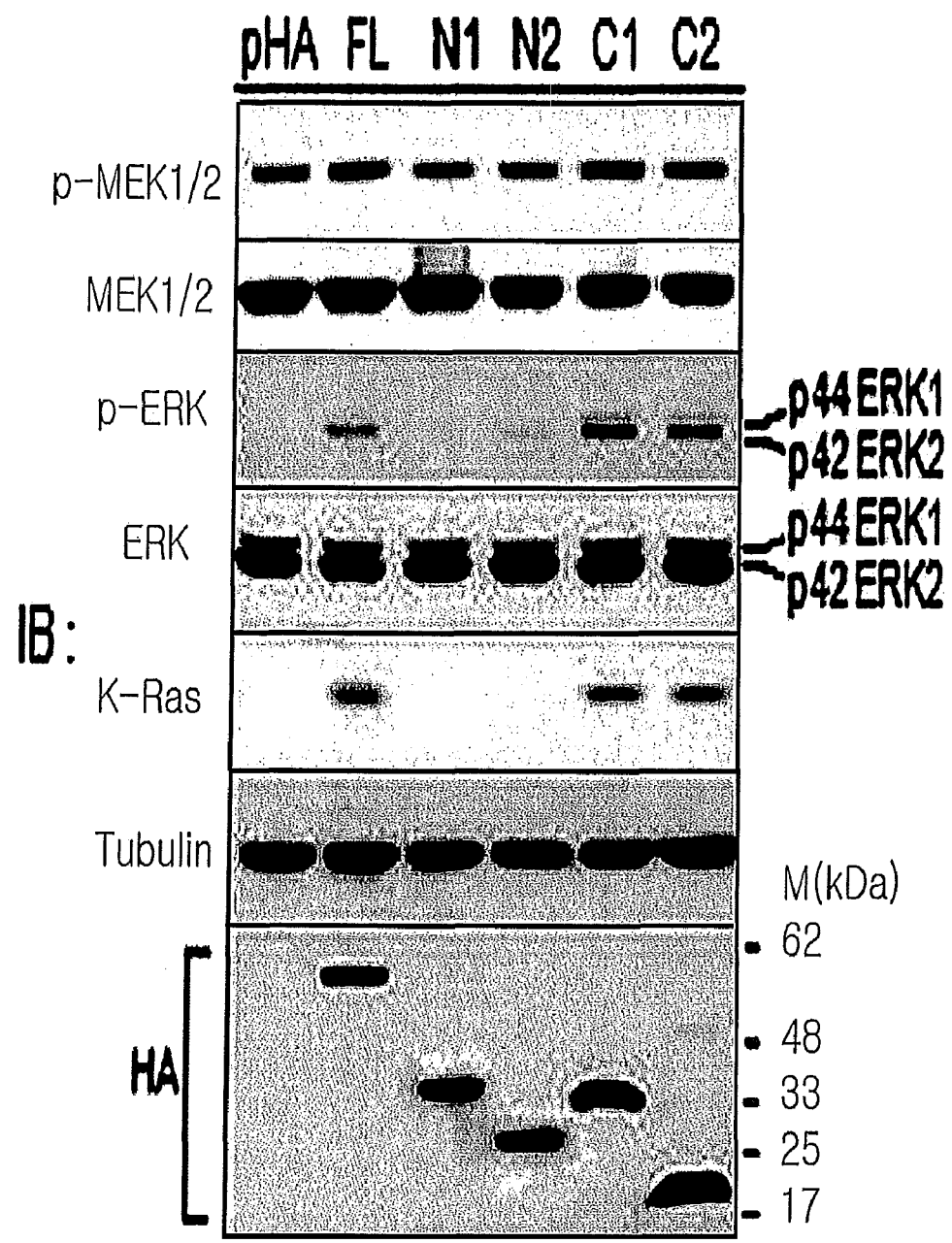

<13-2> Cell Proliferation Related Signal Pathway by Over-Expression of ZNF312b and the Fragments Thereof To investigate whether the signal transduction system involved in the cell proliferation of stomach cancer cell line was affected by over-expression of ZNF312b gene and the fragment thereof, SNU-638 cells were transfected with each fragment, followed by cell lysis. Signal transduction system was confirmed by the same manner as described in Example <13-1>. As a result, as shown in FIG. 25, the over-expression of the full length ZNF312b and the fragments thereof containing carboxy-terminal region of the gene increased the expression of K-ras, suggesting that ERK pathway was activated. Therefore, it was confirmed that ZNF312b regulated the cell proliferation related signal pathway_and the carboxy-terminal region played a key role for this regulation, suggesting that the carboxy-terminal region of ZNF312b is involved in stomach cancer development (FIG. 25).

Example 14

Construction of ZNF312b Promoter Expression Vector

<14-1> Construction of pGL3b-ZNF312b Vector Containing ZNF312b Promoter Region

Figure 26:
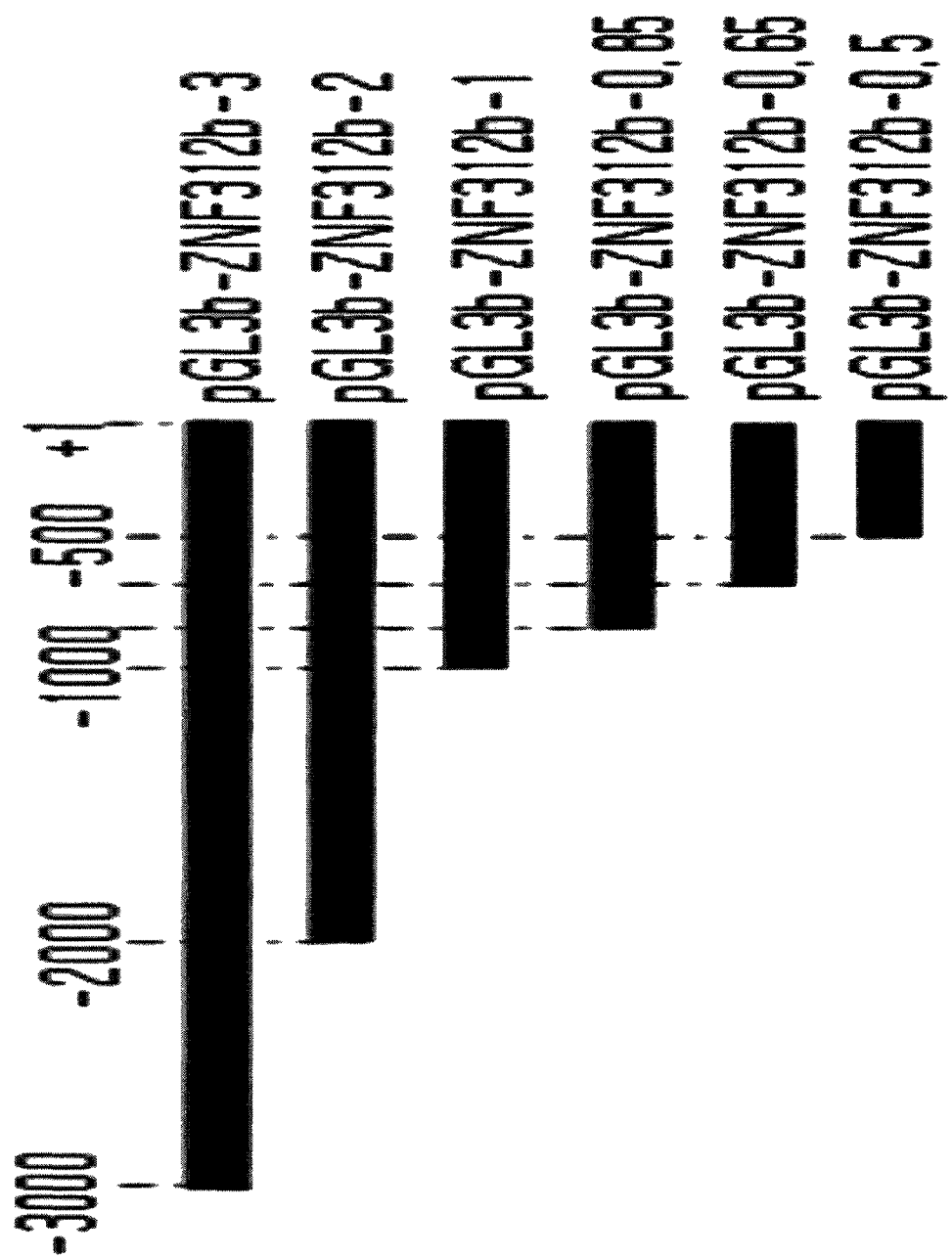
FIG. 26 is a diagram illustrating the vector map of pGL3b-ZNF312b inserted with different ZNF312b promoter regions.

To introduce ZNF312b promoter region into a vector capable of encoding luciferase reporter gene, the present inventors amplified ZNF312b promoter (SEQ. ID. NO: 9) and the fragment thereof (SEQ. ID. NO: 10) by PCR using primers containing NheI and BglII restriction enzyme sites. The amplified PCR product was inserted into pGL3 basic vector (Promega, USA). First, PCR was performed using SNU638 cDNA as a template and the amplified product was purified, which was digested with NheI and BglII. The fragments were then inserted into pGL3 basic vector to construct 6 different pGL3b-ZNF312b vectors containing ZNF312b promoter region (FIG. 26).

<14-2> Establishment of Cell Line Having Transient ZNF312b Promoter Transcription Activity To identify the active region of ZNF312b promoter (SEQ. ID. NO: 9) and the fragments thereof (SEQ. ID. NO: 10-NO: 14), the present inventors transfected the stomach cancer cell line SNU-638 with pGL3-ZNF312b, the vector constructed in Example <14-1>, to establish the cell line having transient ZNF312b promoter activity. First, the stomach cancer cell line SNU-638 ($2 \times 10^5$ cells) was transfected with 2 μg of pGL3-ZNF312b vector by using 6 μl of Lipofectamine 2000 (Invitrogen, USA), and then the cells were cultured for 48 hours.

Example 15

Transcription Activity of ZNF312b Promoter

The present inventors investigated the transcription activity of ZNF312b promoter in the cell line established in Example <14-2>. The measurement of the transcription activity was performed by measuring the activity of luciferase reporter by using luciferase assay system kit (Promega, USA).

First, the established cell line was placed in a 6-well plate at the density of $2.5 \times 10^5$ cells/well, followed by culture for 24 hours to distribute the cells evenly. The cells were lysed by adding 300 μl of cell lysis buffer. The cell lysate was centrifuged at 15,000 rpm for 10 minutes and the supernatant was transferred into a 1.5 ml new tube. According to Bradford method, standard curve was drawn by using 0, 1, 2, 3, 4 and 5 μg of BSA as the control, by which protein was quantified. $OD_{595}$ was measured with 2 μl of the cell extract. After quantification of the protein, luciferase activity was measured. 20 μl of the cell extract was mixed with 50 μl of the luciferase reporter substrate, followed by measuring the expression of the luciferase reporter gene by using Luminometer (Molecular Devices, Canada). Based on the expression level, the luciferase activity was calculated as follows.

$$\text{luciferase activity} = \frac{RLU \text{ of cell line having transcription activity of ZNF312b promoter/Protin quantity}}{RLU \text{ of control cell line/Protein quantity}}$$

Figure 27:
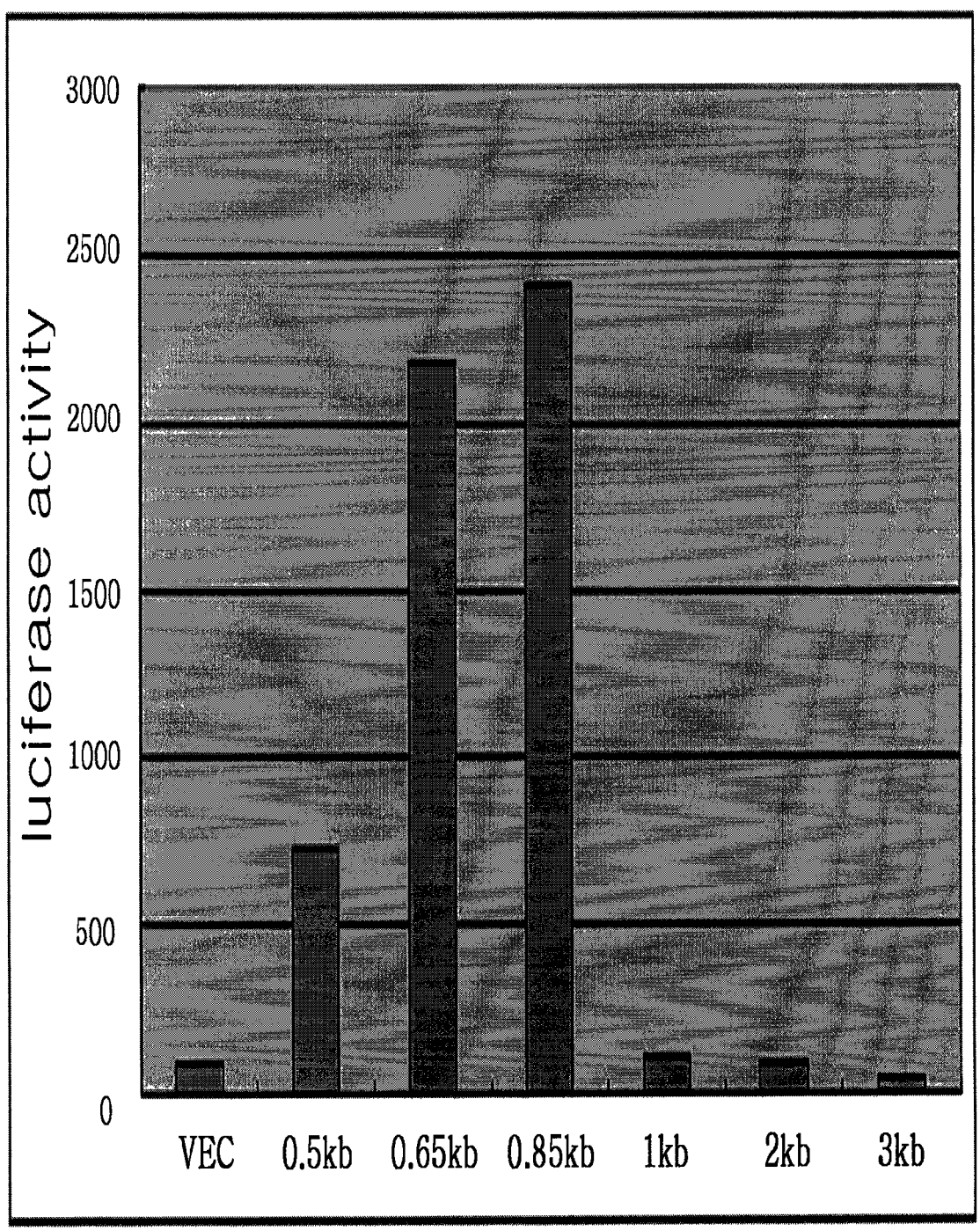
FIG. 27 is a diagram illustrating the activity of luciferase reporter gene in the stomach cancer cell line transfected with the pGL3b-ZNF312b vector.

As a result, as shown in FIG. 27, the clone containing the region of +1 bp~−850 bp (SEQ. ID. NO:12) of ZNF312b promoter demonstrated the highest luciferase activity, compared with the control (FIG. 27).

Example 16

Figure 28:
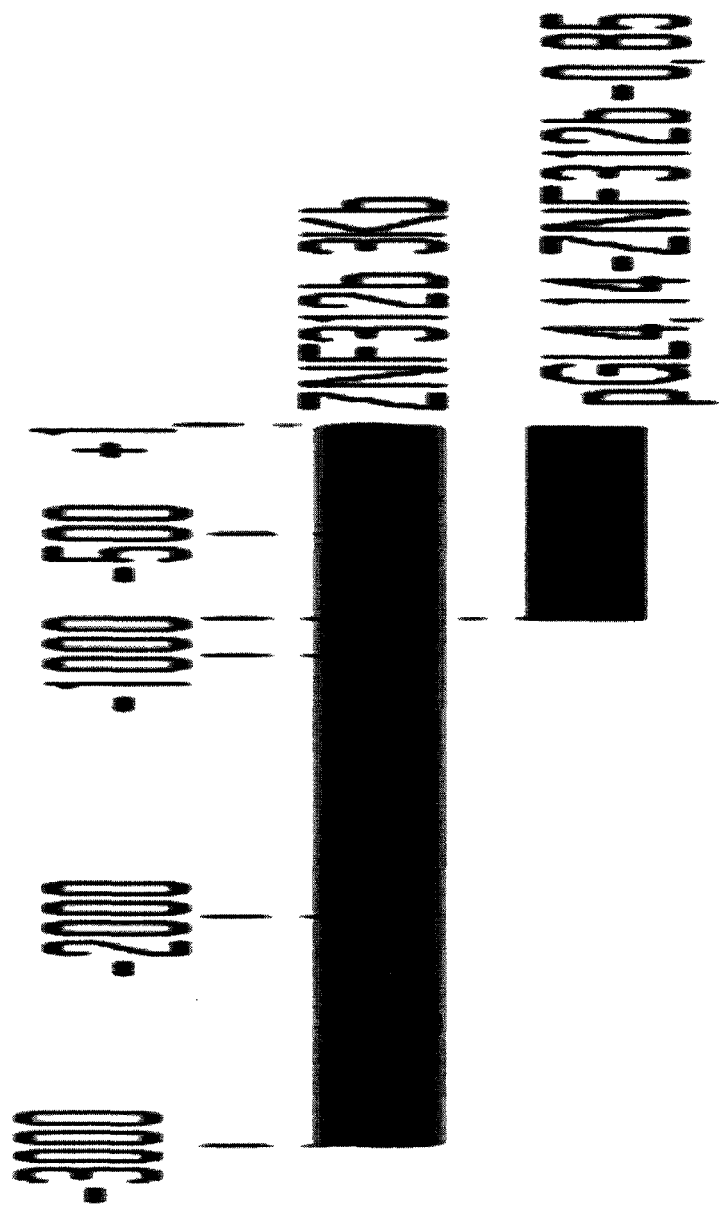
FIG. 28 is a diagram illustrating the vector map of pGL4.14-ZNF312b-0.85 inserted with the region of +1 bp~−850 bp of ZNF312b promoter.

Construction of Vector Containing the Region of +1 bp~−850 bp of ZNF312b Promoter and Establishment of the Stomach Cancer Cell Line Thereof <16-1> Construction of pGL4-ZNF312b Vector Containing ZNF312b Promoter Fragment To establish the cell line having constant transcription activity of the promoter fragment, the present inventors inserted the region of +1 bp~−850 bp (SEQ. ID. NO: 12) of ZNF312b promoter into pGL4.14 vector (Promega, USA) by using primers including NheI and HindIII restriction enzyme recognition sites. As a result, pGL4.14-ZNF312b-0.85 vector was constructed (FIG. 28).

<16-2> Establishment of Cell Line Having Constant ZNF312b Promoter Transcription Activity To establish the cell line having constant transcription activity of the region of +1 bp~−850 bp (SEQ. ID. NO: 12) of ZNF312b promoter, the present inventors transfected SNU-638 with the pGL4.14-ZNF312b-0.85 constructed in Example <16-1> by using Lipofectamine 2000 (Invitrogen, USA). After 48 hours of culture, 100 ug/ml of hygromycin, the selection marker, was added to the culture solution to select only the cells expressing the gene. To obtain the cell line containing a single clone, hygromycin containing medium was replaced every three days, followed by separation of colonies. The established cell line was used for the selection of effective compounds.

Example 17

Transcription Activity of ZNF312b Promoter

Figure 29:
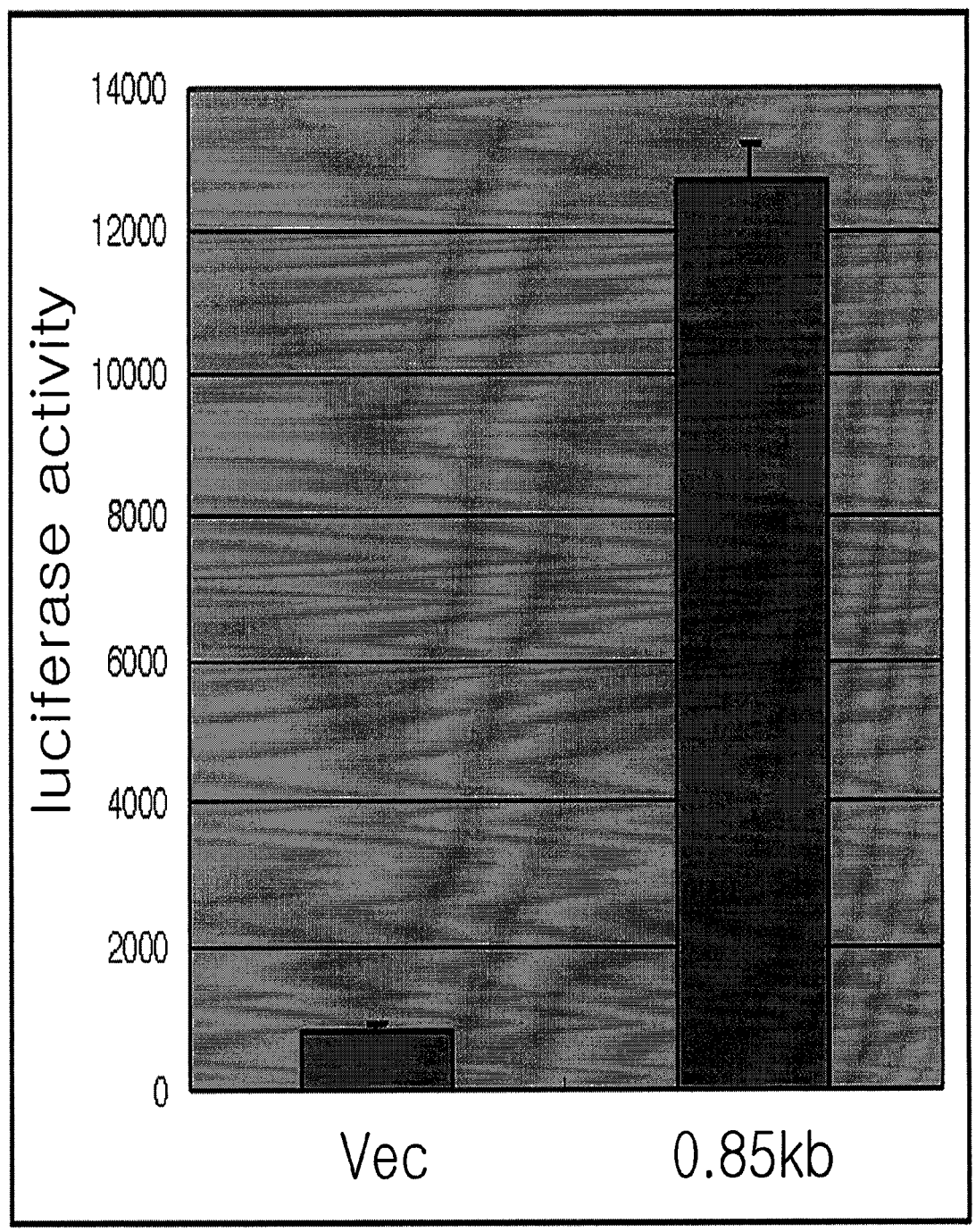
FIG. 29 is a diagram illustrating the activity of luciferase reporter gene in the stomach cancer cell line transfected with the pGL4.14-ZNF312b-0.85 vector.

Transcription activity of the region of +1 bp~−850 by (SEQ. ID. NO: 12) of ZNF312b promoter in the cell line established in Example <16-2> was measured by the same manner as described in Example 10. At that time, the pGL4.14-ZNF312b-0.85 containing cell line having constant ZNF312b promoter transcription activity was used. As a result, as shown in FIG. 29, the luciferase activity was approximately 15 fold increased, compared with the control (FIG. 29).

Example 18

Selection of Compounds Inhibiting Transcription Activity of ZNF312b Promoter The pGL4.14-ZNF312b-0.85 cell line established in Example <16-2> was placed in a 96-well plate at the density of $1 \times 10^4$ cells/well, and cultured for 24 hours to distribute the cells as an even layer. The sample compound was treated to 100 µl of the culture medium at the final concentration of 10 uM. At this time, the final concentration of DMSO containing the compound dissolved was adjusted to 0.3%. The cells were further cultured for 24 hours, and lysed in 25 µl of cell lysis buffer. 25 µl of the cell lysate was mixed with 20 µl of the luciferase reporter substrate. Then, the luciferase reporter activity was measured by the same manner as described in Example 10. Effective compounds were selected. For the control group, the cell line was treated with DMSO alone without the sample compound. Inhibition level of the reporter activity when each compound was treated was presented. The luciferase reporter inhibition activity was calculated by the following formula.

$$\text{luciferase reporter inhibition activity} = 100\% - \frac{RLU \text{ of cell line treated with compound/protein quantity}}{RLU \text{ of cell line treated with DMSO alone/protein quantity}} \times 100\%$$

As a result, as shown in Table 1, 27 compounds out of (50%) inhibited luciferase reporter activity at least 40% (Table 1).

TABLE 1

|   | 1   | 2   | 3   | 4   | 5   | 6   | 7   | 8   | 9   |
|---|-----|-----|-----|-----|-----|-----|-----|-----|-----|
| A | 0%  | 22% | 7%  | 29% | 42% | 29% | 56% | 24% | 40% |
| B | 4%  | 47% | 18% | 0%  | 38% | 52% | 41% | 42% | 43% |
| C | 29% | 0%  | 26% | 46% | 27% | 6%  | 63% | 41% | 44% |
| D | 28% | 1%  | 42% | 29% | 64% | 49% | 39% | 52% | 62% |
| E | 33% | 30% | 28% | 0%  | 40% | 22% | 62% | 62% | 45% |
| F | 0%  | 45% | 58% | 15% | 57% | 59% | 49% | 51% | 47% |

Example 19

Cytotoxicity of Compounds Inhibiting Transcription Activity

CCK-8 reagent (Dojindo, Japan) was used for the measurement of cytotoxicity of the selected compounds expected to inhibit ZNF312b transcription activity. This method uses tetrazolium salt, precisely this method facilitates the investigation of cytotoxicity by measuring conversion into hydrophilic formazan by endogenous dehydrogenase. Particularly, this method is to confirm cytotoxicity by measuring the conversion into hydrophilic formazan by intracellular dehydrogenase using tetrazolium salt. First, the pGL4.14-ZNF312b-0.85 cell line established in Example <16-2> was placed in a 96-well plate at the density of $1.5 \times 10^4$ cells/well, and cultured for 24 hours to distribute the cells as an even layer. The sample compound was treated to 100 µl of the culture medium at the final concentration of 10 uM. At this time, the final concentration of DMSO containing the compound dissolved was adjusted to 0.3%. After culturing the cells for 24 more hours, 10 µl of CCK-8 reagent was treated thereto, followed by measuring cytotoxicity.

As a result, as shown in Table 2, 16 compounds demonstrated less than 10% cytotoxicity (Table 2).

TABLE 2

|   | 1 | 2   | 3   | 4   | 5   | 6   | 7   | 8   | 9   |
|---|---|-----|-----|-----|-----|-----|-----|-----|-----|
| A | * | *   | *   | *   | 11% | *   | 9%  | *   | 21% |
| B | * | 11% | *   | *   | *   | 7%  | 13% | 12% | 8%  |
| C | * | *   | *   | 14% | *   |     | 1%  | 8%  | 0%  |
| D | * | *   | 12% | *   | 6%  | 11% |     | 10% | 7%  |
| E | * | *   | *   | *   | *   | *   | 9%  | 10% | 5%  |
| F | * | 10% | 7%  | *   | 8%  | 8%  | 9%  | 17% | 21% |

Example 20

Figure 30:
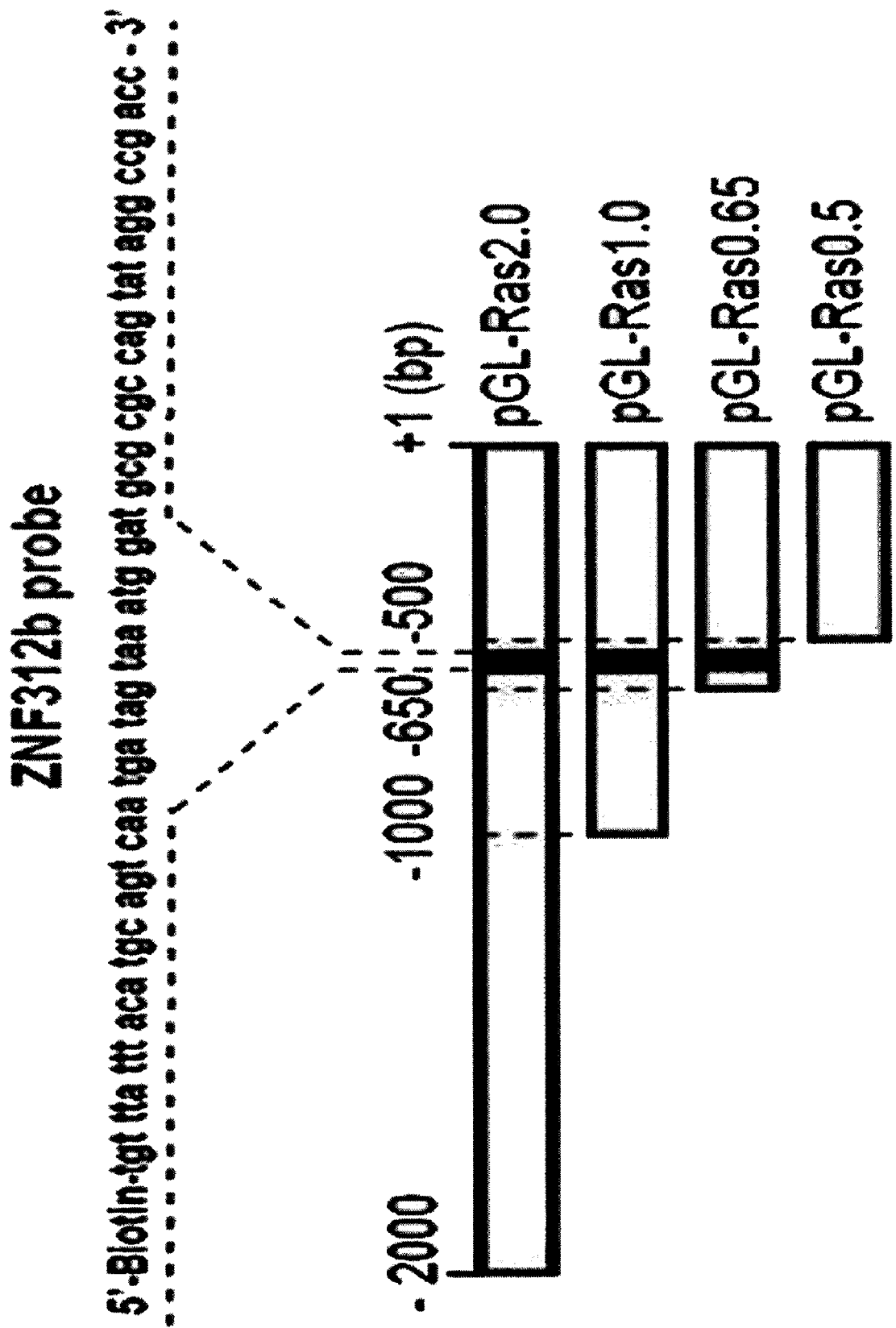
FIG. 30 is a diagram illustrating the different reporter vectors containing K-ras promoter.

Construction of pGL3b-K-ras Vector Containing K-ras Promoter Region and Establishment of the Stomach Cancer Cell Line Thereof <20-1> Construction of pGL3b-K-ras Vector Containing K-ras Promoter Region To disclose the mechanisms of K-ras over-expression and regulation by ZNF312b, the present inventors prepared K-ras promoter reporter. As shown in FIG. 30, K-ras promoter fragments, Ras2.0 (−2000~+1 bp; SEQ. ID. NO: 15), Ras1.0 (−1000~+1 bp; SEQ. ID. NO: 16), Ras0.65 (−650~+1 bp; SEQ. ID. NO: 17), and Ras0.5 (−500~+1 bp; SEQ. ID. NO: 18) were constructed (FIG. 30). As a reporter system to confirm whether the promoter was working, luciferase gene was used.

Each promoter fragment oligomer was amplified by PCR using human genomic DNA as a template, and the amplified product was cloned into pGL3 basic vector by using NheI/BglII.

<20-2> Establishment of Stomach Cancer Cell Line Having Transient K-ras Promoter Transcription Activity The present inventors transfected the stomach cancer cell line SNU-638 with the K-ras reporter (Ras2.0) of Example <20-1> along with the ZNF312(FL) and the fragments thereof (N1, N2, C1 and C2) of Example <10-1>, followed by culture for 48 hours.

Example 21

K-ras Promoter Reporter Activity

<21-1> K-ras Promoter Activity by ZNF312b and the Fragments Thereof

To measure the transcription activity of K-ras promoter in the cell line established in Example <20-2>, the present inventors examined the luciferase activity. The examination was performed with luciferase analysis kit according to the protocol of the kit. Particularly, the cells cultured in Example <20-2> were lysed, followed by centrifugation at 4° C. at 15000 rpm for 10 minutes to separate protein. The protein was quantified, followed by measuring the luciferase activity with luminometer (Molecular Device, Canada). At this time, 20 ul of the lysate and 50 ul of the luciferase substrate were used.

Figure 31:
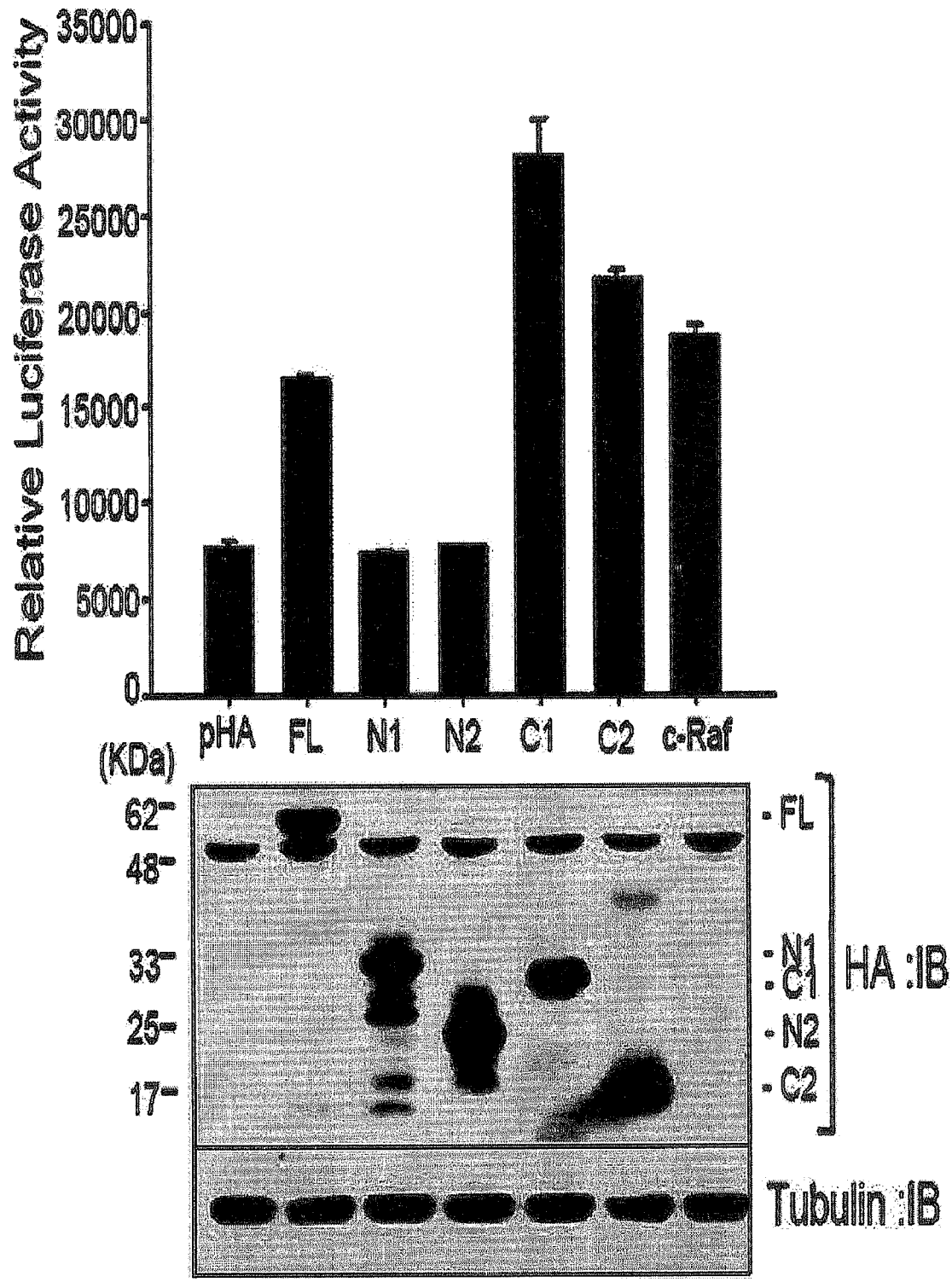
FIG. 31 is a diagram illustrating the activation of K-ras reporter by the expressions of ZNF312b gene and the fragment containing carboxy-terminal region of the gene.

As a result, as shown in FIG. 31, ZNF312b expression induced K-ras promoter activation, and accordingly increased the luciferase activity. The fragment of ZNF312b containing carboxy-terminal region produced the same result, which was the increase of the luciferase activity (FIG. 31).

<21-2> K-ras Promoter Trans-Element of ZNF312b

SNU-638 cells were transfected with each K-ras reporter (Ras 2.0, Ras 1.0, Ras 0.65 and Ras 0.5) and ZNF312b-C1 together. 48 hours later, the cells were lysed, followed by luciferase assay and Western blotting to measure the expression of ZNF312b-C1. The experiment was repeated three times to make sure the result was reliable.

Figure 32:
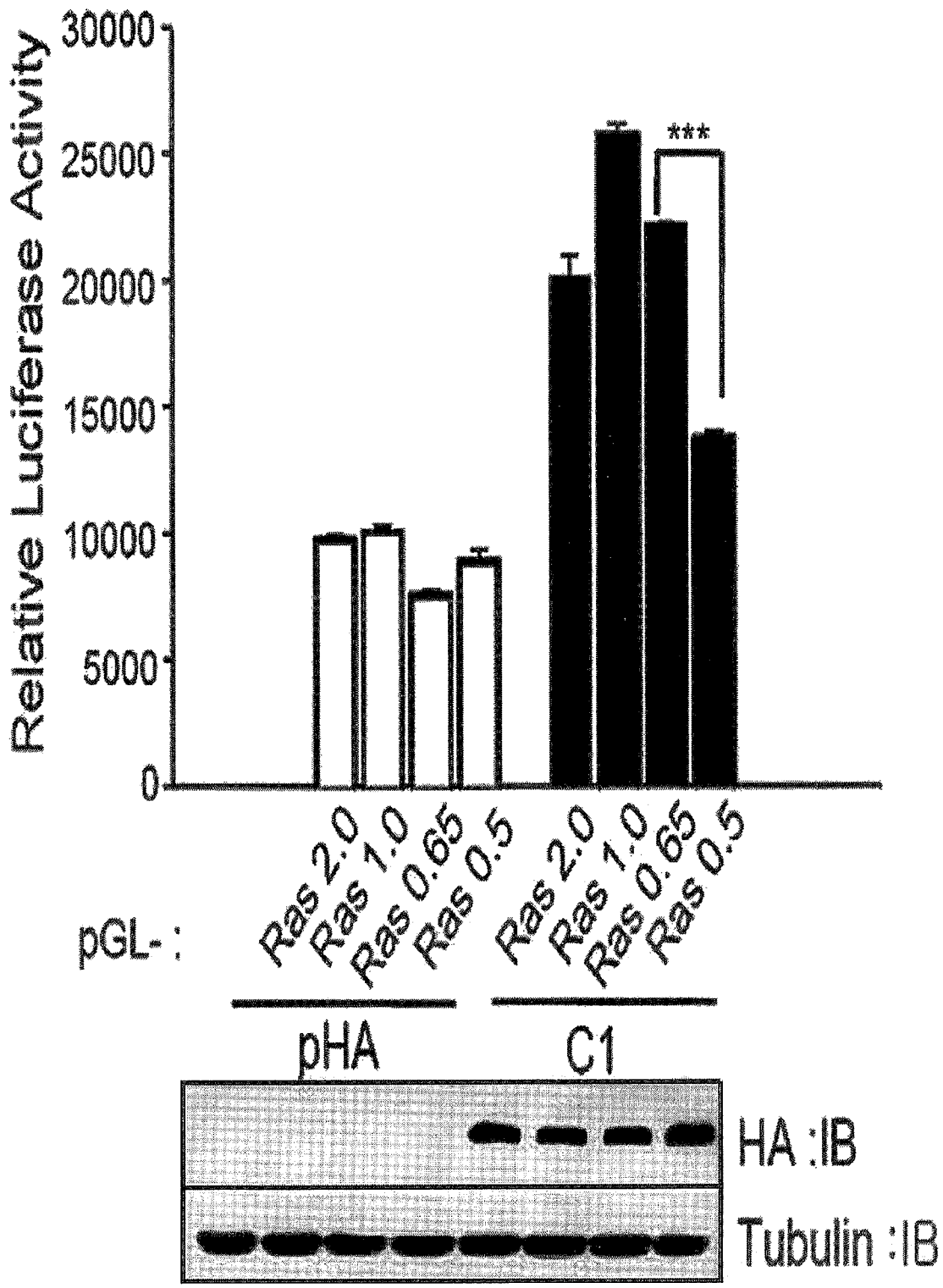
FIG. 32 is a diagram illustrating the identification of the K-ras promoter region activated by ZNF312b gene and the fragment containing carboxy-terminal region of the gene.

As a result, as shown in FIG. 32, the ZNF312b-C1 expression increased the K-ras reporter luciferase activity. However, the activity was decreased by Ras 0.5. Therefore, K-ras promoter binding site of ZNF312b was confirmed to be the region ranging from −650 bp to −500 bp (FIG. 32).

<21-3> Confirmation of Binding Between K-ras Promoter and its Binding Site of ZNF312b The present inventors used TransAM flexi DNA binding assay kit (Active motif, USA) to confirm whether the K-ras active site of ZNF312b was the region ranging from −650 bp to −500 bp.

First, SNU638 cells were transfected with ZNF312b fragments, and 48 hours later, nuclear fractionation was performed to obtain nuclear proteins. The nuclear protein was reacted with HA antibody for one hour. In the meantime, 57 bp region [5'-tgt tta ttt aca tgc agt caa tga tag taa atg gat gcg cgc cag tat agg ccg acc-3' (SEQ. ID. NO: 19)] which was presumed to be the zinc finger protein (ZNF) binding site was selected from the region ranging from −650 by to −500 bp of K-ras promoter and synthesized into 5'biotin conjugated oligo. The oligo was reacted with streptoavidine in a 96-well plate in TansAM Flexi DNA binding assay kit. The antibody and nuclear protein mixture was added thereto, followed by reaction for one hour. The reactant was washed twice with washing buffer, to which a secondary antibody was added, followed by reaction for one hour. The substrate was added, followed by observation of color reaction. After one hour of incubation, the color reaction was measured with ELISA microplate reader. ZNF312b protein in the nuclear protein was quantified by Western blotting.

As a result, as shown in FIG. 33, the presumed binding site of ZNF to the oligo DNA was confirmed in ZNF312b and ZNF312b fragment containing carboxy-terminal region, suggesting that ZNF312b binds to the ZNF binding site of K-ras promoter which is the region ranging from −650 bp to −500 bp (FIG. 33).

INDUSTRIAL APPLICABILITY

ZNF312b, the novel marker for diagnosis and treatment of stomach cancer of the present invention is over-expressed in a stomach cancer patient. Cell proliferation and tumor formation capacity of a stomach cancer cell line is activated by the over-expression of the gene. In the meantime, cell proliferation and tumor formation capacity is suppressed by the knock-down of the gene. Therefore, ZNF312b can be effectively used for diagnosis of stomach cancer, construction of a stomach cancer animal model, prevention and treatment of stomach cancer and development of a stomach cancer specific anticancer agent.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for inhibiting proliferation of gastric tumor cells comprising administering to said tumor cells an effective amount of a ZNF312b (Zinc finger protein 312b) gene expression inhibitor, wherein the ZNF312b gene expression inhibitor is:

an antisense polynucleotide with a complementary sequence to the mRNA transcribed from a ZNF312b gene comprising the nucleotide sequence as set forth in SEQ ID NO:1 or a fragment thereof containing the carboxy-terminal region of ZNF312b gene comprising the nucleotide sequence coding the amino acid sequence as set forth in SEQ ID NO:20, thereby specifically inhibiting expression of the ZNF312b gene, a siRNA (small interfering RNA) molecule which comprises a sequence having the complementary sequence to the mRNA transcribed from the ZNF312b gene comprising the nucleotide sequence as set forth in SEQ ID NO:1 or a fragment thereof containing the carboxy-terminal region of the ZNF312b gene comprising the nucleotide sequence coding the amino acid sequence as set forth in SEQ ID NO:20, thereby specifically inhibiting expression of the ZNF312b gene.

2. The method of claim 1, wherein the siRNA molecule is selected from the group consisting of the siRNA as set forth in SEQ ID NO:6, SEQ ID NO:7 and SEQ ID NO: 8.

* * * * *